United States Patent
Schinazi et al.

(10) Patent No.: US 11,963,972 B2
(45) Date of Patent: Apr. 23, 2024

(54) ANTIVIRAL AGENTS AND NUCLEOSIDE ANALOGS FOR TREATMENT OF ZIKA VIRUS

(71) Applicant: Emory University, Atlanta, GA (US)

(72) Inventors: Raymond F. Schinazi, Atlanta, GA (US); Franck Amblard, Atlanta, GA (US); Bryan D. Cox, Suwanee, GA (US); Leda Bassit, Smyrna, GA (US); Longhu Zhou, Atlanta, GA (US); Christina Gavegnano, Atlanta, GA (US)

(73) Assignee: Emory University, Atlanta, GA (US)

( * ) Notice: Subject to any disclaimer, the term of this patent is extended or adjusted under 35 U.S.C. 154(b) by 1072 days.

(21) Appl. No.: 16/088,017

(22) PCT Filed: Mar. 22, 2017

(86) PCT No.: PCT/US2017/023537
§ 371 (c)(1),
(2) Date: Sep. 24, 2018

(87) PCT Pub. No.: WO2017/165489
PCT Pub. Date: Sep. 28, 2017

(65) Prior Publication Data
US 2023/0000893 A1    Jan. 5, 2023

Related U.S. Application Data

(60) Provisional application No. 62/312,225, filed on Mar. 23, 2016.

(51) Int. Cl.
| | | |
|---|---|---|
| *A01N 43/04* | (2006.01) | |
| *A61K 31/4706* | (2006.01) | |
| *A61K 31/53* | (2006.01) | |
| *A61K 31/655* | (2006.01) | |
| *A61K 31/70* | (2006.01) | |
| *A61K 31/7064* | (2006.01) | |
| *A61K 31/7068* | (2006.01) | |
| *A61P 31/14* | (2006.01) | |

(52) U.S. Cl.
CPC ...... *A61K 31/7068* (2013.01); *A61K 31/4706* (2013.01); *A61K 31/53* (2013.01); *A61K 31/655* (2013.01); *A61K 31/7064* (2013.01); *A61P 31/14* (2018.01)

(58) Field of Classification Search
None
See application file for complete search history.

(56) References Cited

U.S. PATENT DOCUMENTS

2012/0189614 A1    7/2012  Basu
2014/0065101 A1    6/2014  Yokokawa

FOREIGN PATENT DOCUMENTS

| WO | 2004013298 | 2/2004 |
| WO | 2008143846 | 11/2008 |
| WO | 2010068708 | 6/2010 |
| WO | 2010091386 | 8/2010 |
| WO | 2012142523 | 10/2012 |
| WO | 2012158811 | 11/2012 |
| WO | 2014070771 | 5/2014 |
| WO | 2016069975 | 5/2016 |
| WO | 2017070355 | 4/2017 |
| WO | 2017156255 | 9/2017 |

OTHER PUBLICATIONS

Barrows et al. A screen of FDA-approved drugs for inhibitors of Zika virus infection, Cell Host Microbe. 2016, 10; 20 (2): 259-270.
Ekins et al. Open Drug Discovery for the Zika Virus, F1000Research, 2016, 5:150.
Kasthuri et al. Synthesis of 4'-Substituted-2'-Deoxy-2'-a-Fluoro Nucleoside Analogs as Potential Antiviral Agents, Molecules, 2020, 25, 1258.
Quicke et al. Zika Virus Infects Human Placental Macrophages, Cell Host & Microbe, 2016, 20, 83-90.
Sari et al., Synthesis and antiviral evaluation of 2',2',3',3'-tetrafluoro nucleoside analogs, Tetrahedron Lett, 2017, 58 (7): 642-644.
Warren et al. Protection against filovirus diseases by a novel broad-spectrum nucleoside analogue BCX4430, Nature, 2014, 508(7496):402-5.
Xu et al. Identification of small molecule inhibitors of Zika virus infection and induced neural cell death via a drug repurposing screen, Nat Med, 2016, 22(10): 1101-1107.
Zmurko et al. The Viral Polymerase Inhibitor 7-Deaza-2'-C-Methyladenosine Is a Potent Inhibitor of In Vitro Zika Virus Replication and Delays Disease Progression in a Robust Mouse Infection Model, PLoS Negl Trop Dis, 2016, 10 (5):e0004695.
Belen'Kii & Schinazi, Multiple drug effect analysis with confidence interval, Antiviral Research, 1994, 25:1-11.
Cui et al. Effect of P-Enantiomeric and Racemic Nucleoside Analogues on Mitochondrial Functions in HepG2 Cells, Biochemical Pharmacology, vol. 52, pp. 1577-1584, 1996.
Feng et al. Relationship between Antiviral Activity and Host Toxicity: Comparison of the Incorporation Efficiencies of 2',3'-Dideoxy-5-Fluoro-3'-Thiacytidine-Triphosphate Analogs by Human Immunodeficiency Virus Type 1 Reverse Transcriptase and Human Mitochondrial DNA Polymerase, Antimicrobial Agents and Chemotherapy, Apr. 2004, p. 1300-1306.
Kuiper et al. Increased activity of unlinked Zika virus NS2B/NS3 protease compared to linked Zika virus protease, Biochemical and Biophysical Research Communications 492 (2017) 668-673.

(Continued)

*Primary Examiner* — Patrick T Lewis
(74) *Attorney, Agent, or Firm* — Emory Patent Group

(57) ABSTRACT

The present invention is directed to compounds, compositions and methods for treating or preventing Zika virus. The compounds include pyrimidine and purine nucleosides and prodrugs thereof, including certain $N^4$-hydroxycytidine nucleoside derivatives, sulfasalazine, and various entry inhibitors.

Figure 1B:
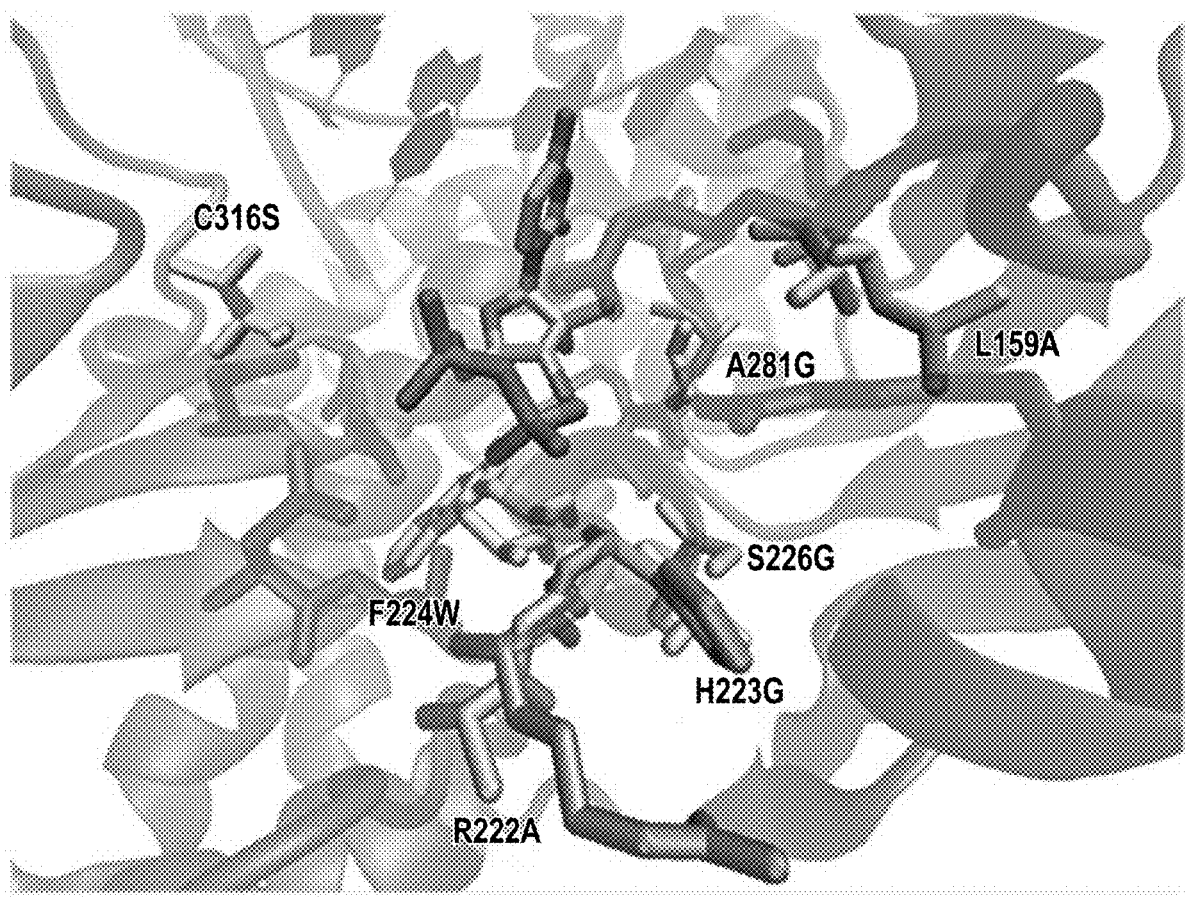

13 Claims, 9 Drawing Sheets
Specification includes a Sequence Listing.

(56) References Cited

OTHER PUBLICATIONS

Murakami et al. Investigating the effects of stereochemistry on incorporation and removal of 5-fluorocytidine analogs by mitochondrial DNA polymerase gamma: comparison of d- and I-D4FC-TP, Antiviral Research 62 (2004) 57-64.

Pan-Zhou et al., Differential Effects of Antiretroviral Nucleoside Analogs on Mitochondrial Function in HepG2 Cells, Antimicrobial Agents and Chemotherapy, 2000, p. 496-503.

Ray et al. Mechanism of Anti-Human Immunodeficiency Virus Activity of beta-D-6-Cyclopropylamino-2',3' Didehydro-2',3'-Dideoxyguanosine, Antimicrobial Agents and Chemotherapy, 2005, 1994-2001.

Sarto et al. 7-Deaza-7-fluoro-2'-C-methyladenosine inhibits Zika virus infection and viral-induced neuroinflammation, Antiviral Research 180 (2020) 104855.

Schinazi et al. Activities of 3'-Azido-3'-Deoxythymidine Nucleotide Dimers in Primary Lymphocytes Infected with Human Immunodeficiency Virus Type 1, Antimicrobial Agents and Chemotherapy, 1990, 1061-1067.

Shan et al. Zika Virus: Diagnosis, Therapeutics, and Vaccine, ACS Infect. Dis. 2016, 2, 170-172.

Sommandossi et al. Comparison of Cytotoxicity of the (−)- and (+)-Enantiomer of 2',3'-Dideoxy-3'-Thiacytidyne in Normal Human Bone Marrow Progenitor Cells, Biochemical Pharmacology, vol. 44, No. 10. pp. 1921-1925, 1992.

Stuyver et al. Antiviral Activities and Cellular Toxicities of Modified 2',3'-Dideoxy-2',3'-Didehydrocytidine Analogues, Antimicrobial Agents and Chemotherapy, 2002, p. 3854-3860.

Yun et al. Zika virus: An emerging flavivirus, Journal of Microbiology (2017) vol. 55, No. 3, pp. 204-219.

| HCV Residue | JEV X-Ray (4HDG) | DENV (5DTO, Seq) | ZIKV Model (JEV) |
|---|---|---|---|
| 48 | Arg | Val (Arg) | V,R | Val (Arg) |
| 141 | Lys | Lys | Lys | Lys |
| 158 | Arg | Arg | Arg | Arg |
| 159 | Leu | Leu | Leu | Ala |
| 160 | Ile | Ile | Ile | Ile |
| 220 | Asp | Asp | Asp | Asp |
| 221 | Thr | Thr | Thr | Thr |
| 222 | Arg | Ala | Ala | Ala |
| 223 | His | Gly | Gly | Gly |
| 224 | Phe | Trp | Trp | Trp |
| 225 | Asp | Asp | Asp | Asp |
| 226 | Ser | Thr | Thr | Thr |
| 280 | Arg | Arg | Arg | Arg |
| 281 | Ala | Gly | Gly | Gly |
| 282 | Ser | Ser | Ser | Ser |
| 287 | Thr | Thr | Thr | Thr |
| 291 | Asn | Asn | Asn | Asn |
| 316 | Cys | Ser | Ser | Ser |
| 317 | Gly | Gly | Gly | Gly |
| 318 | Asp | Asp | Asp | Asp |
| 319 | Asp | Asp | Asp | Asp |

FIG. 1A

Uninfected Vero cells stained with 4G2 antibody

Zika Infected Vero cells stained with 4G2 antibody

ANTIVIRAL AGENTS AND NUCLEOSIDE ANALOGS FOR TREATMENT OF ZIKA VIRUS

CROSS-REFERENCE TO RELATED APPLICATIONS

This application is the National Stage of International Application No. PCT/US2017/023537 filed Mar. 22, 2017, which claims the benefit of U.S. Provisional Application No. 62/312,225 filed Mar. 23, 2016. The entirety of each of these applications is hereby incorporated by reference for all purposes.

STATEMENT REGARDING FEDERALLY SPONSORED RESEARCH OR DEVELOPMENT

This invention was made with government support under AI129607 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 16099US_ST25.txt. The text file is 2 KB, was created on Aug. 17, 2020, and is being submitted electronically via EFS-Web.

FIELD OF THE INVENTION

The present invention is directed to compounds, methods and compositions for treating or preventing infections by the Zika virus. The compounds include using certain small molecules, including nucleosides and monophosphate prodrugs thereof, preferably pyrimidine nucleosides, and sulfasalazine. The present application discloses how to prepare nucleoside derivatives, convert them to therapeutically relevant nucleotide prodrugs, and ultimately deliver corresponding nucleotide triphosphates to the Zika virus polymerase at therapeutically-relevant concentrations.

BACKGROUND OF THE INVENTION

Nucleoside analogs as a class have a well-established regulatory history, with more than 10 currently approved by the US Food and Drug Administration (US FDA) for treating human immunodeficiency virus (HIV), hepatitis B virus (HBV), and herpes simplex C virus (HSV). The challenge in developing antiviral therapies is to inhibit viral replication without injuring the host cell.

Zika Virus (ZIKV) is emerging mosquito-borne flavivirus that is transmitted by the *Aedes* genus. Human case reports of clinically diagnosed ZIKV infections include self-limiting acute febrile illnesses with fever, headache, myalgia and rash. Epidemiology studies point out to a widespread distribution of ZIKV in the northern half of Africa, as well as in many countries in Southeast Asia, including Malaysia, India, the Philippines, Thailand, Vietnam, Indonesia and Pakistan. In May 2015, the Pan American Health Organization (PAHO) issued an alert regarding the first confirmed Zika virus infection in Brazil. Since then, the virus has spread to much of South and Central America, and the Caribbean. The outbreak in Brazil led also to reports of Guillain-Barre syndrome and pregnant women giving birth to babies with birth defects and poor pregnancy outcomes. These events prompted new alerts from the Brazil Ministry of Health, the European Centre for Disease Prevention and Control, and CDC concerning the possible association of microcephaly with the recent outbreak of Zika virus infection. According to the CDC, no locally transmitted Zika cases have been reported in the continental United States, but cases have been reported in returning travelers. As of now, there is no drugs or vaccine to treat or prevent Zika virus disease.

In light of the fact that acquired ZIKV infections have reached alarming levels worldwide, and have significant and in some cases tragic effects on the effected patient, there remains a strong need to find new effective pharmaceutical agents to treat this disease, with agents that have low toxicity to the host. However, to date, there have been no effective agents to treat, cure, or prevent a ZIKV infection.

It would be advantageous to provide anti-ZIKV agents, compositions including these agents, and methods of treatment using these agents. The present invention provides such agents, compositions and methods.

SUMMARY OF THE INVENTION

The present invention provides compounds, methods and compositions for treating or preventing Zika virus (ZIKV) infection in a host. Representative Zika virus strains that can be treated include ArD127707, CHI2871014, Java, MR766, NC14-02042914-3220, ZIKV Hu/Tahiti/01u/2014NIID, KU501215.1 (PRVABC59) and HS2015BA01.

The methods involve administering a therapeutically or prophylactically-effective amount of at least one compound as described herein to treat or prevent an infection by, or an amount sufficient to reduce the biological activity of, a ZIKV infection. The pharmaceutical compositions include one or more of the compounds described herein, in combination with a pharmaceutically acceptable carrier or excipient, for treating a host with Zika virus. The formulations can further include at least one further therapeutic agent.

Based on homology studies between the HCV and the ZIKV polymerase, and modeling studies using compounds known to inhibit the HCV polymerase, Applicants have determined that certain pyrimidine and purine nucleosides can inhibit the ZIKV polymerase.

Pyrimidine and purine nucleosides are more effective when they are administered in the form of monophosphate prodrugs, as the rate limiting step in forming the active triphosphate is the production of the monophosphate. Sulfasalazine, which has the formula:

and sulfasalazine analogs can be used to treat, prevent, or reduce the biological activity of a ZIKV infection.

Chloroquine, and chloroquine analogs can also be used to treat, prevent, or reduce the biological activity of a ZIKV infection.

The compounds can be combined with one or more additional anti-Zika compounds, including entry inhibitors useful against various viral disorders, and BCX4430 (BioCryst), a viral RNA-dependent RNA polymerase (RdRp) inhibitor.

BRIEF DESCRIPTION OF THE DRAWINGS

FIG. 1A provides a table of all HCV RDRP residues within 6 Å of the incoming Sofosbuvir-diphosphate from crystal structure (4WTG) and their positional equivalent for JEV, DENV, and ZIKV homology model (derived from JEV) after structural alignment. Identical residues across the structures are highlighted in blue, similar residues are highlighted in green, and dissimilar residues are orange.

FIG. 1B is a 3D representation of the HCV RDRP active site showing the position of all residues near the incoming nucleotide. The RDRP backbone is provided as transparent grey ribbons, the RNA primer:template are rendered as gold cartoons, and the incoming Sofosbuvir-diphosphate is indicated. The residues in the active site are colored according to the table in FIG. 1A, and residue substitutions between HCV and ZIKV are indicated.

FIGS. 2A and 2B are charts showing the results of uninfected and Zika-infected Vero cells, respectively, stained with 4G2 antibody.

FIGS. 3A-D show the results of treatment of Zika-infected Vero cells with a compound of the formula:

at concentrations of 10 μM, 1 μM, 0.1 μM and 0.01 μM, respectively.

FIGS. 4A-D show the results of treatment of Zika-infected Vero cells with a compound of the formula:

at concentrations of 10 μM, 1 μM, 0.1 μM and 0.01 μM, respectively.

FIGS. 5A-H show the results of treatment of Zika-infected Vero cells with various compounds, all at a concentration of 10 μM.

FIGS. 6A-6C are charts showing the percent inhibition of Zika virus (% inhibition) versus the concentration of sulfasalazine (SSZ, μM) (FIG. 6A), or control 1 (FIG. 6B), or in combination (FIG. 6C).

DETAILED DESCRIPTION

ZIKV has a positive-sense, single-stranded RNA genome approximately 11 kilobases in length. The genome contains 5' and 3' untranslated regions flanking a single open reading frame (ORF) that encodes a polyprotein that is cleaved into three structural proteins: the capsid, premembrane/membrane, and envelope, and seven non-structural proteins (NS1, NS2A, NS2B, NS3, NS4A, 2K, NS4B and NS5). One of these proteins, NS5, possesses polymerase activity and is involved in the synthesis of double-stranded RNA from the single-stranded viral RNA genome that serves as the template.

ZIKV replication may be prevented through the manipulation of NS5B's polymerase activity via competitive inhibition of NS5B protein. Alternatively, a chain-terminator nucleoside analog also may be incorporated into the extending RNA strand.

Nucleoside derivatives and modified monophosphate prodrug analogs described herein show inhibitory activity against Zika virus. Therefore, the compounds can be used to treat or prevent a viral infection in a host, or reduce the biological activity of the virus. The host can be a mammal, and in particular, a human, infected with Zika virus. Representative Zika virus strains that can be treated include ArD127707, CHI2871014, Java, MR766, NC14-02042914-3220, and ZIKV Hu/Tahiti/01u/2014NIID. The methods involve administering an effective amount of one or more of the nucleoside or nucleotides monophosphate prodrugs described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions.

I. Definitions

The terms "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a nucleotide composition that comprises at least approximately 95%, and, preferably, approximately 97%, 98%, 99% or 100% of a single enantiomer of that nucleotide.

As used herein, the term "substantially free of" or "substantially in the absence of" refers to a nucleotide composition that includes at least 85 to 90% by weight, preferably 95% to 98% by weight, and, even more preferably, 99% to 100% by weight, of the designated enantiomer of that nucleotide. In a preferred embodiment, the compounds described herein are substantially free of enantiomers.

Similarly, the term "isolated" refers to a nucleotide composition that includes at least 85 to 90% by weight, preferably 95% to 98% by weight, and, even more preferably, 99% to 100% by weight, of the nucleotide, the remainder comprising other chemical species or enantiomers.

In some cases, the phosphorus atom may be chiral herein termed "P*" or "P" which means that and that it has a designation of "R" or "S" corresponding to the accepted meanings of Cahn-Ingold-Prelog rules for such assignment. Prodrugs of Formula A may exist as a mixture of diastereomers due to the chirality at the phosphorus center. When chirality exists at the phosphorous center it may be wholly or partially Rp or Sp or any mixture thereof.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$ In the text, whenever the term C (alkyl range) is used, the term independently includes each member of that class as if specifically, and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds, and the term "lower alkenyl" includes $C_{2-6}$ alkenyl moieties. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds, and the term "lower alkynyl" includes $C_{2-6}$ alkynyl moieties. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl, including but not limited to methoxymethyl, aralkyl, including but not limited to benzyl, aryloxyalkyl, such as phenoxymethyl, aryl, including but not limited to phenyl, optionally substituted with halogen (F, Cl, Br, I), alkyl (including, but not limited to $C_1$, $C_2$, $C_3$, and $C_4$), alkoxy (including but not limited to $C_1$, $C_2$, $C_3$, and $C_4$), sulfonate esters, such as alkyl or aralkyl sulphonyl, including but not limited to methanesulfonyl, mono, di or triphosphate esters, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "peptide" refers to various natural or synthetic compounds containing two to one hundred amino acids linked by the carboxyl group of one amino acid to the amino group of another.

The term "pharmaceutically acceptable salt or prodrug" is used throughout the specification to describe any pharmaceutically acceptable form (such as an ester, phosphate ester, salt of an ester or a related group) of a nucleotide compound which, upon administration to a patient, provides the nucleotide monophosphate compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

Prodrugs also include amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterized by side-chain branching adjacent to the α-carbon atom, which showed improved bioavailability after oral administration compared with the alanine and glycine esters). A process for preparing such amino acid esters is disclosed in U.S. Pat. No. 4,957,924 (Beauchamp), the contents of which are incorporated by reference. As an alternative to the use of valine itself, a functional equivalent of the amino acid can be used (e.g., an acid halide such as the acid chloride, or an acid anhydride). In such a case, to avoid undesirable side-reactions, it may be advantageous to use an amino-protected derivative.

II. Active Compounds

In a first embodiment, the compounds have one of the following formulae:

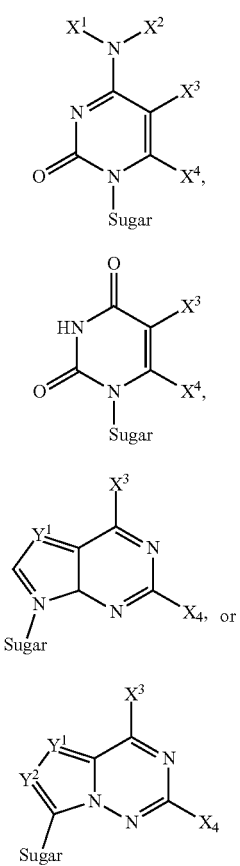

Formula A

Formula B

Formula C

Formula D wherein:
X$^1$ is H, C$_1$-C$_6$alkyl, C$_{3-8}$ cycloalkyl, C$_{3-8}$ cycloalkyl-C$_{1-6}$ alkyl, C$_1$-C$_6$haloalkyl, C$_1$-C$_6$alkoxy, C$_2$-C$_6$ alkenyl, C$_2$-C$_6$ alkynyl, COR$^1$, or COOR$^1$;

X$^2$ is hydrogen, C$_1$-C$_6$alkyl, C$_{3-8}$ cycloalkyl, C$_{3-8}$ cycloalkyl-C$_{1-6}$ alkyl, C$_1$-C$_6$haloalkyl, C$_1$-C$_6$alkoxy, C$_2$-C$_6$ alkenyl, C$_2$-C$_6$ alkynyl, —OH, COR$^1$, OCOR$^1$, COOR$^1$ or OCOOR$^1$;

each X$^3$ and X$^4$ is independently H, C$_{1-6}$ alkyl, C$_{2-6}$ alkenyl, C$_{2-6}$ alkynyl, aryl, alkylaryl, halogen (F, Cl, Br, I), NH$_2$, OH, SH, CN, or NO$_2$;

Y$^1$ and Y$^2$ are, independently, N, or C—X$^3$,

R$^1$ is independently CH$_2$—O(CO)—X$^5$; CH$_2$—O(CO)O—X$^5$, C$_{1-20}$ alkyl, the carbon chain derived from a fatty alcohol or C$_{1-20}$ alkyl substituted with a C$_1$-C$_6$ alkyl, C$_1$-C$_6$ alkoxy, di(C$_1$-C$_6$ alkyl)-amino, C$_{3-10}$ cycloalkyl, C$_{3-10}$ cycloalkyl alkyl, cycloheteroalkyl, aryl, heteroaryl, substituted aryl, or substituted heteroaryl; wherein the substituents are C$_{1-5}$ alkyl, or C$_{1-5}$ alkyl substituted with a C$_1$-C$_6$ alkyl, C$_1$-C$_6$ alkoxy, di(C$_1$-C$_6$ alkyl)-amino, C$_{3-10}$ cycloalkyl, or C$_{3-10}$ cycloalkyl alkyl;

X$^5$ is independently, C$_{1-20}$ alkyl, the carbon chain derived from a fatty alcohol or C$_{1-20}$ alkyl substituted with a C$_{1-6}$ alkyl, alkoxy, C$_{3-10}$ cycloalkyl, cycloalkyl alkyl, cycloheteroalkyl, aryl, heteroaryl, substituted aryl, or substituted heteroaryl; wherein the substituents are C$_{1-6}$ alkyl, or C$_{1-6}$ alkyl substituted with a C$_{1-6}$ alkyl, C$_{1-6}$ alkoxy, di(C$_{1-6}$ alkyl)-amino, or C$_{3-10}$ cycloalkyl, Sugar is of Formula (II):

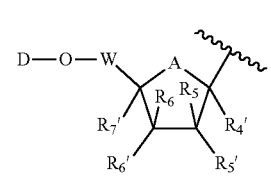

(II)

wherein:
W is CL$_2$ or CL$_2$CL$_2$, wherein L independently is selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl can each optionally contain one or more heteroatoms;

D is H, —C(O)R$^1$, —C(O)OR$^1$, —C(O)N(R$^1$)$_2$, —C(O)SR$^1$, —C(O)S(O)R$^1$, —C(O)SO$_2$R$^1$, —SOR$^1$, —SO$_2$R'—SO$_2$OR', —S(O)$_2$R$^1$, —S(O)$_2$N(R$^1$)$_2$, a diphosphate ester, a triphosphate ester, a phosphonate, a lipid, or stabilized phosphate prodrug;

R$^1$ is, independently, —CH$_2$—O(CO)—X$^5$; —CH$_2$—O(CO)O—X$^5$, C$_{1-20}$ alkyl, the carbon chain derived from a fatty alcohol or C$_{1-20}$ alkyl substituted with a C$_1$-C$_6$ alkyl, alkoxy, di(C$_1$-C$_6$ alkyl)-amino, C$_{3-10}$ cycloalkyl, cycloalkyl alkyl, cycloheteroalkyl, aryl, heteroaryl, substituted aryl, or substituted heteroaryl; wherein the substituents are C$_{1-6}$ alkyl, or C$_{1-6}$ alkyl substituted with a C$_1$-C$_6$ alkyl, C$_1$-C$_6$ alkoxy, di(C$_1$-C$_6$ alkyl)-amino, or C$_{3-10}$ cycloalky;

X$^5$ is independently, C$_{1-20}$ alkyl, the carbon chain derived from a fatty alcohol or C$_{1-20}$ alkyl substituted with a C$_1$-C$_6$ alkyl, alkoxy, C$_{3-10}$ cycloalkyl, cycloalkyl alkyl, cycloheteroalkyl, aryl, heteroaryl, substituted aryl, or substituted heteroaryl; wherein the substituents are C$_{1-6}$ alkyl, or C$_{1-6}$ alkyl substituted with a C$_1$-C$_6$ alkyl, C$_1$-C$_6$ alkoxy, di(C$_1$-C$_6$ alkyl)-amino, or C$_{3-10}$ cycloalkyl;

A is O, S, CH$_2$, CHF, CF$_2$, C=CH$_2$, C=CHF, or C=CF$_2$;

and R$^{7'}$ R$^{4'}$, R$^5$, R$^{5'}$, R$^6$, R$^{6'}$, and R$^{7'}$ are independently selected from the group consisting of H, F, Cl, Br, I, OH, SH, NH$_2$, NHOH, NHNH$_2$, N$_3$, C(O)OH, CN, CH$_2$OH, C(O)NH$_2$, C(S)NH$_2$, C(O)OR, R, OR, SR, SSR, NHR, and NR$_2$; with the proviso that there are not two NH$_2$, OH, and/or SH moieties on the same carbon atom;

R$^{5'}$ and R$^{6'}$ can come together to form a ring

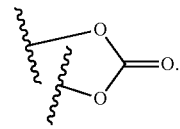 [SMILES: *OC(=O)O*]

In one embodiment, the compounds are of Formula A.
In another embodiment, the compounds are of Formula B.
In one embodiment, A is O.
In one embodiment, R$^{4'}$ and R$^{7'}$ are both H.
In one embodiment, R$^6$ or R$^{6'}$ is OH.
In one embodiment, X$^2$ is —OH, OCOR$^1$, or OCOOR$^1$.
In one embodiment, R$^5$ and R$^{5'}$, are methyl and OH.

In one embodiment, $R^5$ and $R^{5'}$, are methyl and F.
In one embodiment, $R^5$ and $R^{5'}$, are Cl and F.
In one embodiment, $R^5$ and $R^{5'}$, are Br and F.
In one embodiment, $R^5$ and $R^{5'}$, are Cl and Cl.
In one embodiment, $R^5$ and $R^{5'}$, are Br and Br.
In one embodiment, $R^5$ and $R^{5'}$, are F and F.

It is intended that each one or more of these specific definitions for the different substituents can be combined, and combinations of these specific definitions are intended to be within the scope of the invention.

In a second embodiment, the compounds are of one of the following formulae:

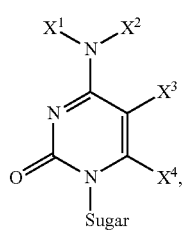

Formula A

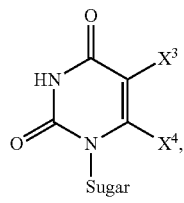

Formula B

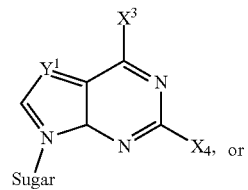

Formula C

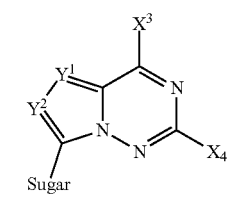

Formula D wherein:
$X^1$ is H, $C_1$-$C_6$alkyl, $C_{3-8}$ cycloalkyl, $C_{3-8}$ cycloalkyl-$C_{1-6}$ alkyl, $C_1$-$C_6$haloalkyl, $C_1$-$C_6$alkoxy, $C_2$-$C_6$ alkenyl, $C_2$-$C_6$ alkynyl, $COR^1$, or $COOR^1$;

$X^2$ is hydrogen, $C_1$-$C_6$alkyl, $C_{3-8}$ cycloalkyl, $C_{3-8}$ cycloalkyl-$C_{1-6}$ alkyl, $C_1$-$C_6$haloalkyl, $C_1$-$C_6$alkoxy, $C_2$-$C_6$ alkenyl, $C_2$-$C_6$ alkynyl, —OH, $COR^1$, $OCOR^1$, $COOR^1$ or $OCOOR^1$; each $X^3$ and $X^4$ is independently H, $C_{1-6}$ alkyl, $C_{2-6}$ alkenyl, $C_{2-6}$ alkynyl, aryl, alkylaryl, halogen (F, Cl, Br, I), $NH_2$, OH, SH, CN, or $NO_2$;

$Y^1$ and $Y^2$ are, independently, N, or C—$X^3$, $R^1$ is independently $CH_2$—O(CO)—$X^5$; $CH_2$—O(CO) O—$X^5$, $C_{1-20}$ alkyl, the carbon chain derived from a fatty alcohol or $C_{1-20}$ alkyl substituted with a $C_1$-$C_6$ alkyl, $C_1$-$C_6$ alkoxy, di($C_1$-$C_6$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_1$-$C_6$ alkyl, $C_1$-$C_6$ alkoxy, di($C_1$-$C_6$ alkyl)-amino, $C_{3-10}$ cycloalkyl, or $C_{3-10}$ cycloalkyl alkyl;

$X^5$ is independently, $C_{1-20}$ alkyl, the carbon chain derived from a fatty alcohol or $C_{1-20}$ alkyl substituted with a $C_{1-6}$ alkyl, alkoxy, $C_{3-10}$ cycloalkyl, cycloalkyl alkyl, cycloheteroalkyl, aryl, heteroaryl, substituted aryl, or substituted heteroaryl; wherein the substituents are $C_{1-6}$ alkyl, or $C_{1-6}$ alkyl substituted with a $C_{1-6}$ alkyl, $C_{1-6}$ alkoxy, di($C_{1-6}$ alkyl)-amino, or $C_{3-10}$ cycloalkyl, and Sugar is of the general Formulas (III) or (IV):

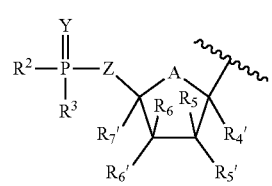

(III)

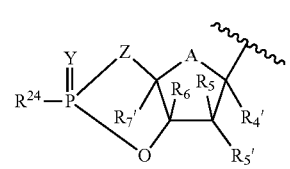

(IV)

wherein:

Y is O or S;

Z is selected from the group consisting of $CL_2$, $CL_2CL_2$, $CL_2OCL_2$, $CL_2SCL_2$, $CL_2O$, $OCL_2$ and $CL_2NHCL_2$, wherein L independently is selected from the group consisting of H, F, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl can each optionally contain one or more heteroatoms;

A is O, S, $CH_2$, CHF, $CF_2$, C=$CH_2$, C=CHF, or C=$CF_2$;

$R^{4'}$, $R^5$, $R^{5'}$, $R^6$, $R^{6'}$, and $R^{7'}$ are independently selected from the group consisting of H, F, Cl, Br, I, OH, SH, $NH_2$, NHOH, $NHNH_2$, $N_3$, C(O)OH, CN, $CH_2OH$, C(O)$NH_2$, C(S)$NH_2$, C(O)OR, R, OR, SR, SSR, NHR, and $NR_2$;

$R^{5'}$ and $R^{6'}$ can come together to form a ring

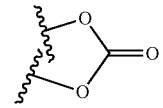 [SMILES: *OC(=O)O*]

wherein when A is O or S, $R^{7'}$ cannot be OH, SH, $NH_2$, NHOH, $NHNH_2$, OR, SR, SSR, NHR, or $NR_2$, and R is independently a $C_{1-6}$ alkyl, $C_{2-6}$ alkenyl, and $C_{2-6}$ alkynyl, $C_3$-$C_6$ cycloalkyl, aryl, alkylaryl, or arylalkyl, wherein the groups are optionally substituted with one or more substituents as defined above, $R^{24}$ is selected from the group consisting of $OR^1$,

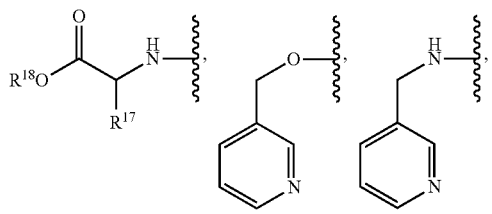

and fatty alcohols, $R^{15}$ is selected from the group consisting of H, Li, Na, K, phenyl and pyridinyl; wherein phenyl and pyridinyl are optionally substituted with one to three substituents independently selected from the group consisting of $(CH_2)_{0-6}CO_2R^{16}$ and $(CH_2)_{0-6}CON(R^{16})_2$;

$R^{17}$ is selected from those groups occurring in natural L-amino acids, $C_{1-6}$ alkyl, $C_{2-6}$ alkenyl, $C_{2-6}$ alkynyl, $C_3-C_6$ cycloalkyl, aryl, alkylaryl, or arylalkyl, wherein the groups are optionally substituted with one or more substituents as defined above, $R^{18}$ is H, $C_{1-20}$ alkyl, the carbon chain derived from a fatty alcohol or $C_{1-20}$ alkyl substituted with a $C_1-C_6$ alkyl, $C_1-C_6$ alkoxy, di($C_1-C_6$ alkyl)-amino, $C_{3-10}$ cycloalkyl, cycloalkyl alkyl, cycloheteroalkyl, aryl, heteroaryl, substituted aryl, or substituted heteroaryl; wherein the substituents are $C_{1-6}$ alkyl, or $C_{1-6}$ alkyl substituted with a $C_1-C_6$ alkyl, $C_1-C_6$ alkoxy, di($C_1-C_6$ alkyl)-amino, $C_{3-10}$ cycloalkyl, or cycloalkyl;

$R^2$ and $R^3$ are independently selected from the group consisting of.

(a) $OR^8$ where $R^8$ is H, Li, Na, K, $C_{1-20}$ alkyl, $C_{3-6}$ cycloalkyl, $C_{1-6}$ haloalkyl, aryl, or heteroaryl, optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{0-6}CO_2R^{9a}$, halogen, $C_{1-6}$ haloalkyl, —$N(R^{9a})_2$, $C_{1-6}$ acylamino, —$NHSO_2C_{1-6}$ alkyl, —$SO_2N(R^{9a})_2$, —$SO_2C_{1-6}$ alkyl, $COR^{9b}$, nitro, cyano and

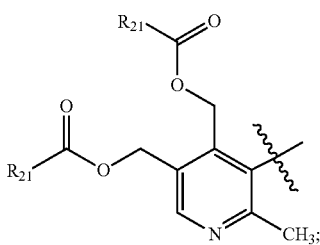

wherein
$R^{21}$ is as defined below;

$R^{9a}$ is independently H, $C_{1-20}$ alkyl, the carbon chain derived from a fatty alcohol or $C_{1-20}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl;

$R^{9b}$ is —$OR^9a$ or —$N(R^{9a})_2$;

(b)

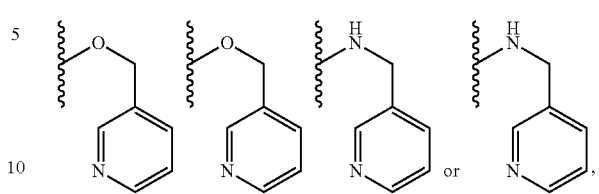

(c)

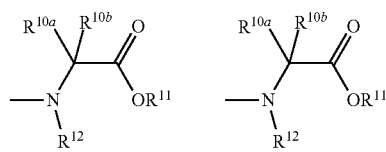

where $R^{10a}$ and $R^{10b}$ are:

(i) independently selected from the group consisting of H, $C_{1-10}$ alkyl, —$(CH_2)_rNR^{9a}_2$, $C_{1-6}$ hydroxyalkyl, —$CH_2SH$, —$(CH_2)_2S(O)\mu Me$, —$(CH_2)_3NHC(=NH)NH_2$, (1H-indol-3-yl)methyl, (1H-imidazol-4-yl)methyl, —$(CH_2)_mCOR^{9b}$, aryl and aryl-$C_{1-3}$ alkyl, wherein said aryl groups are optionally substituted with a group selected from the group consisting of hydroxyl, $C_{1-10}$ alkyl, $C_{1-6}$ alkoxy, halogen, nitro, and cyano;

(ii) $R^{10a}$ is H and $R^{10b}$ and $R^{12}$ together are $(CH_2)_{2-4}$ to form a ring that includes the adjoining N and C atoms;

(iii) $R^{10a}$ and $R^{10b}$ together are $(CH_2)_n$ to form a ring;

(iv) $R^{10a}$ and $R^{10b}$ both are $C_{1-6}$ alkyl; or (v) $R^{10a}$ is H and $R^{10b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$—$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or $C_{3-10}$ cycloalkyl;

p is 0 to 2;
r is 1 to 6;
n is 4 or 5;
m is 0 to 3;

$R^{11}$ is H, $C_{1-10}$ alkyl, or $C_{1-10}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl;

$R^{12}$ is H or $C_{1-3}$ alkyl, or $R^{10a}$, or $R^{10b}$ and $R^{12}$ together are $(CH_2)_{2-4}$ so as to form a ring that includes the adjoining N and C atoms;

(d) an O attached lipid (including a phospholipid), an N or O attached peptide, an O attached cholesterol, or an O attached phytosterol;

(e) $R^2$ and $R^3$ can come together to form a ring

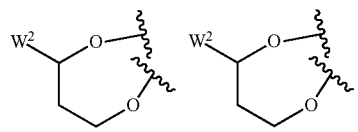

where W² is selected from the group consisting of phenyl or monocyclic heteroaryl, optionally substituted with one to three substituents independently selected from the group consisting of $C_{1-6}$ alkyl, $CF_3$, $C_{2-6}$ alkenyl, $C_{1-6}$ alkoxy, $OR^{9c}$, $CO_2R^{9a}$, $COR^9a$, halogen, $C_{1-6}$ haloalkyl, $—N(R^{9a})_2$, $C_{1-6}$ acylamino, $CO_2N(R^{9a})_2$, $SR^{9a}$, $—NHSO_2C_{1-6}$ alkyl, $—SO_2N(R^{9a})_2$, $—SO_2C_{1-6}$ alkyl, $COR^9b$, and cyano, and wherein said monocyclic heteroaryl and substituted monocyclic heteroaryl has 1-2 heteroatoms that are independently selected from the group consisting of N, O, and S, with the provisos that:

a) when there are two heteroatoms and one is O, then the other cannot be O or S, and b) when there are two heteroatoms and one is S, then the other cannot be O or S;

$R^{9a}$ is independently H or $C_{1-6}$ alkyl;

$R^{9b}$ is $—OR^{9a}$ or $—N(R^{9a})_2$;

$R^{9c}$ is H or $C_{1-6}$ acyl;

(f) $R^2$ and $R^3$ can come together to form a ring

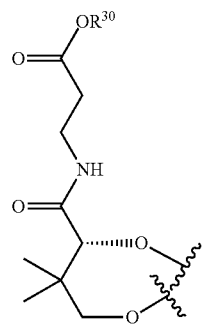

where $R^{30}$ is H, $C_{1-20}$ alkyl, $C_{1-20}$ alkenyl, the carbon chain derived from a fatty alcohol or $C_{1-20}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl;

(g)

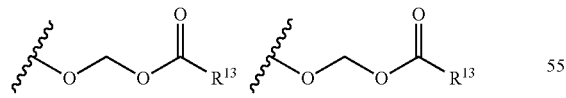

where $R^{13}$ is selected from the group consisting of H, $C_{1-10}$ alkyl, $C_{1-10}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl moiety; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl;

(h) $R^2$ and $R^3$ can come together to form a ring

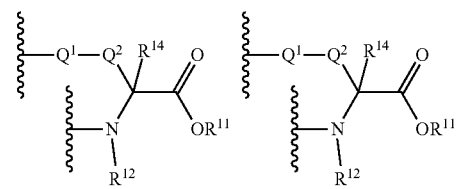

where $R^{14}$ is:

(i) independently selected from the group consisting of H, $C_{1-10}$ alkyl, $—(CH_2)_rNR_2^{9a}$, $C_{1-6}$ hydroxyalkyl, $—CH_2SH$, $—(CH_2)_2S(O)\mu Me$, $—(CH_2)_3NHC(=NH)NH_2$, (1H-indol-3-yl)methyl, (1H-imidazol-4-yl)methyl, $—(CH_2)_mCOR^{9b}$, aryl, aryl-$C_{1-3}$ alkyl, heteroaryl, and heteroaryl-$C_{1-3}$ alkyl, wherein said aryl and heteroaryl groups are optionally substituted with a group selected from the group consisting of hydroxyl, $C_{1-10}$ alkyl, $C_{1-6}$ alkoxy, halogen, nitro, and cyano;

(ii) $R^{14}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $—CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or $C_{3-10}$ cycloalkyl;

p is 0 to 2;

r is 1 to 6;

m is 0 to 3

$Q^1$ is $NR^9a$, O, or S $Q^2$ is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, fluoro, and chloro;

$R^{11}$ is H, $C_{1-10}$ alkyl, $C_{1-10}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl moiety; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl;

$R^{12}$ is H or $C_{1-3}$ alkyl, or $R^{14b}$ and $R^{12}$ together are $(CH_2)_{2-4}$ so as to form a ring that includes the adjoining N and C atoms;

(i) $R^2$ and $R^3$ can come together to form a ring selected from the group consisting of

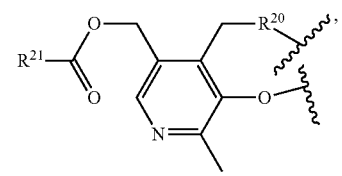

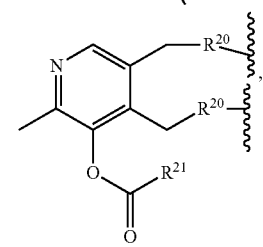

-continued

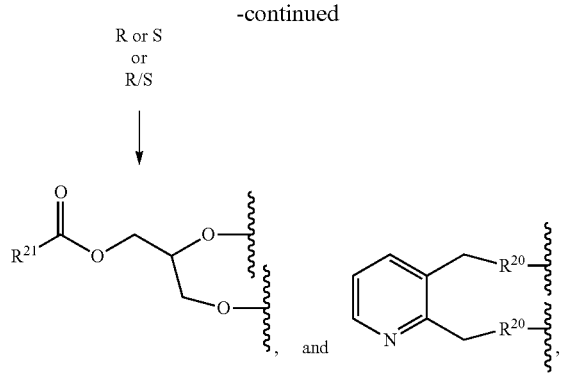

where $R^{20}$ is O or NH and
$R^{21}$ is selected from the group consisting of H, $C_{1-20}$ alkyl, $C_{1-20}$ alkenyl, the carbon chain derived from a fatty acid, and $C_{1-20}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl, and
(j) $R^2$ is a monophosphate ester or a diphosphate ester when $R^3$ is OH, $O^-K^+$, $O^-Li^+$, or $O^-Na^+$.

In one embodiment, the compounds are of Formula A.
In another embodiment, the compounds are of Formula B.
In another embodiment, the sugar is of Formula III.
In one aspect of this embodiment, $R^2$ is $OR^8$, where $R^8$ is aryl, optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{0-6}CO_2R^{9a}$, halogen, $C_{1-6}$ haloalkyl, —$N(R^{9a})_2$, $C_{1-6}$ acylamino, —$NHSO_2C_{1-6}$ alkyl, —$SO_2N(R^{9a})_2$, —$SO_2C_{1-6}$ alkyl, $COR^{9b}$, nitro, cyano and

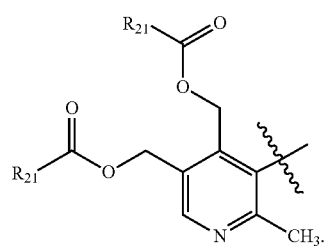

In another aspect of this embodiment, $R^3$ is

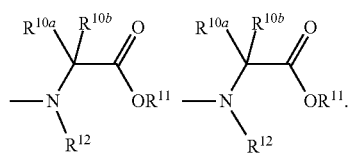

In one embodiment, A is O.
In one embodiment, $R^4$ and $R^7$ are both H.
In one embodiment, $R^6$ or $R^{6'}$ is OH.
In one embodiment, $X^2$ is —OH, $OCOR^1$, or $OCOOR^1$.
In one embodiment, $R^5$ and $R^{5'}$, are methyl and OH.
In one embodiment, $R^5$ and $R^{5'}$, are methyl and F.

In one embodiment, $R^5$ and $R^{5'}$, are Cl and F.
In one embodiment, $R^5$ and $R^{5'}$, are Br and F.
In one embodiment, $R^5$ and $R^{5'}$, are Cl and Cl.
In one embodiment, $R^5$ and $R^{5'}$, are Br and Br.
In one embodiment, $R^5$ and $R^{5'}$, are F and F.

It is intended that each one or more of these specific definitions for the different substituents can be combined, and combinations of these specific definitions are intended to be within the scope of the invention.

Specific active compounds include the following:

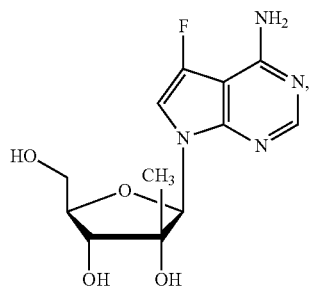

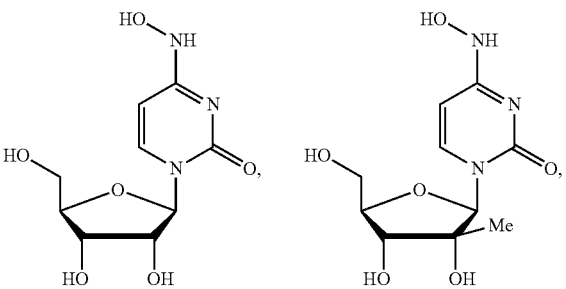

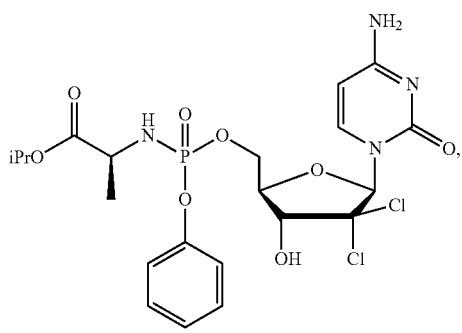

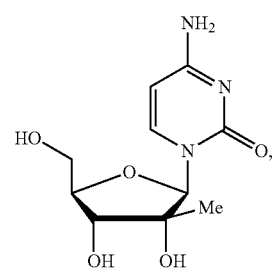

-continued
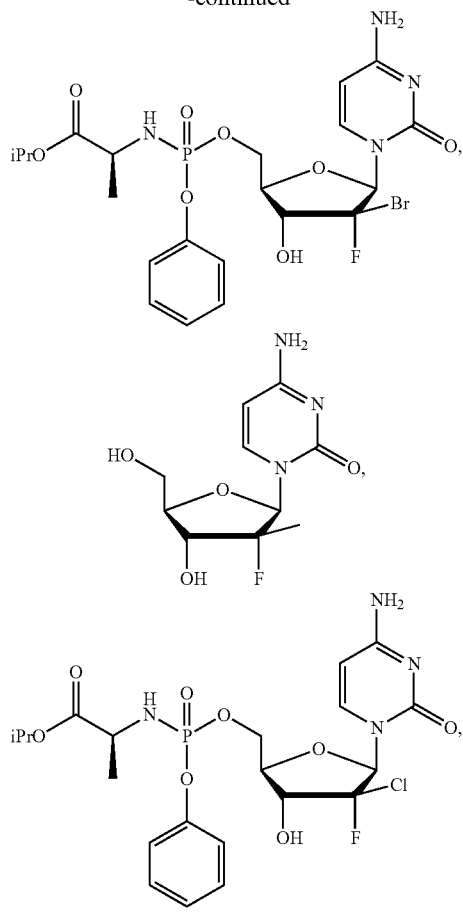
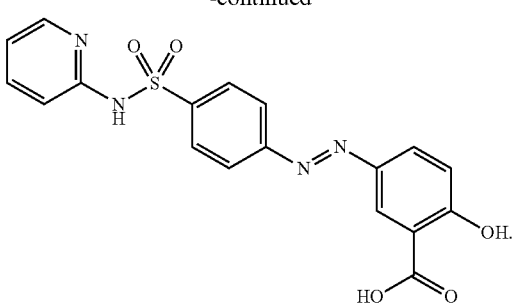
In one aspect of this second embodiment, the compound has the formula:
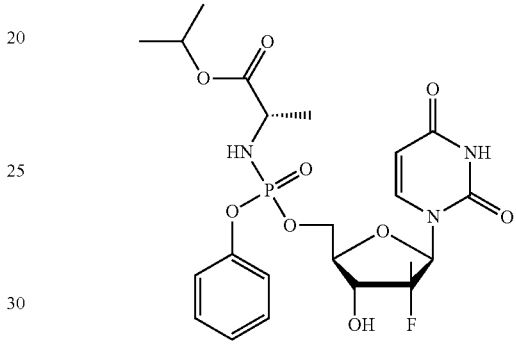
or is an analog of this compound where, at the 2'-position, the methyl is replaced with Cl, Br, or F.
In a third embodiment, the compounds are of one of the following formulae:
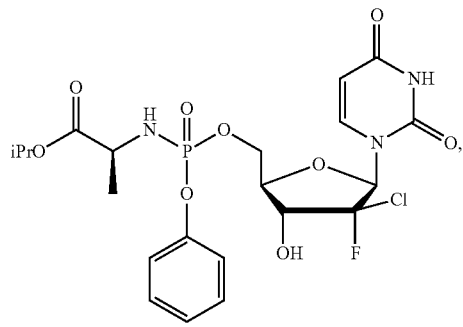
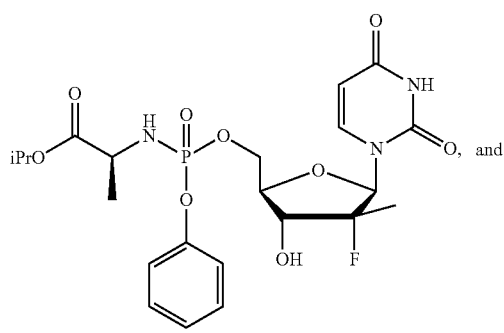
Formula A
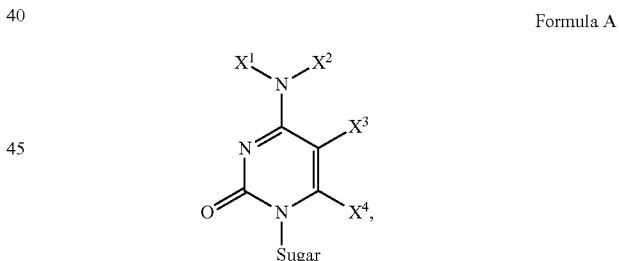
Formula B
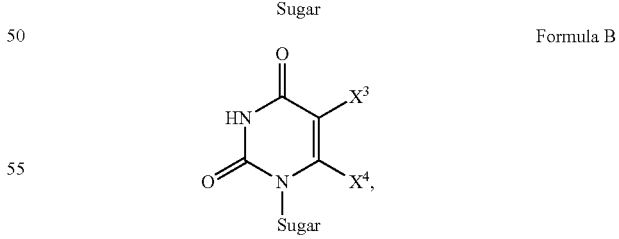
Formula C
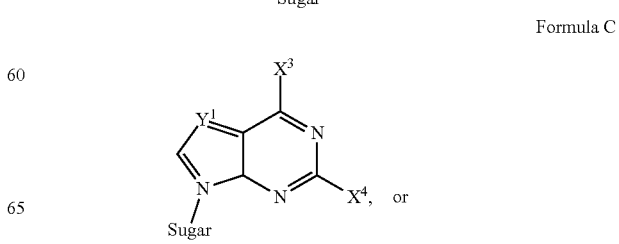
or -continued

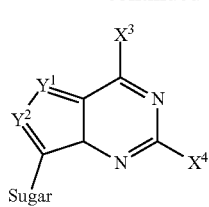

Formula D wherein:
X$^1$ is H, C$_1$-C$_6$alkyl, C$_{3-8}$ cycloalkyl, C$_{3-8}$ cycloalkyl-C$_{1-6}$ alkyl, C$_1$-C$_6$haloalkyl, C$_1$-C$_6$alkoxy, C$_2$-C$_6$ alkenyl, C$_2$-C$_6$ alkynyl, COR$^1$, or COOR$^1$;
X$^2$ is hydrogen, C$_1$-C$_6$alkyl, C$_{3-8}$ cycloalkyl, C$_{3-8}$ cycloalkyl-C$_{1-6}$ alkyl, C$_1$-C$_6$haloalkyl, C$_1$-C$_6$alkoxy, C$_2$-C$_6$ alkenyl, C$_2$-C$_6$ alkynyl, —OH, COR$^1$, OCOR$^1$, COOR$^1$ or OCOOR$^1$;
each X$^3$ and X$^4$ is independently H, C$_{1-6}$ alkyl, C$_{2-6}$ alkenyl, C$_{2-6}$ alkynyl, aryl, alkylaryl, halogen (F, Cl, Br, I), NH$_2$, OH, SH, CN, or NO$_2$;
Y$^1$ and Y$^2$ are, independently, N, or C—X$^3$,
R$^1$ is independently CH$_2$—O(CO)—X$^5$; CH$_2$—O(CO) O—X$^5$, C$_{1-20}$ alkyl, the carbon chain derived from a fatty alcohol or C$_{1-20}$ alkyl substituted with a C$_1$-C$_6$ alkyl, C$_1$-C$_6$ alkoxy, di(C$_1$-C$_6$ alkyl)-amino, C$_{3-10}$ cycloalkyl, C$_{3-10}$ cycloalkyl alkyl, cycloheteroalkyl, aryl, heteroaryl, substituted aryl, or substituted heteroaryl; wherein the substituents are C$_{1-5}$ alkyl, or C$_{1-5}$ alkyl substituted with a C$_1$-C$_6$ alkyl, C$_1$-C$_6$ alkoxy, di(C$_1$-C$_6$ alkyl)-amino, C$_{3-10}$ cycloalkyl, or C$_{3-10}$ cycloalkyl alkyl;
X$^5$ is independently, C$_{1-20}$ alkyl, the carbon chain derived from a fatty alcohol or C$_{1-20}$ alkyl substituted with a C$_{1-6}$ alkyl, alkoxy, C$_{3-10}$ cycloalkyl, cycloalkyl alkyl, cycloheteroalkyl, aryl, heteroaryl, substituted aryl, or substituted heteroaryl; wherein the substituents are C$_{1-6}$ alkyl, or C$_{1-6}$ alkyl substituted with a C$_{1-6}$ alkyl, C$_{1-6}$ alkoxy, di(C$_{1-6}$ alkyl)-amino, or C$_{3-10}$ cycloalkyl, and
Sugar is of the general Formula (V):

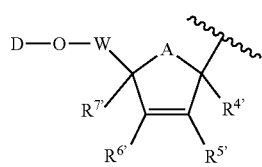

(V)

wherein:
D is H, C(O)R$^1$, C(O)OR$^1$, diphosphate ester, or triphosphate ester;
R$^1$ is independently C$_{1-20}$ alkyl, the carbon chain derived from a fatty alcohol or C$_{1-20}$ alkyl substituted with a C$_{1-6}$ alkyl, C$_{1-6}$ alkoxy, di(C$_{1-6}$ alkyl)-amino, C$_{3-10}$ cycloalkyl, C$_{3-10}$ cycloalkyl alkyl, cycloheteroalkyl, aryl, heteroaryl, substituted aryl, or substituted heteroaryl; wherein the substituents are C$_{1-5}$ alkyl, or C$_{1-5}$ alkyl substituted with a C$_1$-C$_6$ alkyl, C$_1$-C$_6$ alkoxy, di(C$_1$-C$_6$ alkyl)-amino, C$_{3-10}$ cycloalkyl, or C$_{3-10}$ cycloalkyl alkyl;
W is CL$_2$ or CL$_2$CL$_2$, wherein L independently is selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl can each optionally contain one or more heteroatoms;

A, R$^2$, R$^3$, Y, Z, R$^{4'}$, R$^{5'}$, R$^{6'}$, and R$^{7'}$ are as defined above;
wherein, when A is O or S, R$^{7'}$ cannot be OH, SH, NH$_2$, NHOH, NHNH$_2$, OR, SR, SSR, NHR, and NR$_2$,
wherein R is independently a C$_1$-C$_6$ alkyl, C$_{2-6}$ alkenyl, C$_2$-C$_6$ alkynyl, C$_3$-C$_6$ cycloalkyl, aryl, alkylaryl, or arylalkyl, wherein the groups are optionally substituted with one or more substituents as defined above, and
wherein, when A is O or CH$_2$, D is H or acyl, W is CH$_2$, R$^{4'}$ and R$^{7'}$ are H, then, R$^{5'}$ and R$^{6'}$ cannot be H, halogen, OH, SH, OCH$_3$, SCH$_3$, NH$_2$, NHCH$_3$, CH$_3$, CH=CH$_2$, CN, CH$_2$NH$_2$, CH$_2$OH, or COOH,
or the general Formula (VI):

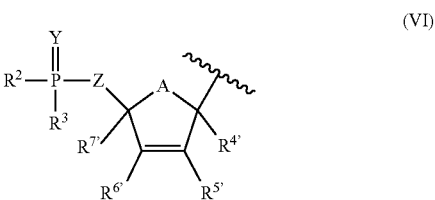

(VI)

wherein:
A, R$^2$, R$^3$, Y, Z, R$^{4'}$, R$^{5'}$, R$^{6'}$, and R$^{7'}$ are as defined above;
wherein, when A is O or S, R$^{7'}$ cannot be OH, SH, NH$_2$, NHOH, NHNH$_2$, OR, SR, SSR, NHR, or NR$_2$,
wherein R is independently a C$_1$-C$_6$ alkyl, C$_2$-C$_6$ alkenyl, C$_2$-C$_6$ alkynyl, C$_3$-C$_6$ cycloalkyl, aryl, alkylaryl, or arylalkyl, wherein the groups can optionally be substituted with one or more substituents as defined above,
or one of the general Formulas (VII), (VIII), (IX), and (X):

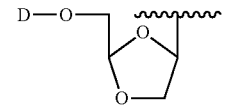

(VII)

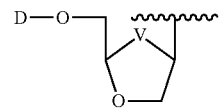

(VIII)

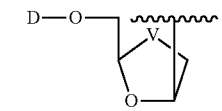

(IX)

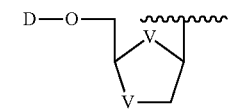

(X)

wherein:
D is H, C(O)R$^1$, C(O)OR$^1$, diphosphate ester, or triphosphate ester;
V is, individually, S or Se;
R$^1$ is independently C$_{1-20}$ alkyl, the carbon chain derived from a fatty alcohol or C$_{1-20}$ alkyl substituted with a C$_1$-C$_6$ alkyl, C$_1$-C$_6$ alkoxy, di(C$_1$-C$_6$ alkyl)-amino, C$_{3-10}$ cycloalkyl, C$_{3-10}$ cycloalkyl alkyl, cycloheteroalkyl, aryl, heteroaryl, substituted aryl, or substituted heteroaryl; wherein the substituents are C$_{1-5}$ alkyl, or C$_{1-5}$ alkyl substituted with a C$_1$-C$_6$ alkyl, C$_1$-C$_6$ alkoxy, di(C$_1$-C$_6$ alkyl)-amino, C$_{3-10}$ cycloalkyl, or C$_{3-10}$ cycloalkyl alkyl;

wherein D cannot be H or acyl, or one of the general formulas (XI), (XII), (XIII), and (XIV):

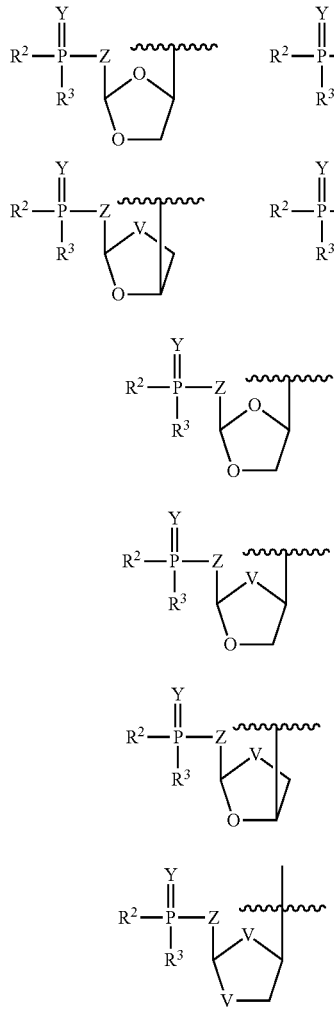

wherein:

V is, individually, S or Se;

$R^2$, $R^3$, Y, and Z are as defined above, or the general Formula (XV):

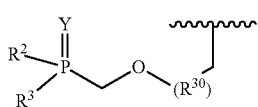

wherein:

$R^2$, $R^3$, and Y are as defined above; and $R^{30}$ is selected from the group consisting of $C_{1-20}$ alkyl, $C_{2-20}$ alkyl, $C_{2-20}$ alkenyl, $C_{2-20}$ alkynyl, $C_{3-10}$ cycloalkyl, aryl, heteroaryl, arylalkyl, and alkylaryl.

or one of the general Formulas (XVI) or (XVII):

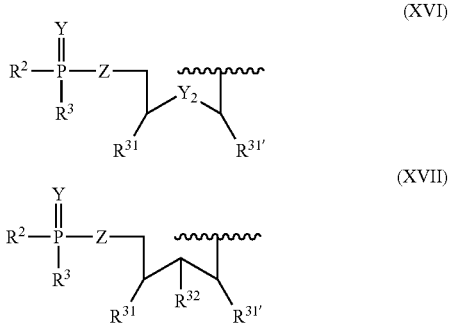

wherein:

$R^2$, $R^3$, Z, and Y are as defined above;

$Y^2$ is O, S, Se, or NR;

R is, independently, a $C_1$-$C_6$ alkyl, $C_2$-$C_6$ alkenyl, $C_2$-$C_6$ alkynyl, $C_3$-$C_6$ cycloalkyl, aryl, alkylaryl, or arylalkyl, wherein the groups are optionally substituted with one or more substituents as defined above, $R^{31}$, $R^{31'}$ and $R^{32}$ are H, $CH_3$, or $CH_2OR^{33}$; and $R^{33}$ is H or $C_1$-$C_6$ acyl, or the general Formula (XVIII)

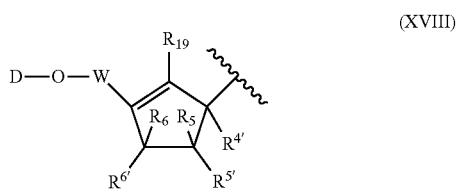

wherein:

D, W, $R^{4'}$, $R^5$, $R^{5'}$, $R^6$, and $R^{6'}$ are as defined above;

$R^{19}$ is H, F, Cl, Br, I, $N_3$, C(O)OH, CN, C(O)NH$_2$, C(S)NH$_2$, C(O)OR, or R;

wherein R is independently $C_1$-$C_6$ alkyl, $C_2$-$C_6$ alkenyl, $C_2$-$C_6$ alkynyl, $C_3$-$C_6$ cycloalkyl, aryl, alkylaryl, or arylalkyl, wherein the groups are optionally substituted with one or more substituents as defined above, wherein, when D is H or acyl, W is $CH_2$, $R^{4'}$ and $R^{19}$ are H, then, $R^5$, $R^{5'}$, $R^6$, $R^{6'}$ cannot be H, halogen, OH, SH, $OCH_3$, $SCH_3$, $NH_2$, $NHCH_3$, $CH_3$, $CH=CH_2$, CN, $CH_2NH_2$, $CH_2OH$, or COOH, or the general formula (XIX):

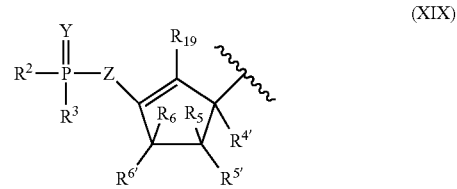

wherein:

$R^2$, $R^3$, $R^{4'}$, $R^5$, $R^{5'}$, $R^6$, and $R^{6'}$, Y and Z are as defined above, $R^{19}$ is H, F, Cl, Br, I, $N_3$, C(O)OH, CN, C(O)NH$_2$, C(S)NH$_2$, C(O)OR, or R, and wherein R is independently $C_1$-$C_6$ alkyl, $C_2$-$C_6$ alkenyl, $C_2$-$C_6$ alkynyl, $C_3$-$C_6$ cycloalkyl, aryl, alkylaryl, or arylalkyl, wherein the groups are optionally substituted with one or more substituents as defined above, or one of the Formulas (XX), (XXI), or (XXII):

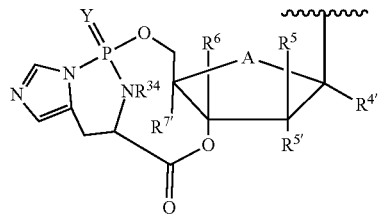
(XX)

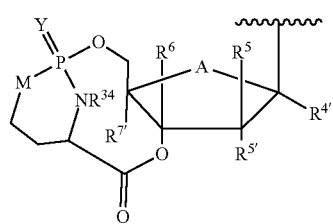
(XXI)

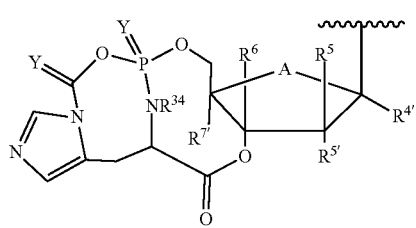
(XXII)

wherein:

A, $R^{4'}$, $R^5$, $R^{5'}$, $R^6$, Y, and $R^{7'}$ are as defined above;

$R^{34}$ is $C_1$-$C_6$ alkyl;

M is O, S, or NR;

wherein R is, independently, $C_1$-$C_6$ alkyl, $C_{2-6}$ alkenyl, $C_{2-6}$ alkynyl, $C_3$-$C_6$ cycloalkyl, aryl, alkylaryl, or arylalkyl, wherein the groups are optionally substituted with one or more substituents as defined above, or one of the Formulas (XXIII) or (XXIV):

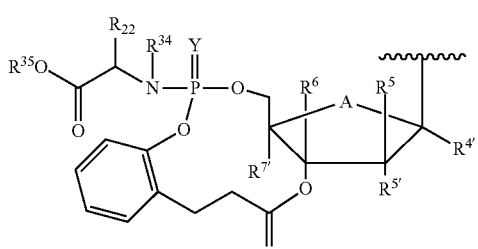
(XXIII)

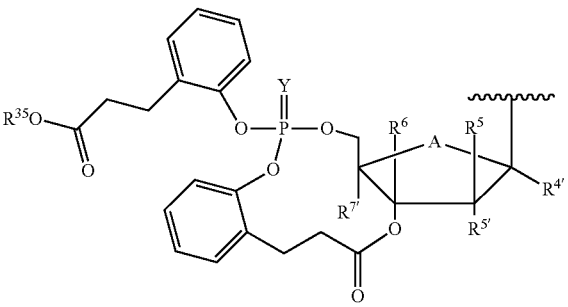
(XXIV)

wherein:

A, $R^{4'}$, $R^5$, $R^{5'}$, $R^6$, Y, $R^{34}$, and $R^{7'}$ are as defined above, $R^{35}$ is H, $C_{1-10}$ alkyl, $C_{1-10}$ alkyl substituted with a $C_{1-6}$ alkyl, $C_{1-6}$ alkoxy, di($C_{1-6}$ alkyl)-amino, $C_{3-10}$ cycloalkyl, $C_{3-10}$ cycloalkyl alkyl, cycloheteroalkyl, aryl, heteroaryl, substituted aryl, or substituted heteroaryl moiety; wherein the substituents are $C_{1-5}$ alkyl, or $C_{1-5}$ alkyl substituted with a $C_{1-6}$ alkyl, $C_{1-6}$ alkoxy, di($C_{1-6}$ alkyl)-amino, $C_{3-10}$ cycloalkyl, or $C_{3-10}$ cycloalkyl alkyl; and $R^{22}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'$-$OH)$-$Ph)$, $CH_2SH$, or $C_{3-6}$ cycloalkyl, or one of the Formulas (XXV) or (XXVI):

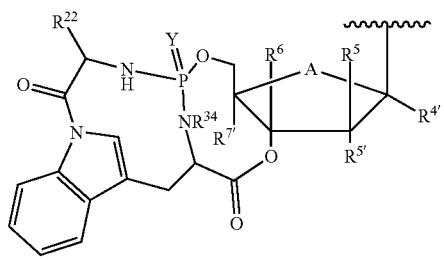
(XXV)

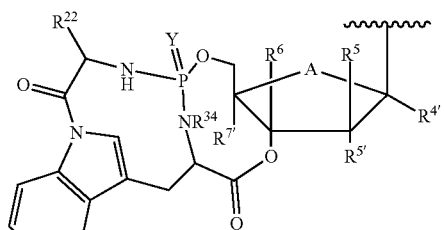
(XXVI)

wherein:

$R^{4'}$, $R^5$, $R^{5'}$, $R^6$, Y, $R^1$, $R^{22}$, $R^{34}$ and $R^{35}$ are as defined above.

In a fourth embodiment, the compound is sulfasalazine or a sulfasalazine analog:

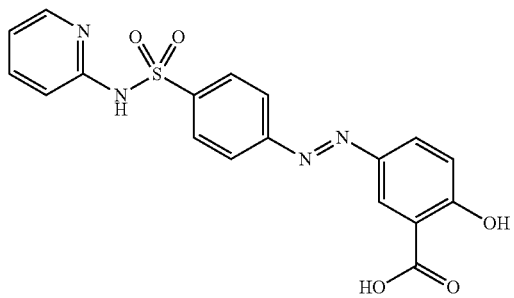 [SMILES: O=C(O)c1cc(/N=N/c2ccc(S(=O)(=O)Nc3ccccn3)cc2)ccc1O]

Sulfasalazine analogs include, but are not limited to, Ipsalazide, Balsalazine, and those disclosed in U.S. Pat. Nos. 4,849,416, 7,151,095. These analogs generally have the formula:

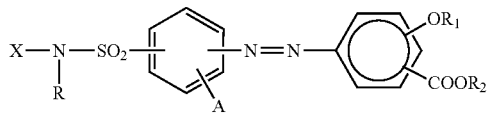

wherein

X is pyridyl, pheny, phenyl-substituted by lower alkyl, lower alkoxy, halogen, hydroxy, or nitro, furyl, pyrrolyl, quinolyl, pyrimidyl, thienyl or imidazolyl;

R, $R_1$ and $R_2$ are independently H, $C_{1-6}$ alkyl, $C_{1-6}$ aminoalkyl or

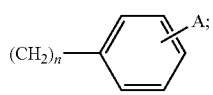

A is H, $C_{1-6}$ alkyl, $C_{1-6}$ aminoalkyl, amino, alkoxy, halo or $CF_3$; and n is 0 to 4.

In the formula: pyridyl means 2-pyridyl, 3-pyridyl and 4-pyridyl; halo means chloro, bromo, iodo, and fluoro groups; and amino means amino or an amino derivative such as $—NH_2$,

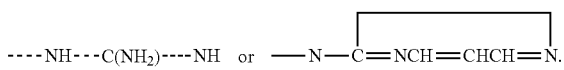

In a fifth embodiment, the compound is chloroquine or a chloroquine analog. Chloroquine (7-chloro-4-(4-diethylamino-1-methylbutylamino)quinolone), Hydroxychloroquine (7-chloro-4-(4-ethyl-(2-hydroxyethyl)-amino-1-methylbutylamino)quinolone), and amodiaquine are also effective anti-ZIKA agents, as are analogs of chloroquine. Examples of such analogs include those described in U.S. Pat. No. 6,479,504 and Solomon, V. R., et al. Design and synthesis of chloroquine analogs with anti-breast cancer property. Eur J Med Chem 45 (2010) 3916-3923. Representative chloroquine analogs include, but are not limited to:

Quinacrine;
7-hydroxy-4-(4-diethylamino-1-methylbutylamino)quinoline;
chloroquine phosphate;
7-chloro-4-(4-diethylamino-1-butylamino)quinoline (desmethylchloroquine);
7-hydroxy-4-(4-diethylamino-1-butylamino)quinoline;
7-chloro-4-(1-carboxy-4-diethylamino-1-butylamino)quinoline;
7-hydroxy-4-(1-carboxy-4-diethylamino-1-butylamino)quinoline;
7-chloro-4-(1-carboxy-4-diethylamino-1-methylbutylamino)quinoline;
7-hydroxy-4-(1-carboxy-4-diethylamino-1-methylbutylamino)quinoline;
7-hydroxy-4-(4-ethyl-(2-hydroxyethyl)-amino-1-methylbutylamino)quinoline; hydroxychloroquine phosphate;
7-chloro-4-(4-ethyl-(2-hydroxyethyl)-amino-1-butylamino)quinoline (desmethylhydroxychloroquine);
7-hydroxy-4-(4-ethyl-(2-hydroxyethyl)-amino-1-butylamino)quinoline;
7-chloro-4-(1-carboxy-4-ethyl-(2-hydroxyethyl)-amino-1-butylamino)quinoline;
7-hydroxy-4-(1-carboxy-4-ethyl-(2-hydroxyethyl)-amino-1-butylamino)quinoline;
7-chloro-4-(1-carboxy-4-ethyl-(2-hydroxyethyl)-amino-1-methylbutylamino)quinoline;
7-hydroxy-4-(1-carboxy-4-ethyl-(2-hydroxyethyl)-amino-1-methylbutylamino)quinoline;
8-[(4-aminopentyl)amino]-6-methoxydihydrochloride quinoline;
1-acetyl-1,2,3,4-tetrahydroquinoline;
8-[4-aminopentyl)amino]-6-methoxyquinoline dihydrochloride;
1-butyryl-1,2,3,4-tetrahydroquinoline;
7-chloro-2-(o-chlorostyryl)-4-[4-diethylamino-1-methylbutyl]aminoquiinolin e phosphate;
3-chloro-4-(4-hydroxy-α,α'-bis(2-methyl-1-pyrrolidinyl)-2,5-xyl idinoquinoline,
4-[(4-diethylamino)-1-methylbutyl)amino]-6-methoxyquinoline;
3,4-dihydro-1 (2H)-quinolinecarboxyaldehyde;
1,1'-pentamethylenediquinoleinium diiodide; and
8-quinolinol sulfate.

As with other compounds described herein, the compounds can exist in the form of diastereomeric mixtures, enantiomers and the like. Enantiomers of chloroquine and chloroquine analogs can be isolated, for example, according to the procedure of Stalcup, A. M. et al. (1996), Analytical Chemistry 68:2248-50.

In a sixth embodiment, the compound is an entry inhibitor. Several entry and/or adhesion factors, among which DC-SIGN, AXL, TYRO3, and to a lesser extent, TIM-1, permit ZIKV entry, with a major role for the TAM receptor AXL (Hamel et al., "Biology of ZIKA Virus Infection in Human Skin Cells," Journal of Virology, March 2016, volume 90, issue 6).

To date, numerous entry inhibitors are in various stages of preclinical development, including SP-30 (Samaritan Pharmaceuticals, Las Vegas, NV, USA), PRO 206 (Progenics, Tarrytown, NY, USA), and REP 9C (REPLICor, Laval, QC, Canada) and multiple early compounds identified by large-scale screening. Takebe et al. (Uenishi et al. "Identification of novel small molecule HCV entry inhibitor that acts through CD81," 15th International Symposium on Hepatitis C and Related Viruses. San Antonio, Texas 2008. Abstract #83: 64) recently performed an evaluation of 8,000 compounds for anti-HCV activity within the JFH-1 system and reported $EC_{50}$ values ranging from 53 to 113 nM across the top four hits, with encouraging toxicology data demonstrating $CC_{50}$ values of >35 µM.

Although the mechanism of action is not fully defined, it is believed that the anti-HCV activity is linked to interference with viral binding to the CD81 receptor. Although this study is in the early stages of development, it establishes the importance of CD81 in HCV infection and provides an excellent foundation for further studies designed to exploit the CD81 receptor as a target to inhibit viral replication.

Entry inhibitors for HIV infection which work through inhibition of DC-SIGN include those disclosed in Berzi, et al., (2012) A glycomimetic compound inhibits DC-SIGN-mediated HIV infection in cellular and cervical explant models. AIDS 26, 127-137, and in Mangold, et al., (2012) Quinoxalinoneinhibitors of the lectin DC-SIGN. Chem. Sci. 3, 772-777.

One entry inhibitor specific for HCV (Baldick et al., A Novel Small Molecule Inhibitor of Hepatitis C Virus Entry," PLoS Pathog. 2010 September; 6(9)), which can also have activity against ZIKV, has the following structure:

EI-1

$R = p\text{---}NO_2$

III. Stereoisomerism and Polymorphism

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective nucleoside, then derivatize the nucleoside to form the compounds described herein, or purify the nucleotides themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

The nucleotide prodrugs described herein can be administered to additionally increase the activity, bioavailability, stability or otherwise alter the properties of the nucleotide monophosphate.

A number of nucleotide prodrug ligands are known. In general, alkylation, acylation or other lipophilic modification of the monophosphate or other anolog of the nucleoside will increase the stability of the nucleotide.

Examples of substituent groups that can replace one or more hydrogens on the monophosphate moiety are alkyl, aryl, steroids, carbohydrates, including but not limited to sugars, 1,2-diacylglycerol and alcohols. Many are described in R. Jones & N. Bischofberger, *Antiviral Research,* 1995, 27, 1-17 and S. J. Hecker & M. D. Erion, *J. Med. Chem.,* 2008, 51, 2328-2345. Any of these can be used in combination with the disclosed nucleotides to achieve a desired effect.

The active nucleotide can also be provided as a 5'-phosphoether lipid as disclosed in the following references, which are incorporated by reference: Kucera, L. S., N. Iyer, E. Leake, A. Raben, Modest E. K., D. L. W., and C. Piantadosi, "Novel membrane-interactive ether lipid analogs that inhibit infectious HIV-1 production and induce defective virus formation," *AIDS Res. Hum. Retroviruses,* 1990, 6, 491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest, "Synthesis and evaluation of novel ether lipid nucleoside conjugates for anti-HIV activity," *J. Med. Chem.,* 1991, 34, 1408-14; Hostetler, K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3-deoxythymidine," *Antimicrob. Agents Chemother.,* 1992, 36, 2025-29; Hostetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.,* 1990, 265, 61127.

Nonlimiting examples of US Pat. that disclose suitable lipophilic substituents that can be covalently incorporated into the nucleoside, preferably at $R^2$ and/or $R^3$ position of the nucleotides described herein, or lipophilic preparations, include U.S. Pat. No. 5,149,794 (Yatvin et al.); U.S. Pat. No. 5,194,654 (Hostetler et al.), U.S. Pat. No. 5,223,263 (Hostetler et al.); U.S. Pat. No. 5,256,641 (Yatvin et al.); U.S. Pat. No. 5,411,947 (Hostetler et al.); U.S. Pat. No. 5,463,092 (Hostetler et al.); U.S. Pat. No. 5,543,389 (Yatvin et al.); U.S. Pat. No. 5,543,390 (Yatvin et al.); U.S. Pat. No. 5,543,391 (Yatvin et al.); and U.S. Pat. No. 5,554,728 (Basava et al.), all of which are incorporated by reference. Foreign patent applications that disclose lipophilic substituents that can be attached to nucleosites of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. Methods of Treatment

Hosts, including but not limited to humans, infected with Zika virus or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

VI. Combination or Alternation Therapy

In one embodiment, the compounds of the invention can be employed together with at least one other antiviral agent. Representative antiviral agents include entry inhibitors, reverse transcriptase inhibitors, protease inhibitors, and immune-based therapeutic agents.

For example, when used to treat or prevent Zika virus infection, the active compound or its prodrug or pharmaceutically acceptable salt can be administered in combination or alternation with another antiviral agent, including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

VII. Pharmaceutical Compositions

Hosts, including but not limited to humans, infected with ZIKV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 600 mg, preferably 70 to 600 mg of active ingredient per unit dosage form. An oral dosage of 5-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is that described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring.

Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions.

In one embodiment, the controlled release nanoparticulate formulations comprise a nanoparticulate active agent to be administered and a rate-controlling polymer which functions to prolong the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxy-poly-(glycidol), SA90HCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid) (PLGA)-nanoparticles are known to target the liver when given by intravenous (IV) or subcutaneously (SQ).

Because ZIKV can cause damage to, and is present in the liver, in one embodiment, the nanoparticles or other drug delivery vehicles are targeted to the liver. One such type of liver-targeted drug delivery vehicle is described in Park, et al., Mol Imaging. February 2011; 10(1): 69-77, and uses Glypican-3 (GPC3) as a molecular target. Park taught using this target for hepatocellular carcinoma (HCC), a primary liver cancer frequently caused by chronic persistent hepatitis.

In one aspect of this embodiment, this drug delivery vehicle is also used to target therapeutics to the liver to treat viral infections. Further, since the compounds described herein have anti-cancer uses, this type of system can target the compounds to the liver and treat liver cancers. GPC3 is a heparan sulfate proteoglycan that is not expressed in normal adult tissues, but significantly over-expressed in up to 80% of human HCC's. GPC3 can be targeted, for example, using antibody-mediated targeting and binding (See Hsu, et al., Cancer Res. 1997; 57:5179-84).

Another type of drug delivery system for targeting the liver is described in U.S. Pat. No. 7,304,045. The '045 patent discloses a dual-particle tumor or cancer targeting system that includes a first ligand-mediated targeting nanoparticle conjugated with galactosamine, with the ligand being on a target cell. The first nanoparticle includes poly(γ-glutamic acid)/poly(lactide) block copolymers and n antiviral compound, which in this case is a compound described herein, and in the '045 patent, was gancyclovir. A second nanoparticle includes poly(γ-glutamic acid)/poly(lactide) block copolymers, an endothelial cell-specific promoter, and a (herpes-simplex-virus)-(thymidine kinase) gene constructed plasmid, and provides enhanced permeability and retention-mediated targeting. The first and said second nanoparticles are mixed in a solution configured for delivering to the liver. When the disorder to be treated is a liver tumor or cancer, the delivery can be directly to, or adjacent to, the liver tumor or cancer.

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly (ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly (vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Nonionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675

A1, published on Jan. 31, 2002, for "Controlled Release Nanoparticulate Compositions," describes nanoparticulate compositions, and is specifically incorporated by reference.

The nanoparticle formulations including the compounds described herein, and also in the form of monophosphate prodrugs, and monophosphate, diphosphate, and triphosphate analogs, can be used to treat or prevent infections by flaviviruses, RSV, and influenza infections, and to treat or prevent certain types of cancers, including, but not limited to, liver cancer, acute myeloid leukemia, pancreatic cancer, lung cancer, ovarian cancer, colon cancer, rectal cancer, anal cancer, head and neck cancers, breast cancer, head and neck cancers, stomach cancer, some skin cancers, and other types of cancer described elsewhere herein that are treatable with anti-cancer nucleosides.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

IX. General Schemes for Preparing Active Compounds

The terms used in describing the invention are commonly used and known to those skilled in the art. As used herein, the following abbreviations have the indicated meanings:
aq aqueous
CDI carbonyldiimidazole
DMF N,N-dimethylformamide
DMSO dimethylsulfoxide
EDC 1-ethyl-3-(3-dimethyllaminopropyl)carbodiimide hydrochloride
EtOAc ethyl acetate
h hour/hours
HOBt N-hydroxybenzotriazole
M molar
mn minute
rt or RT room temperature
TBAT tetrabutylammonium triphenyldifluorosilicate
TBTU O-(Benzotriazol-1-yl)-N,N,N',N'-tetramethyluronium tetrafluoroborate
THF tetrahydrofuran Methods for the facile preparation of $N^4$-hydroxycytidine nucleosides derivatives, modified monophosphate and phosphonates prodrugs analogs are also provided. $N^4$-hydroxycytidine nucleosides derivatives, modified monophosphate and phosphonates prodrugs analogs disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

The syntheses of Sofosbuvir and numerous other NS5B polymerase inhibitors are well understood and need not be discussed further herein. Certain of the compounds described herein include di-halogenated substitution at the 2'-position, and certain others include prodrugs and/or non-ribose sugars not found in Sofosbuvir. Exemplary synthetic schemes are provided below.

The various reaction schemes are summarized below.

Scheme 1 is a non-limiting example of the synthesis of active compounds of the present invention, and in particular, a synthetic approach to monophosphate prodrugs XX, XXI, XXII.

Scheme 2 is a non-limiting example of the synthesis of active compounds of the present invention, and in particular, an alternate synthetic approach to monophosphate prodrugs XX, XXI, XXII.

Scheme 3 is a non-limiting example of the synthesis of active compounds of the present invention, and in particular, a synthetic approach to monophosphate prodrug XXIII.

Scheme 4 is a non-limiting example of the synthesis of active compounds of the present invention, and in particular, a synthetic approach to monophosphate prodrug XXIV.

Scheme 5 is a non-limiting example of the synthesis of active compounds of the present invention, and in particular, a synthetic approach to monophosphate prodrug XXV.

Scheme 6 is a non-limiting example of the synthesis of active compounds of the present invention, and in particular, an alternate synthetic approach to monophosphate prodrug XXV.

Scheme 7 is a non-limiting example of the synthesis of active compounds of the present invention, and in particular, a synthetic approach to monophosphate prodrug XXVI.

Scheme 8 is a non-limiting example of the synthesis of active compounds of the present invention, and in particular, an alternate synthetic approach to monophosphate prodrug XXVI.

Scheme 9 is a non-limiting example of the synthesis of active compounds of the present invention, and in particular, a synthetic approach to nucleosides 27.

Scheme 10 is a non-limiting example of the synthesis of active compounds of the present invention, and in particular, an alternate synthetic approach to nucleosides 27.

Scheme 11 is a non-limiting example of the synthesis of active compounds of the present invention, and in particular, a synthetic approach to nucleosides 29 and 30.

Scheme 12 is a non-limiting example of the synthesis of active compounds of the present invention, and in particular, an alternate synthetic approach to nucleosides 30.

Scheme 13 is a non-limiting example of the synthesis of active compounds of the present invention, and, in particular, a synthetic approach to monophosphate prodrug 35.

Scheme 14 is a non-limiting example of the synthesis of active compounds of the present invention, and, in particular, a synthetic approach to $N^4$-hydroxycytidine 2'-C-Me nucleoside 37.

Scheme 15 is a non-limiting example of the synthesis of active compounds of the present invention, and, in particular, a synthetic approach to $N^4$-hydroxycytidine 2'-deoxy-2'-α-fluoro-2'-β-C-Me nucleoside 39.

Scheme 16 is a non-limiting example of the synthesis of active compounds of the present invention, and, in particular, a synthetic approach to $N^4$-(Octanoyloxy)cytidine 2'-deoxy-2'-α-fluoro-2'-β-C-Me nucleoside 40.

Scheme 17 is a non-limiting example of the synthesis of active compounds of the present invention, and, in particular, a synthetic approach to $N^4$-hydroxycytidine 2'-C-Me nucleoside prodrug 44.

Scheme 18 is a non-limiting example of the synthesis of active compounds of the present invention, and, in particular, a synthetic approach to $N^4$-hydroxycytidine 2'-C-Me nucleoside prodrug 48.

Scheme 19 is a non-limiting example of the synthesis of active compounds of the present invention, and, in particular, a synthetic approach to $N^4$-hydroxycytidine 2'-deoxy-2'-α-fluoro-2'-3-C-Me nucleoside prodrug 51.

Scheme 20 is a non-limiting example of the synthesis of active compounds of the present invention, and, in particular, a synthetic approach to active compounds of the present invention, and, in particular, a synthetic approach to $N^4$-hydroxycytidine 2'-C-Me nucleoside prodrugs 54 and 56.

In one embodiment, nucleosides of formulas XX, XXI or XXII are prepared by protection of compound 1 by a group such as TIPS to provide 2 bearing a free alpha-hydroxyl group at the 3'-position of the sugar (Scheme 1). Preparation of compound 1 is accomplished by one of ordinary skill in the art, by methods outlined in: (a) Rajagopalan, P.; Boudinot, F. D; Chu, C. K.; Tennant, B. C.; Baldwin, B. H.; Antiviral Nucleosides: Chiral Synthesis and Chemotherapy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, GA, USA, pp: 319-37 d) Handbook of Nucleoside Synthesis: Vorbruggen H. & Ruh-Pohlenz C. John Wiley & sons 2001), and by general Schemes 9-10. Coupling of 2 with acids 3 or 4 can be accomplished by agents such as EDC, EDC/HOBt, TBTU, or CDI to give esters 5 or 6. After removal of protecting groups the resulting amino alcohols can be converted to the monophosphate prodrugs XX or XXI by exposure to phosphorous oxychloride or phosphorothioyl trichloride ($POCl_3$ or $PSCl_3$) or alternatively after water workup of the phosphorous oxychloride or phosphorothioyl trichloride reaction, a coupling agent such as DCC can be utilized in the formation of XX or XXI. Compound 7 can be obtained after water workup of the phosphorous oxychloride or phosphorothioyl trichloride reaction and subsequent exposure to phosgene or a phosgene equivalent such as CDI or triphosgene gives monophosphate prodrug XXII.

Scheme 1 A synthetic approach to monophostate prodrugs XX, XXI, XXII. (Base is a natural or unnatural nucleoside base; $R^{4'}$, $R^5$, $R^{5'}$, $R^6$, Y, M, $R^{34}$, and $R^{7'}$ are as defined in active compound section)

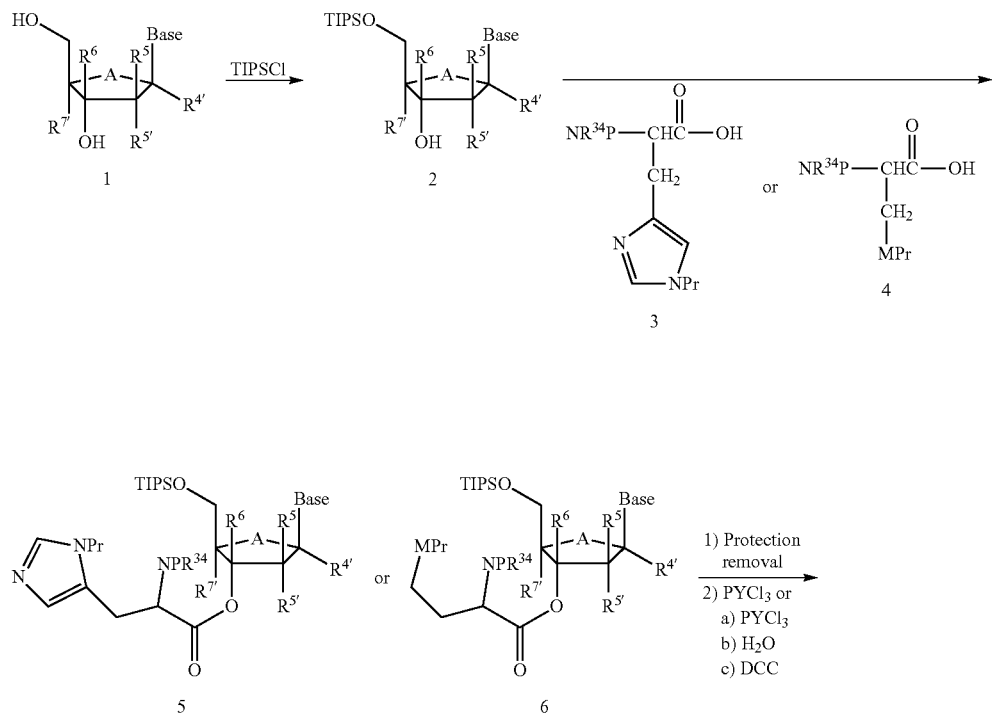

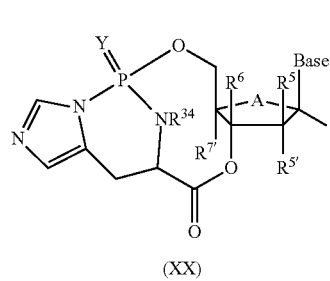

(XX)

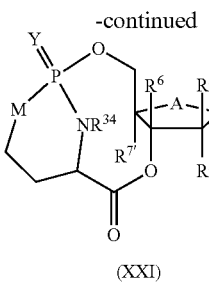

(XXI)

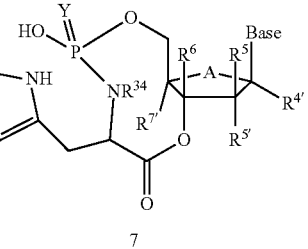

7 phosgene
thiophosgene
or equivalent

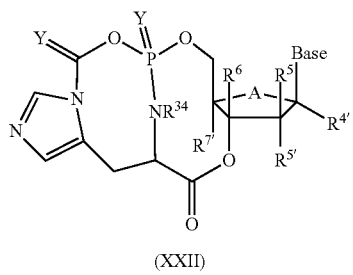

(XXII)

$R^{4'}, R^5, R^{5'}, R^6, R^{7'}$, and Base may contain stuitable protection; Pr = protection Alternatively, monophosphate prodrugs XX, XXI, XXII can be synthesized as outlined in Scheme 2, namely nucleoside 1 can be converted to the monophosphate, 8 directly by the action of phosphorous oxychloride or phosphorothioyl trichloride in trimethyl phosphate. Coupling to the amino esters 9 or 10 can be accomplished with standard coupling agents such as DCC to give phosphoramidates 7 and 11. Deprotection and subsequent coupling of 7 or 11 with agents such as EDC, EDC/HOBt, TBTU, or CDI provides monophosphate prodrugs XX and XXI. Monophosphate prodrug XXII can be obtained from 7 as described in Scheme 1.

Scheme 2 An alternate synthetic approach to monophostate prodrugs XX, XXI, XXII. (Base is a natural or unnatural nucleoside base; $R^{4'}, R^5, R^{5'}, R^6$, Y, M, $R^{34}$, and $R^{7'}$ are as defined in active compound section)

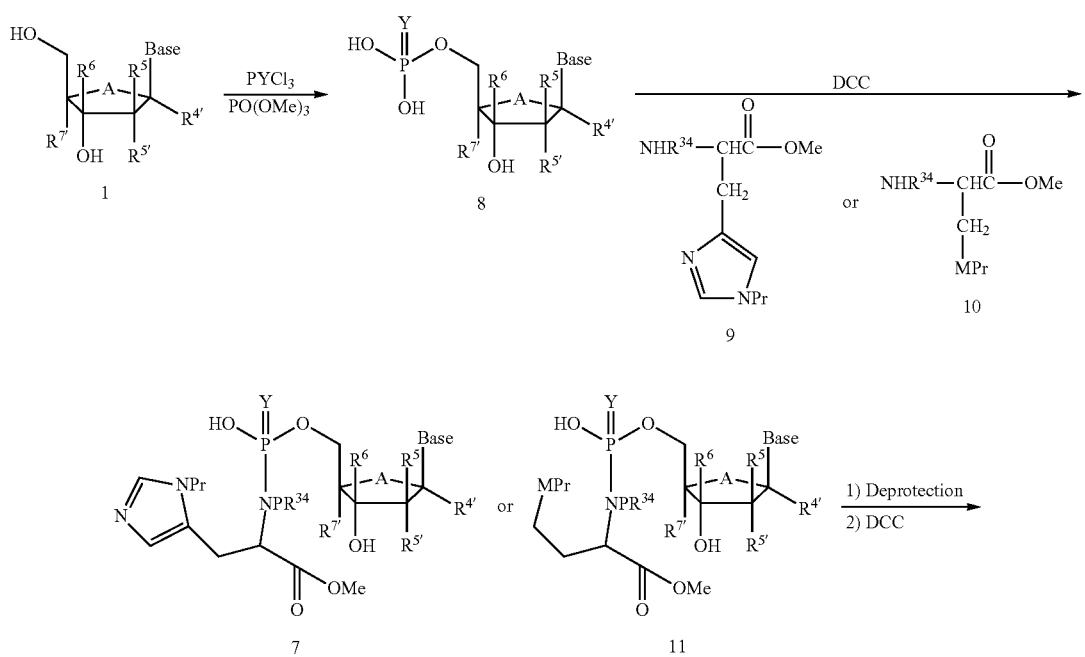

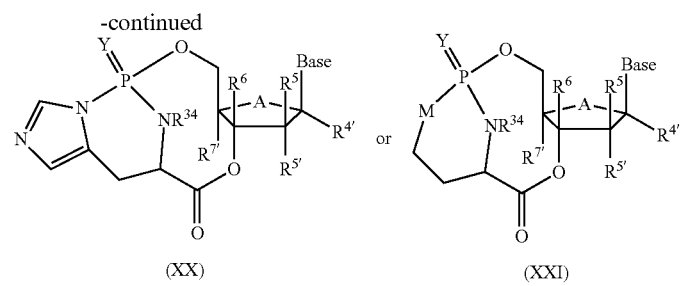

R⁴′, R⁵, R⁵′, R⁶, R⁷, and
Base may contain stuitable
protection; Pr = protection Monophosphate prodrug XXIII can be prepared as outlined in Scheme 3 starting from phenol 12 (Scheme 3). Exposure of 12 to phosphorous oxychloride or phosphorothioyl trichloride provides 13, which is subsequently allowed to react with an amino ester 14 to give phosphoramidate 15. Nucleoside 1 can next be converted to monophosphate analog 16 by reaction of the 5′-hydroxyl group with the chlorophosphorylamino propanoate, 15. Deprotection and subsequent coupling of 16 with agents such as EDC, EDC/HOBt, TBTU, or CDI provides monophosphate prodrugs XXIII.

Scheme 3 A synthetic approach to monophosphate prodrug XXIII. (Base is a natural or unnatural nucleoside base; R⁴′, R⁵, R⁵′, R⁶, Y, R³⁴, R³⁵, R²², and R⁷′ are as defined in active compound section)

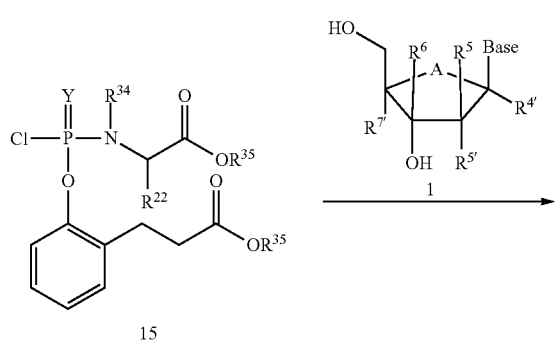

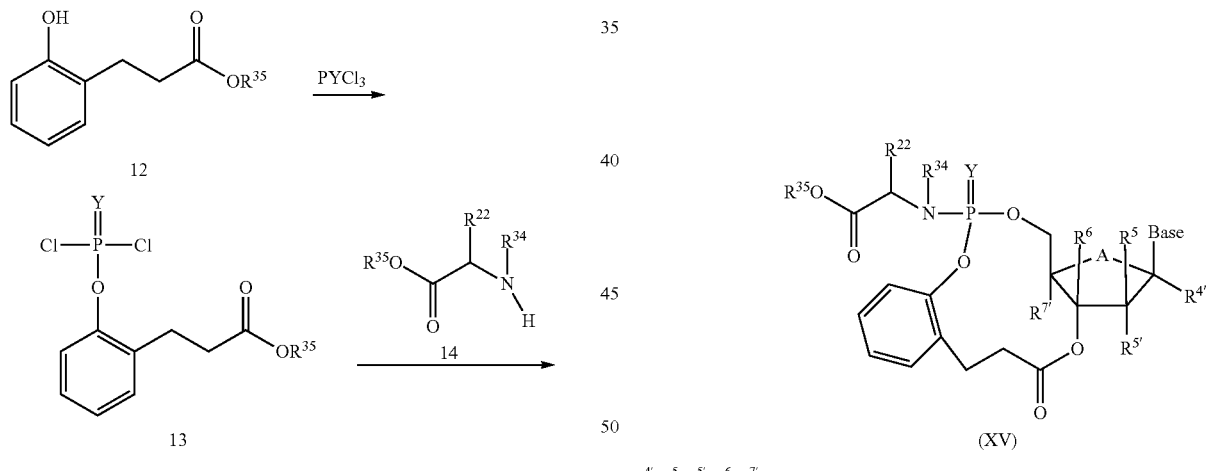

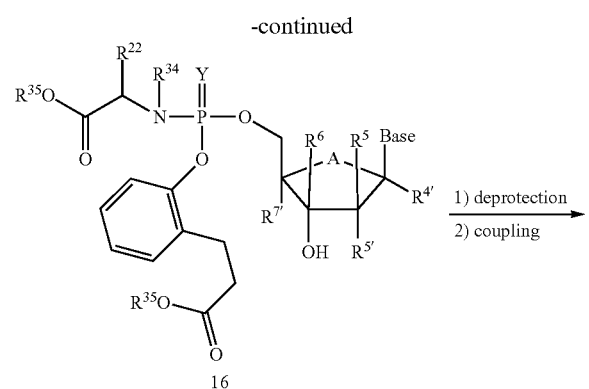

R⁴′, R⁵, R⁵′, R⁶, R⁷′, and Base may contain suitable protection

Monophosphate prodrug XXIV can be prepared by reaction of phenol 12 with phosphorous oxychloride or phosphorothioyl trichloride to provide diphenyl phosphorochloridate, 17 (Scheme 4). Nucleoside 1 can next be converted to an intermediate monophosphate analog by reaction of the 5′-hydroxyl group with the diphenyl phosphorochloridate, 17. Deprotection and subsequent ester formation with the 3′-hydroxyl group with agents such as EDC, EDC/HOBt, TBTU, or CDI followed by reesterification with R³⁵OH provides monophosphate prodrugs XXIV.

Scheme 4 A synthetic approach to monophosphate prodrug XXIV. (Base is a natural or unnatural nucleoside base; $R^{4'}$, $R^5$, $R^{5'}$, $R^6$, Y, $R^{35}$, and $R^{7'}$ are as defined in active compound section)

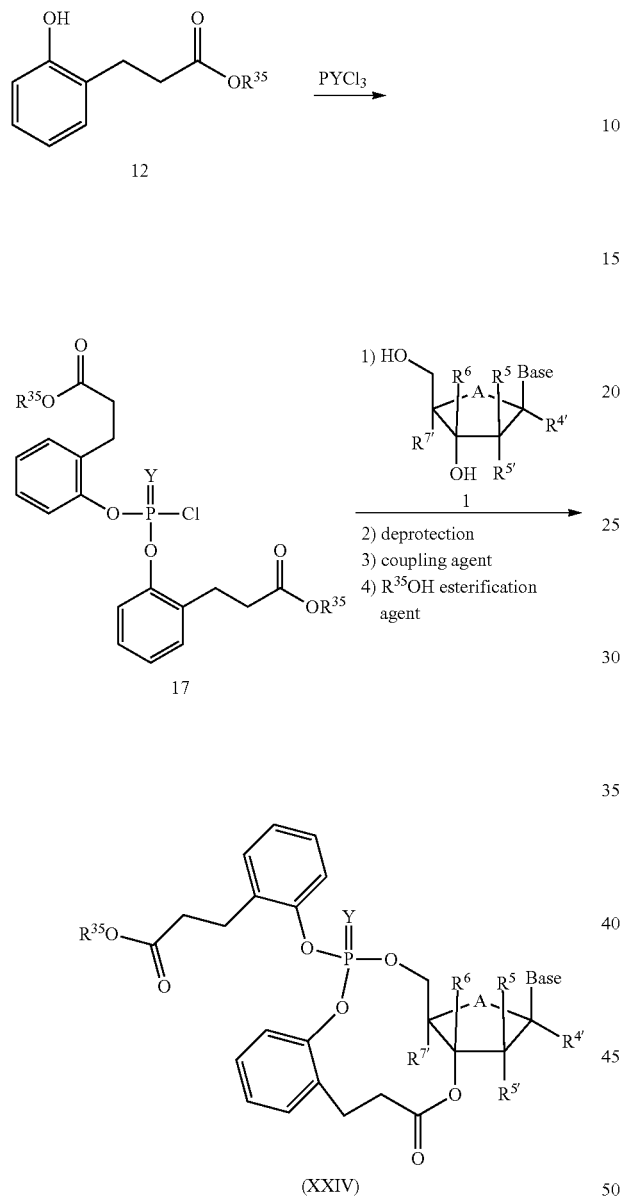

$R^{4'}$, $R^5$, $R^{5'}$, $R^6$, $R^{7'}$, and Base may contain suitable protection Scheme 5 A synthetic approach to monophosphate prodrug XXV. (Base is a natural or unnatural nucleoside base; $R^{4'}$, $R^5$, $R^{5'}$, $R^6$, Y, $R^{34}$, $R^{35}$, $R^{22}$, and $R^{7'}$ are as defined in active compound section)

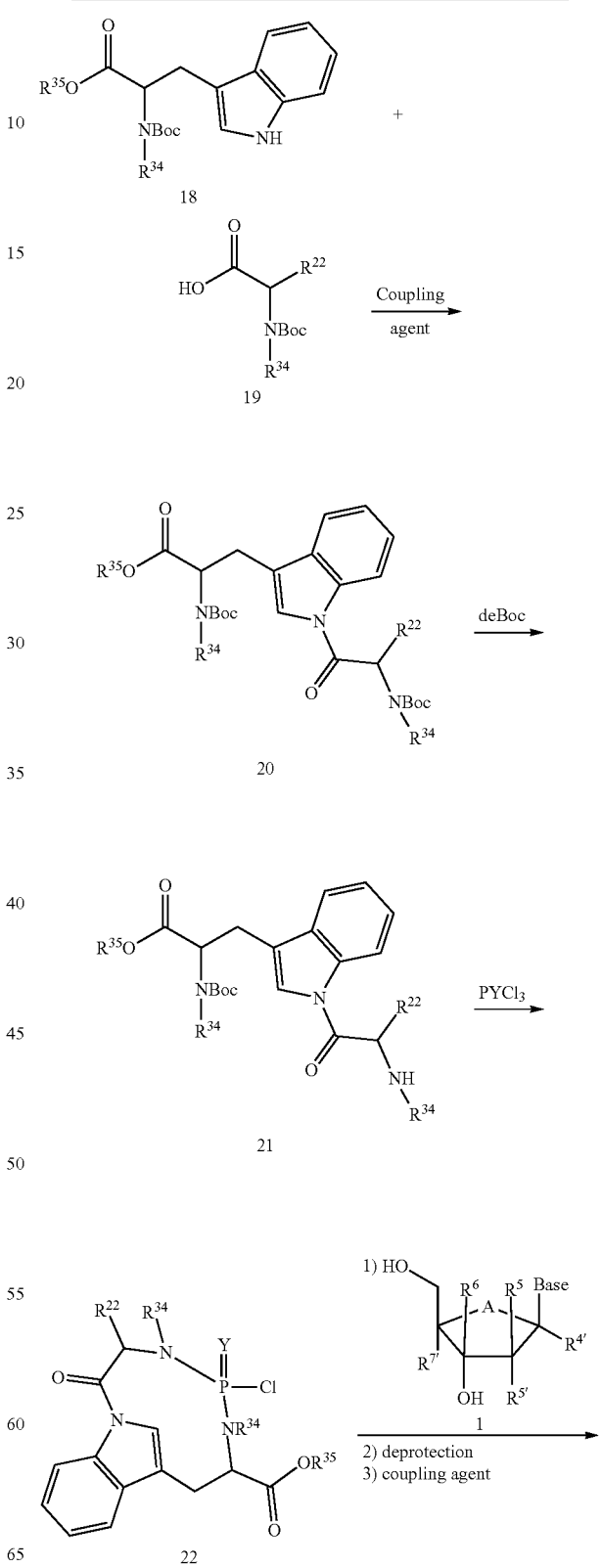

Monophosphate prodrug XXV can be prepared by initial reaction of protected tryptophan 18 with protected amino acid 19 with coupling agents such as EDC, EDC/HOBt, TBTU, or CDI to give dipeptide 20 (Scheme 5). Removal of the amine protections gives then diamine 21 which can then be reacted with phosphorous oxychloride or phosphorothioyl trichloride to give the cyclic phosphorodiamidic chloride, 22. Nucleoside 1 can next be converted to a monophosphate analog by reaction of the 5'-hydroxyl group with the cyclic phosphorodiamidic chloride, 22. Deprotection and subsequent coupling of 22 with agents such as EDC, EDC/HOBt, TBTU, or CDI provides monophosphate prodrugs XXV.

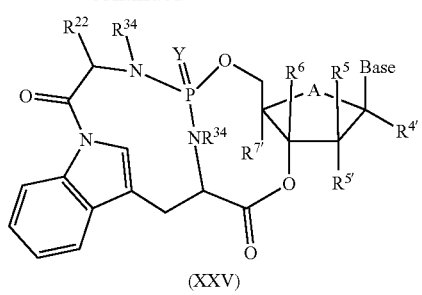

(XXV)

$R^{4'}, R^5, R^{5'}, R^6, R^{7'}$, and Base may contain suitable protection

Alternatively, monophosphate prodrug XXV can be prepared from monophosphate analog 8 followed by coupling with dipeptide 20 (Scheme 6).

Scheme 6 An alternate synthetic approach to monophosphate prodrug XXV. (Base is a natural or unnatural nucleoside base; $R^{4'}, R^5, R^{5'}, R^6$, Y, $R^{34}, R^{35}, R^{22}$, and $R^{7'}$ are as defined in active compound section)

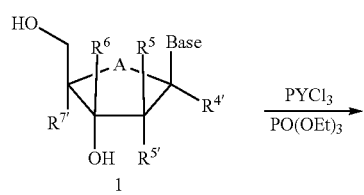

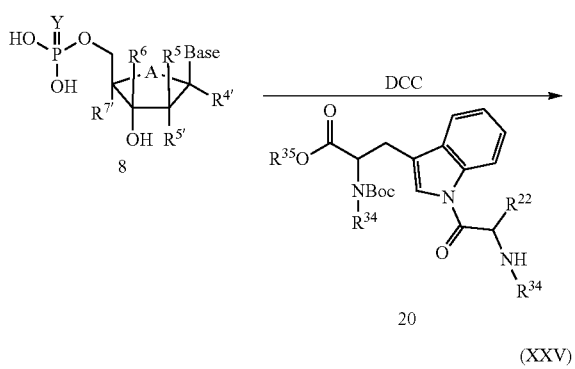

(XXV)

$R^{4'}, R^5, R^{5'}, R^6, R^{7'}$, and Base may contain suitable protection

Monophosphate prodrug XXVI can be prepared by initial reaction of phosphoramidic dichloride 23 with nucleoside 1 (Scheme 7). Subsequent reaction of the produced intermediate with water, hydrogen sulfide, or an amine provides monophosphate analog 24 (Scheme 7). Exposure of the bis nucleophile 24 to phosgene or a phosgene equivalent such as CDI provides monophosphate prodrugs XXVI.

Scheme 7 A synthetic approach to monophosphate prodrug XXVI. (Base is a natural or unnatural nucleoside base; $R^{4'}, R^5, R^{5'}, R^6$, Y, M, $R^{34}, R^{35}, R^{22}$, and $R^{7'}$ are as defined in active compound section)

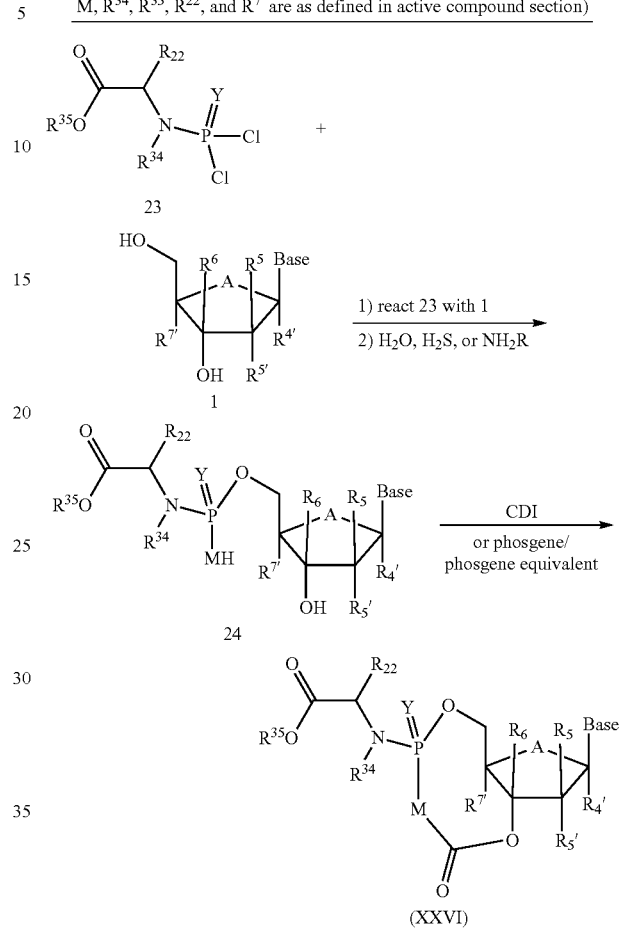

(XXVI)

$R^{4'}, R^5, R^{5'}, R^6, R^{7'}$, and Base may contain suitable protection

Alternatively, monophosphate prodrug XXVI (where M is not NR) can be prepared by initial reaction of nucleoside 1 with phosphorous oxychloride or phosphorothioyl trichloride as shown in Scheme 8. Subsequent reaction of the produced intermediate with water or hydrogen sulfide followed by reaction with phosgene or a phosgene equivalent such as CDI provides monophosphate prodrugs XXVI. (Scheme 8).

Scheme 8 An alternate synthetic approach to monophosphate prodrug XVIII. (Base is a natural or unnatural nucleoside base; $R^{4'}, R^5, R^{5'}, R^6$, Y, $R^{34}, R^{35}, R^{22}$, and $R^{7'}$ are as defined in active compound section)

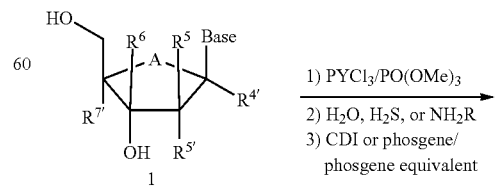

51

-continued

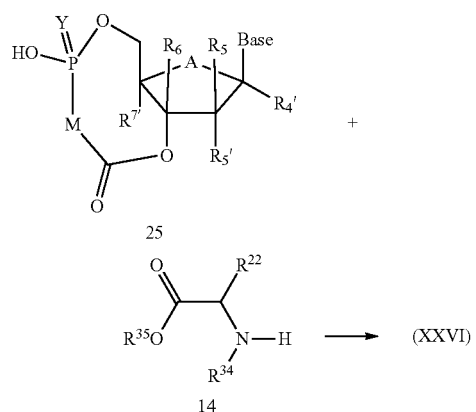

25

14

(XXVI)

$R^{4'}, R^5, R^{5'}, R^6, R^7$, and Base may contain suitable protection

Nucleoside 27 can be prepared by coupling sugar 26 with a protected or silylated pyrimidine base in the presence of Lewis acid such as TMSOTf. Deprotection of the 5'-hydroxyl gives nucleoside 27. (Scheme 9).

Scheme 9 A synthetic approach to nucleosides 27. ($R^{4'}, R^5, R^{5'}, R^6$, Y, A and $R^{7'}$ are as defined in active compound section)

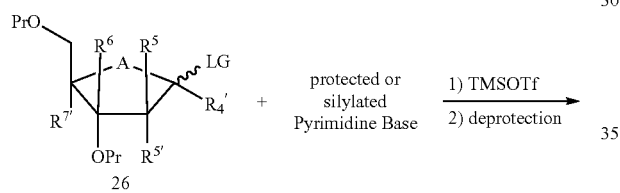

26

1) TMSOTf
2) deprotection protected or silylated Pyrimidine Base

27

$R^{4'}, R^5, R^{5'}, R^6, R^{6'}, R^7$, and Base may contain suitable protection;
Pr = protection; LG = OCOalkyl, OCOaryl, OCOalkylaryl; Y = $NH_2$ or OH Alternatively, nucleoside 27 can be prepared from 1'-halo or 1'-hydroxy compound 28. For the case of 1'-halo a protected or free pyrimidine base in the presence of a base such as triethyl amine or sodium hydride followed by deprotection would give nucleosides 27. For the case of 1'-hydroxy a protected or free pyrimidine base in the presence of a Mitsunobu coupling agent such as diisopropyl azodicarboxylate followed by deprotection would give nucleosides 27 (Scheme 10).

52

Scheme 10 An alternate synthetic approach to nucleosides 27. ($R^{4'}, R^5$, $R^{5'}, R^6$, Y, $R^{6'}$ and $R^{7'}$ are as defined in active compound section)

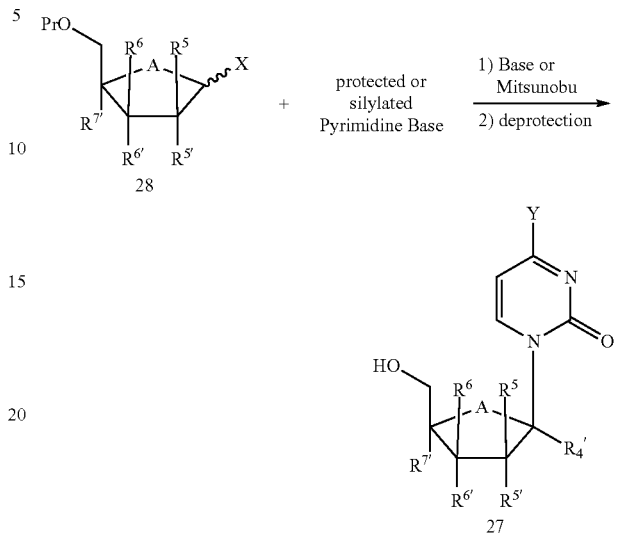

28 protected or silylated Pyrimidine Base

1) Base or Mitsunobu
2) deprotection

27

$R^{4'}, R^5, R^{5'}, R^6, R^{6'}, R^7$, and Base may contain suitable protection;
Pr = protection; X = halogen or OH; Y = $NH_2$ or OH $N^4$-hydroxycytidine nucleosides 29 can be prepared by reaction of compound 28 with hydroxylamine (Scheme 11). Subsequent reaction with various acid chlorides provides corresponding $N^4$-acyloxy derivatives 30.

Scheme 11 Synthetic approach to nucleosides 29 and 30. ($X^3, X^4, R^1$ and sugar are as defined in active compound section)

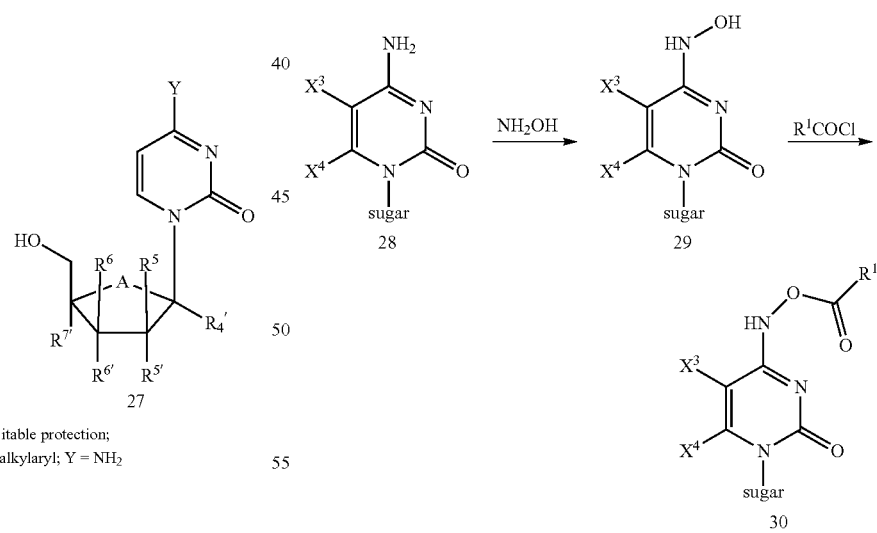

sugar may contain suitable protection

Alternatively, nucleoside 29 can be prepared by initial reaction of nucleoside 31 with phosphorous oxychloride and 1,2,4-triazole or methylimidazole as shown in scheme 12. Subsequent reaction of the produced intermediate with hydroxylamine followed by deprotection of the sugar moiety gives nucleoside 29.

Scheme 12 An alternate synthetic approach to nucleosides 29.
($X^3$, $X^4$, $R^1$ and sugar are as defined in active compound section)

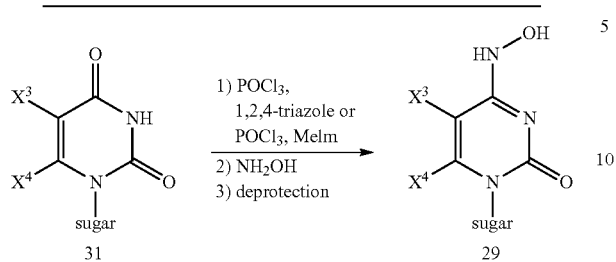

$X^3$, $X^4$ and sugar may contain suitable protection

Monophosphate prodrug 35 can be prepared by initial reaction of an appropriately protected hydroxylamine derivative with nucleoside 32 (Scheme 13). Subsequent reaction of 33 with phosphoramidate chloride 34 followed by necessary deprotection provides monophosphate prodrug 35.

Scheme 13 Approach to monophosphate prodrug 35. ($X^3$, $X^4$, Y, $R^{4'}$, $R^5$, $R^{5'}$, $R^6$, Y, $R^{34}$, $R^{35}$, $R^{22}$, and $R^{7'}$ are as defined in active compound section)

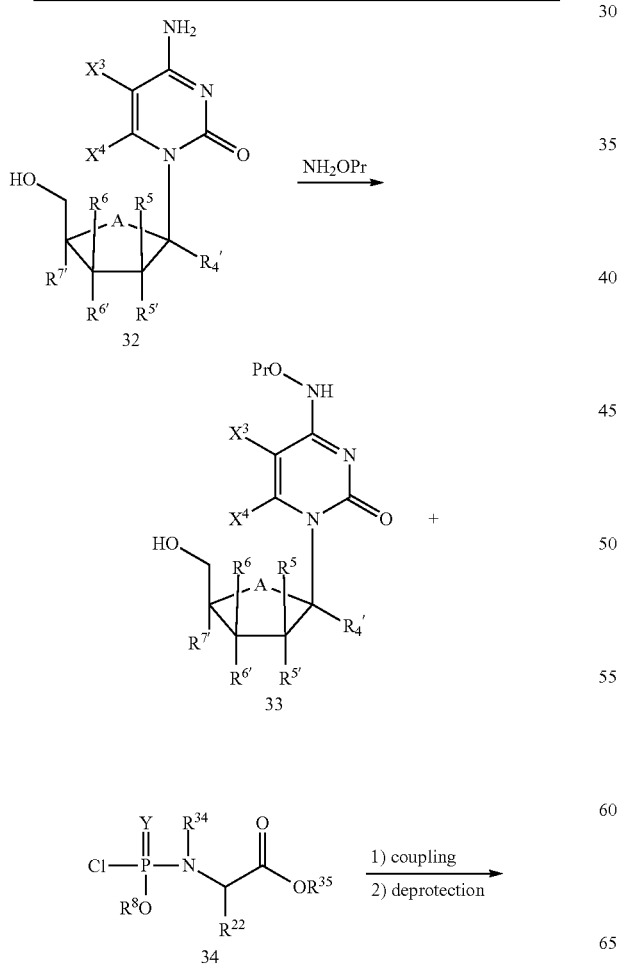

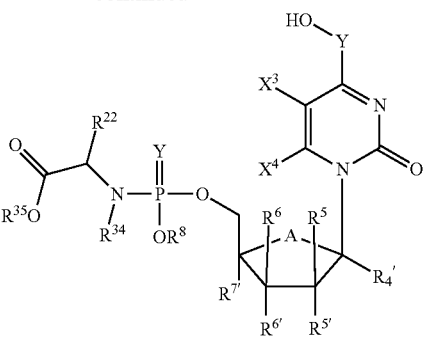

$X^3$, $X^4$, $R^{4'}$, $R^5$, $R^{5'}$, $R^6$, $R^{6'}$, $R^7$, $R^8$ may contain suitable protection; Pr = protection Scheme 14. Synthesis of $N^4$-hydroxycytidine 2'-C-Me nucleoside 37

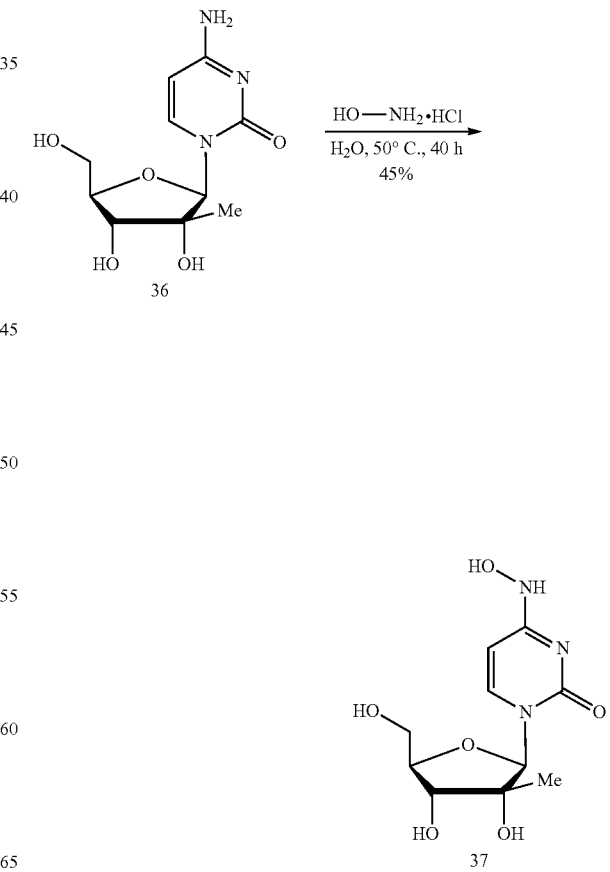

55
1-((2R,3R,4R,5R)-3,4-dihydroxy-5-(hydroxymethyl)-3-methyltetrahydrofuran-2-yl)-4-(hydroxyamino)pyrimidin-2(H)-one 37
56
1-((2R,3R,4R,5R)-3-fluoro-4-hydroxy-5-(hydroxymethyl)-3-methyltetrahydrofuran-2-yl)-4-((octanoyloxy)amino)pyrimidin-2(1H)-one 40
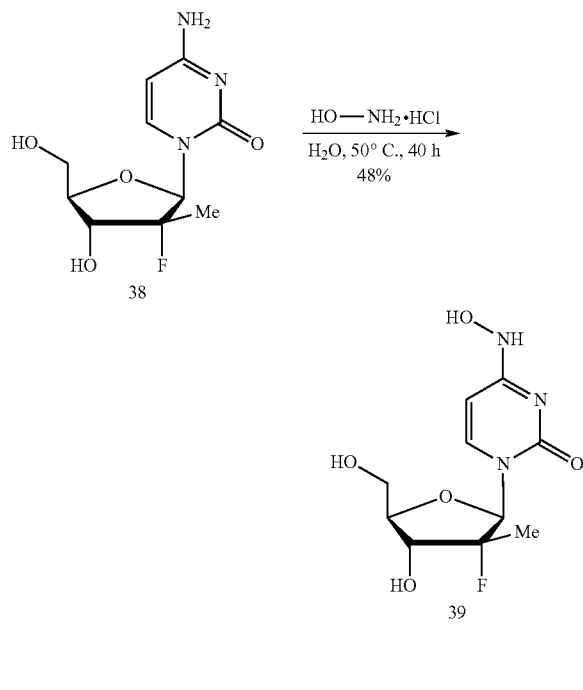
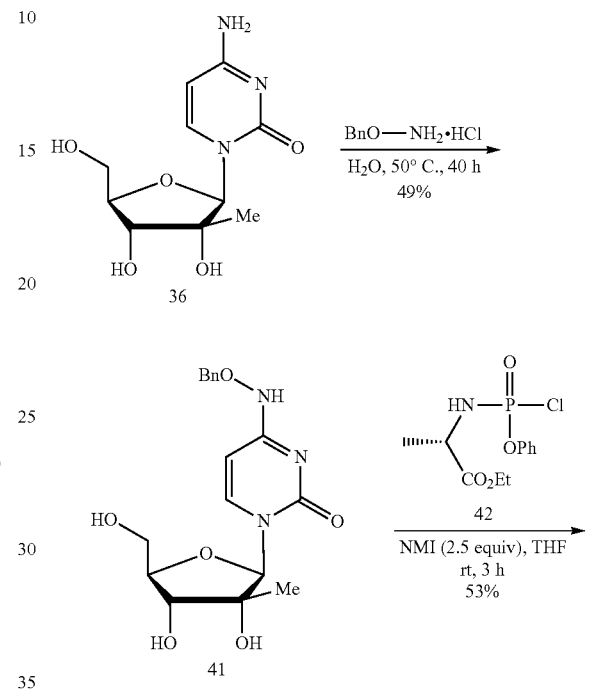
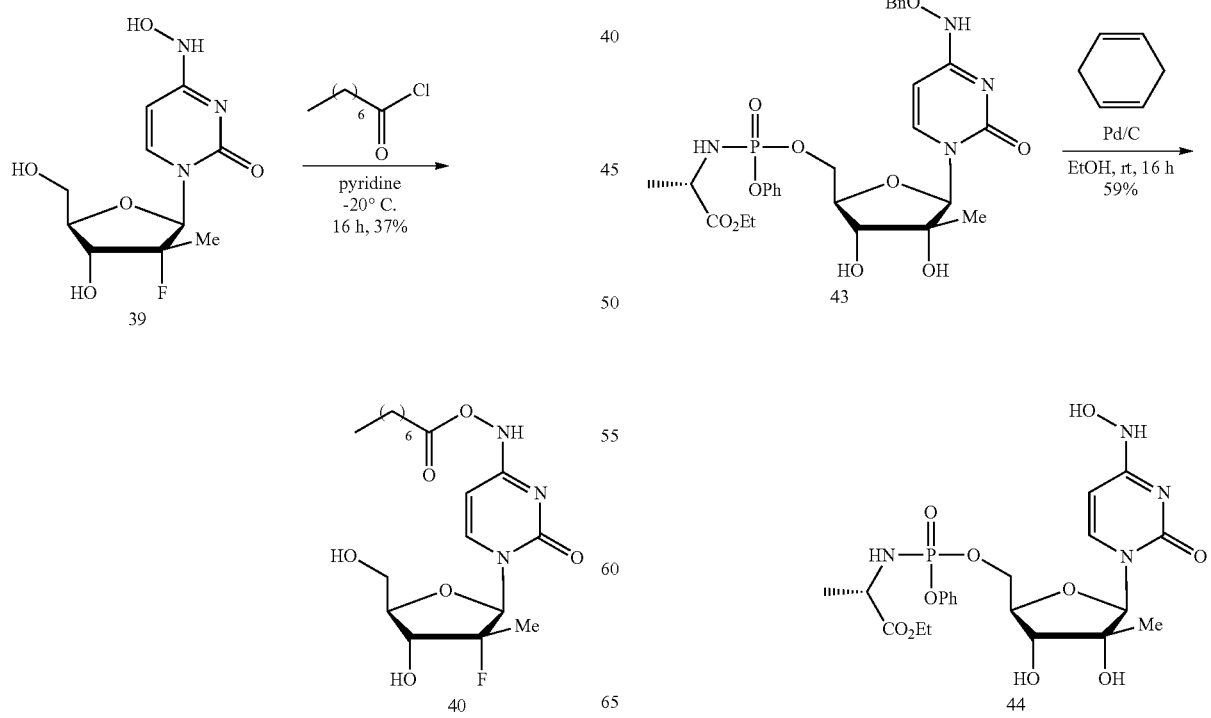

Scheme 18. Synthesis of N⁴-hydroxycytidine 2′-C-Me nucleoside prodrug 48
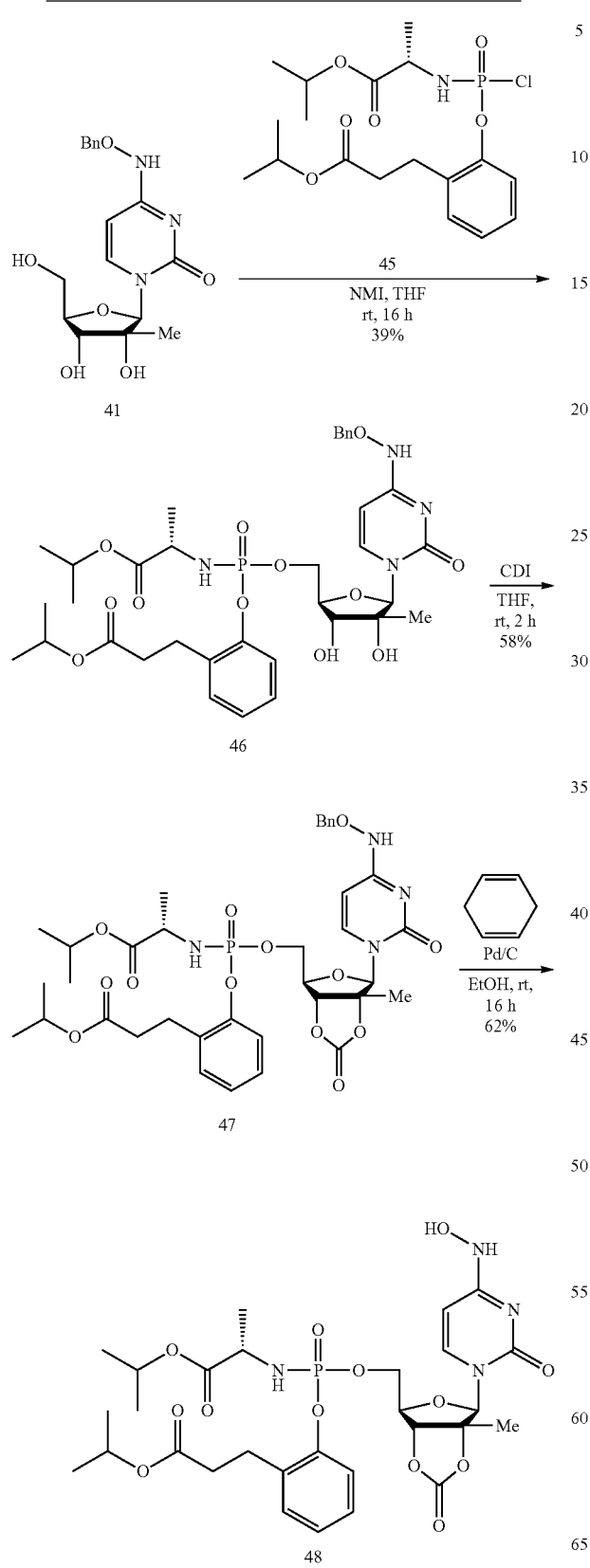
Scheme 19. Synthesis of N⁴-hydroxycytidine 2′-deoxy-2′-α-fluoro-2′-β-C-Me nucleoside prodrug 51
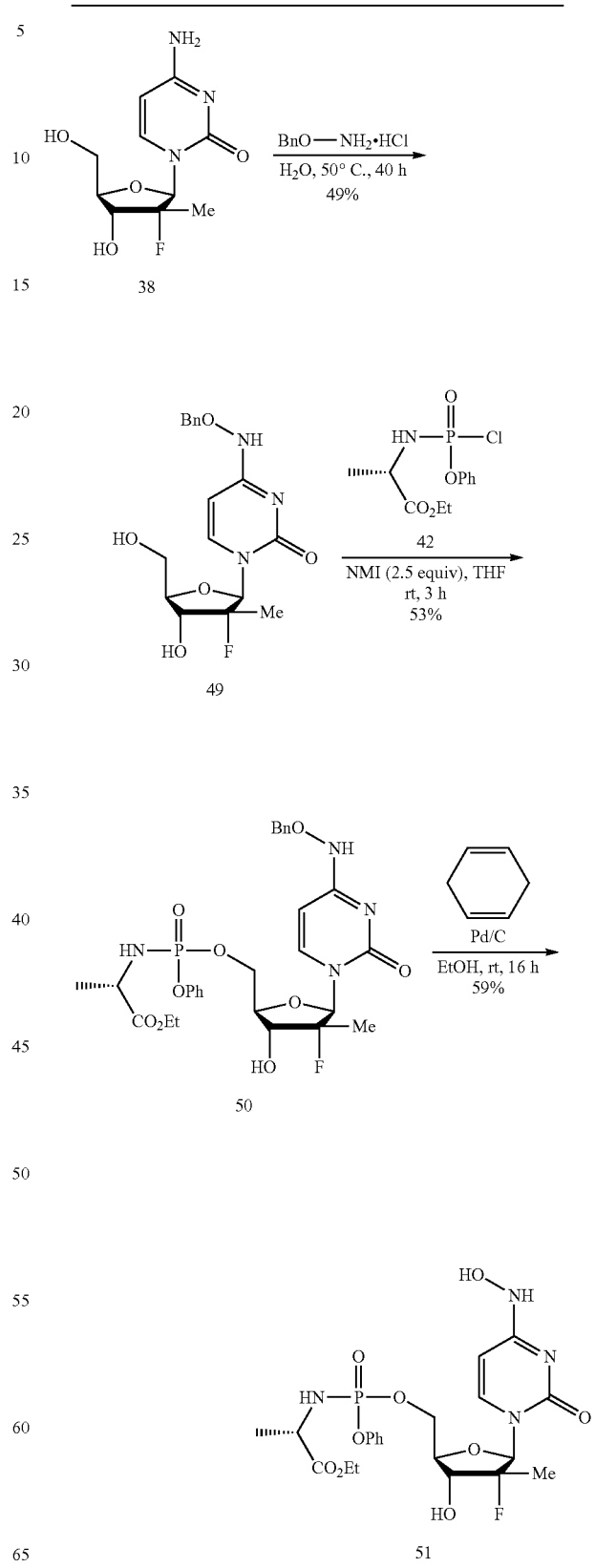

Scheme 20. Synthesis of N⁴-hydroxycytidine 2'-C-Me nucleoside prodrugs 54 and 56

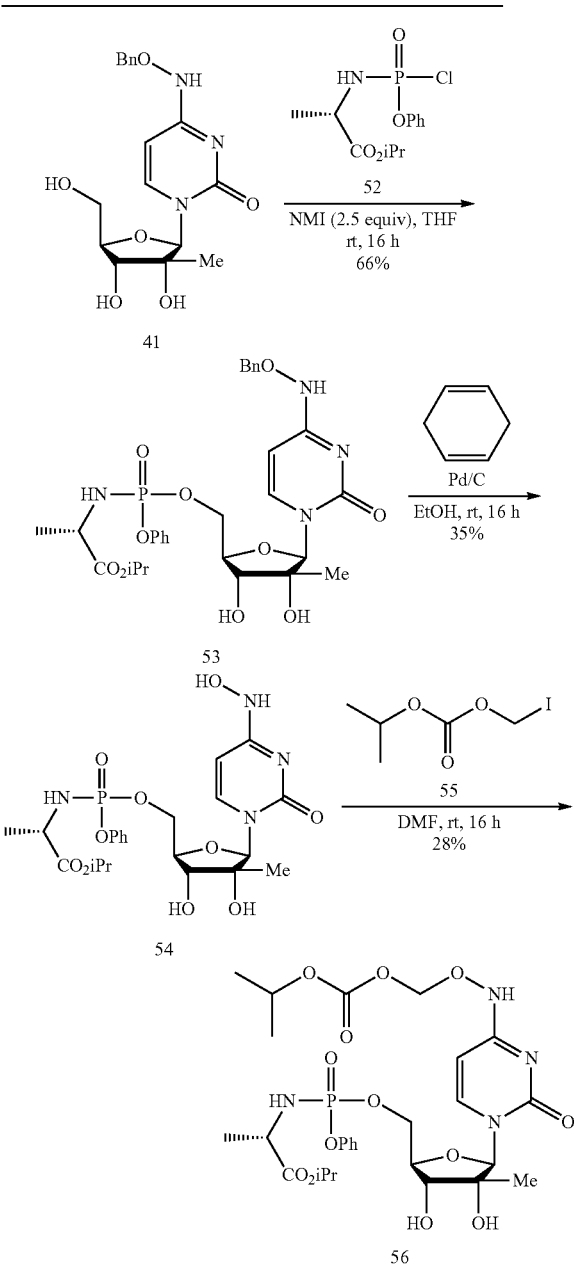

Methods for the facile preparation of active compounds of Formulas 1A and 1B are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 21 is a non-limiting example of the synthesis of active compounds of the present invention, and in particular, a synthetic approach to nucleosides 1.

Scheme 22 is a non-limiting example of the synthesis of active compounds of the present invention, and in particular, an alternate synthetic approach to nucleosides 1.

Scheme 23 is a non-limiting example of the synthesis of active compounds of the present invention, and in particular, a synthetic approach to monophosphate prodrugs I.

Scheme 24 is a non-limiting example of the synthesis of active compounds of the present invention, and in particular, a synthetic approach to monophosphate prodrugs IV, V and VI.

Scheme 25 is a non-limiting example of the synthesis of active compounds of the present invention, and in particular, a synthetic approach to monophosphate prodrugs VII.

Scheme 26 is a non-limiting example of the synthesis of active compounds of the present invention, and in particular, a synthetic approach to monophosphate prodrugs VIII.

Compounds of formula 1A can be prepared by first preparing nucleosides 1C, which in turn can be accomplished by one of ordinary skill in the art, using methods outlined in: (a) Rajagopalan, P.; Boudinot, F. D; Chu, C. K.; Tennant, B. C.; Baldwin, B. H.; Antiviral Nucleosides: Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, GA, USA, pp: 319-37 d) Handbook of Nucleoside Synthesis: Vorbruggen H. & Ruh-Pohlenz C. John Wiley & sons 2001), and by general Schemes 1-2. Specifically, nucleosides 1C can be prepared by coupling sugar 2C with a protected, silylated or free nucleoside base in the presence of Lewis acid such as TMSOTf. Deprotection of the 3'- and 5'-hydroxyls gives nucleoside 1C.

Scheme 21

A synthetic approach to nucleosides 1C. (Base and R¹ are as defined in active compound section)

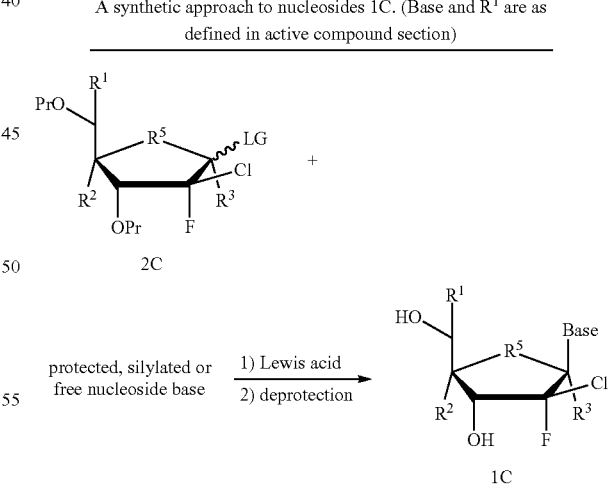

nucleoside base may contain suitable protection;
Pr = protection; LG = OCOalkyl, OCOaryl, OCOalkylaryl;
R¹, R², R³, and R⁵ are as defined in active compound section Compounds of Formula 1B can be prepared using the same general reaction scheme, but using the following intermediate (Compound 3A) rather than Compound 2C as shown above:

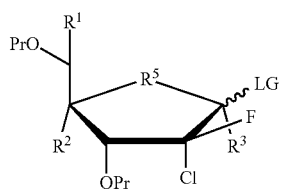

(3A)

In the schemes described herein, if a nucleoside base includes functional groups that might interfere with, or be decomposed or otherwise converted during the coupling steps, such functional groups can be protected using suitable protecting groups. After the coupling step, protected functional groups, if any, can be deprotected.

Alternatively, nucleosides 1C can be prepared from 1'-halo, 1'-sulfonate or 1'-hydroxy compounds 3B. For the case of 1'-halo or 1'-sulfonate a protected or free nucleoside base in the presence of a base such as triethyl amine or sodium hydride followed by deprotection would give nucleosides 1C. For the case of 1'-hydroxy a protected or free nucleoside base in the presence of a Mitsunobu coupling agent such as diisopropyl azodicarboxylate followed by deprotection would give nucleosides 1C.

Scheme 22 An alternate synthetic approach to nucleosides 1C.
(Base is defined in active compound section)

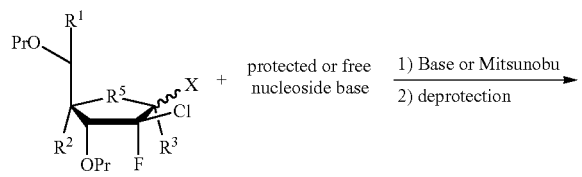

nucleoside base may contain
suitable protection; Pr = protection;
X = halogen, sulfonate or OH;
$R^1$, $R^2$, $R^3$, and $R^5$ are defined in active compound section As with Scheme 21, intermediate Compound 4A can be used instead of Compound 3B.

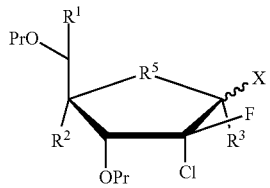

(4A)

In the case of C-nucleosides prepared from bases:

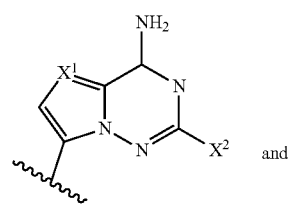

1)

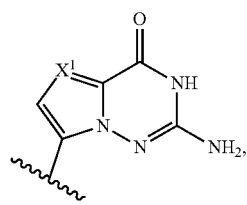

2)

methods outlined in WO09132123, WO09132135, WO2011150288 and WO2011035250 can be used.

Monophosphate prodrugs I can be prepared as outlined in Scheme 3 starting from phenol 4B. Exposure of 4B to phosphorous oxychloride or phosphorothioyl trichloride provides 5A, which is subsequently allowed to react with an amino ester 6A to give phosphoramidate 7A. Nucleoside 1C can next be converted to monophosphate analog 8A by reaction of the 5'-hydroxyl group with the chlorophosphorylamino propanoate, 7A. Removal of protecting groups from the base and/or sugar of, if present, provides monophosphate prodrugs I.

Scheme 23
A synthetic approach to monophosphate prodrugs I. (Base, $R^1$, Y, $R^{16}$, $R^{17}$, and $R^{18}$ are as defined in active compound section).

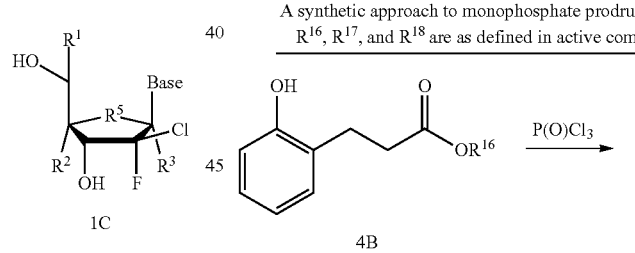

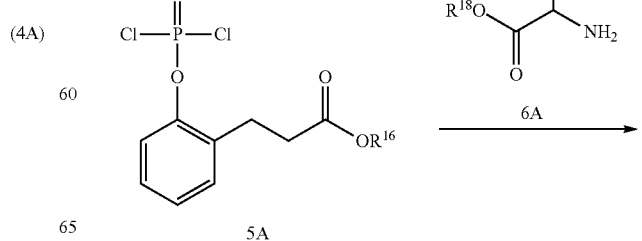

-continued

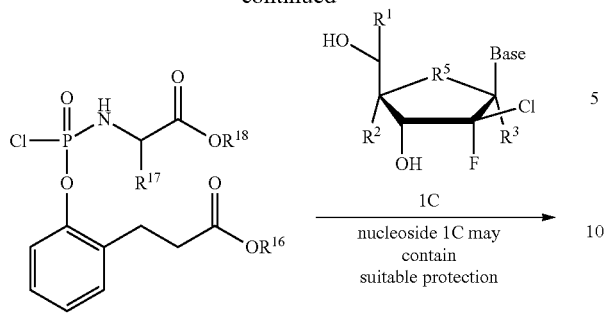

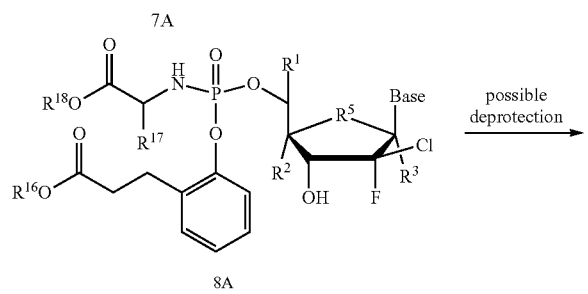

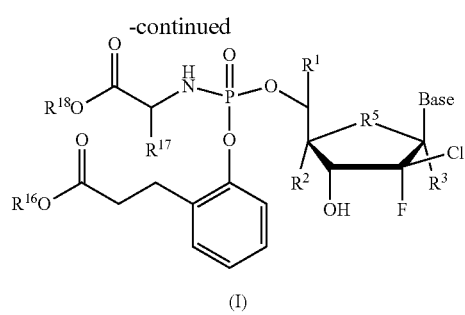

Nucleosides prepared using intermediate compounds 3A or 4A can be used instead of Compound 1C.

Monophosphate prodrugs IV can be prepared by reaction of substituted pyridine 9A with phosphorous oxychloride. The resulting intermediate can next be reacted with an ester of an L-amino acid 6A (Scheme 4) to give 11A. Nucleoside 1C can next be converted to monophosphate analog IV by reaction of the 5'-hydroxyl group with the chlorophosphoryl substrate, 11A. Removal of protecting groups, if necessary, provides monophosphate prodrugs IV. Utilizing a similar protocol with substitution of 6A by $R^{15}OH$ or 9A, monophosphate prodrugs V and VI can also be prepared.

Scheme 24 A synthetic approach to monophosphate prodrugs IV-VI. (Base, $R^1$, $R^2$, $R^3$, $R^5$, $R^{16}$, $R^{17}$, and $R^{18}$ are as defined in active compound section).

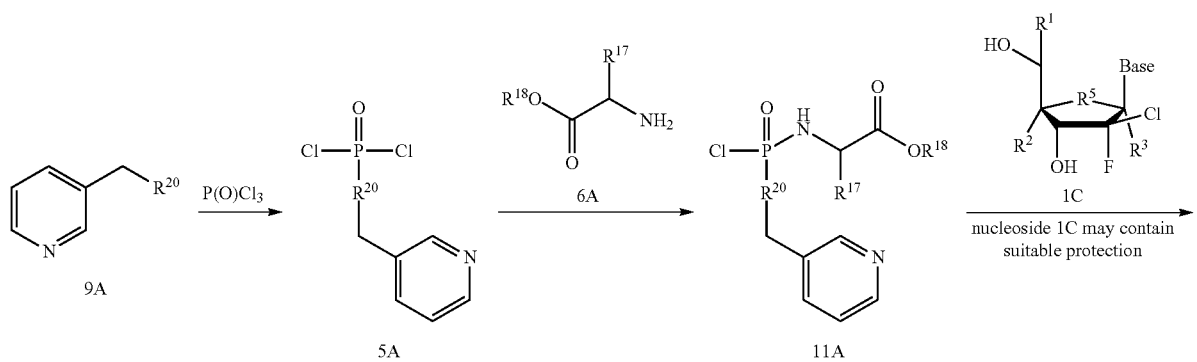

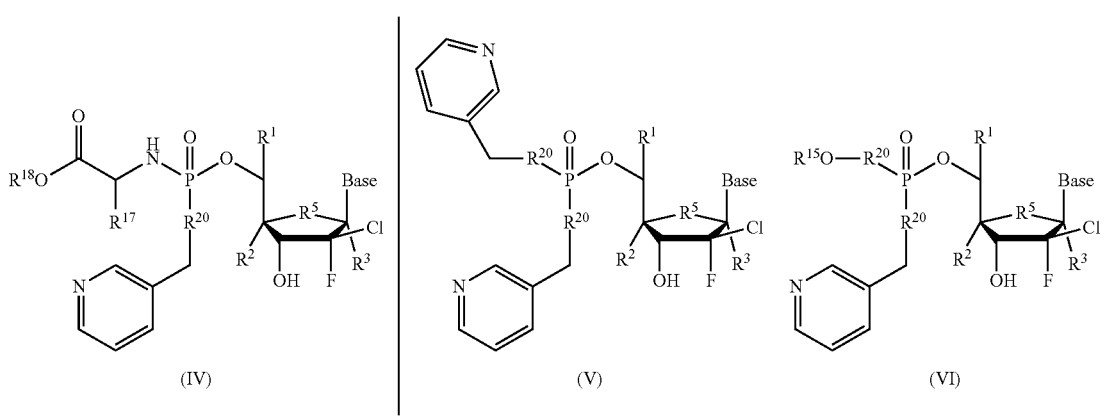

As discussed above, "suitable protection" includes protection of OH and amine moieties that are not involved in the coupling chemistry. The protecting groups, which include those described in Greene, et al., *Protective Groups in Organic Synthesis*, John Wiley and Sons, Second Edition, 1991, can be removed following the coupling step.

Nucleosides prepared using intermediate compounds 3A or 4A can be used instead of Compound 1C.

Monophosphate prodrugs VII can be prepared by reaction of 12A with phosphorous oxychloride to give 13A (Scheme 5). Nucleoside 1C can next be converted to monophosphate analog VII by reaction of the 5'-hydroxyl group with the chlorophosphoryl substrate, 13A. Removal of protecting groups, if necessary, provides monophosphate prodrugs VII.

Scheme 25 A synthetic approach to monophosphate prodrugs VII. (Base, $R^1$, $R^2$, $R^3$, $R^5$ and $R^{19}$ are as defined in active compound section).

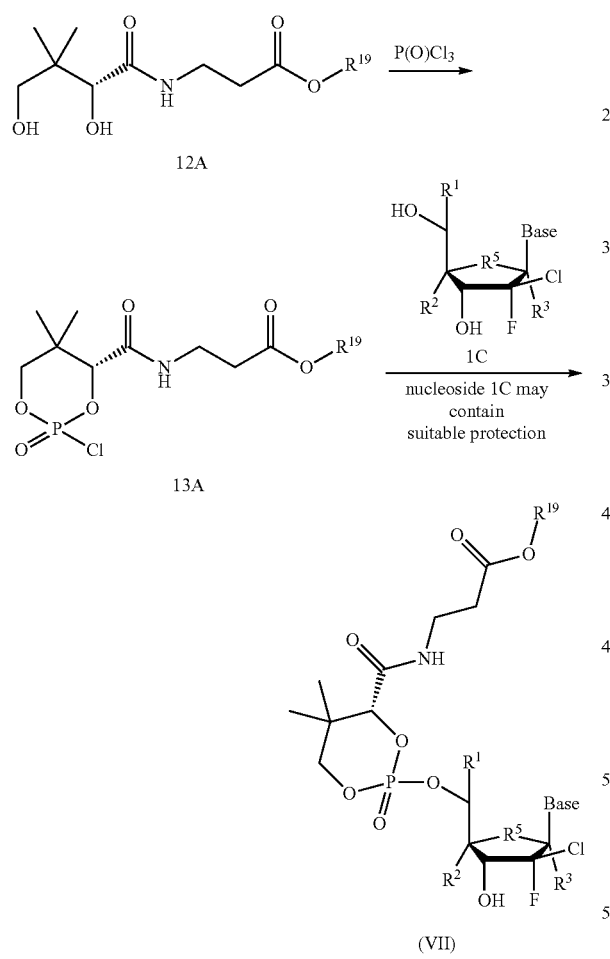

Nucleosides prepared using intermediate compounds 3A or 4A can be used instead of Compound 1C.

Monophosphate prodrugs VIII can be prepared by reaction of 14A with phosphorous oxychloride to give 15A (Scheme 6). Nucleoside 1C can next be converted to monophosphate analog VIII by reaction of the 5'-hydroxyl group with the chlorophosphoryl substrate, 15A. Removal of protecting groups, if necessary, provides monophosphate prodrugs VIII.

Scheme 26 A synthetic approach to monophosphate prodrugs VIII. (Base, $R^1$, $R^2$, $R^3$, $R^5$, and $R^{21}$ are as defined in active compound section).

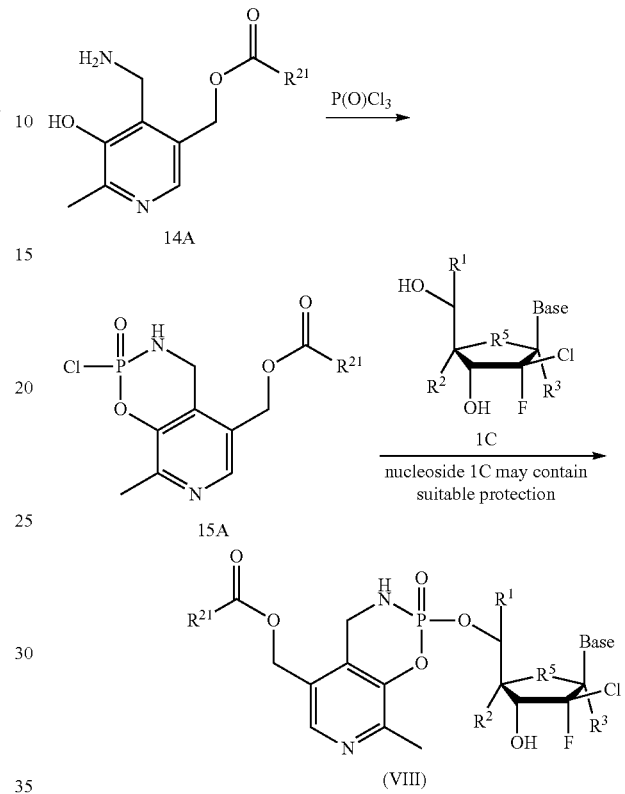

The prodrug formed in Scheme 6 is more stable than a non-cyclic phosphoramidate, and it is also less toxic than phosphoramidates containing an unsubstituted phenol moiety, by virtue of forming a non-toxic metabolite.

Nucleosides prepared using intermediate compounds 3A or 4A can be used instead of Compound 1C.

Methods for the facile preparation of active compounds of Formula A are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 27 is a non-limiting example of the synthesis of active compounds of the present invention, and in particular, a synthetic approach to nucleosides 1.

Scheme 28 is a non-limiting example of the synthesis of active compounds of the present invention, and in particular, an alternate synthetic approach to nucleosides 1.

Scheme 29 is a non-limiting example of the synthesis of active compounds of the present invention, and in particular, a synthetic approach to monophosphate prodrugs I.

Compounds of formula A can be prepared by first preparing nucleosides 1, which in turn can be accomplished by one of ordinary skill in the art, using methods outlined in: (a) Rajagopalan, P.; Boudinot, F. D; Chu, C. K.; Tennant, B. C.; Baldwin, B. H.; Antiviral Nucleosides: Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, GA, USA, pp: 319-37 d) Handbook of Nucleoside Synthesis: Vorbruggen H. & Ruh-Pohlenz C. John Wiley & sons 2001), and by general Schemes 1-2. Specifically, nucleosides 1 can be prepared by coupling sugar 2 with a protected, silylated or free nucleoside base in the presence of Lewis acid such as TMSOTf. Deprotection of the 3'- and 5'-hydroxyls gives nucleoside 1.

Scheme 27 A synthetic approach to nucleosides 1.
(Base and $R^1$ are as defined in active compound section)

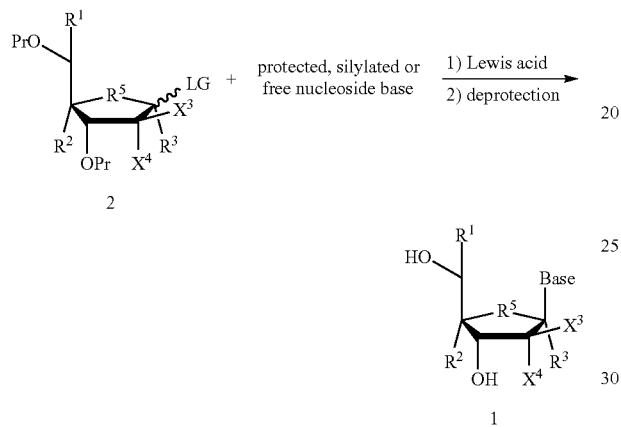

nucleoside base may contain
suitable protection; Pr = protection; $X^3$ and $X^4$ = Cl or $X^3$ and $X^4$ = Br
LG = OCOalkyl, OCOaryl, OCOalkylaryl;
$R^1$, $R^2$, $R^3$, and $R^5$ are as defined in active compound section In the schemes described herein, if a nucleoside base includes functional groups that might interfere with, or be decomposed or otherwise converted during the coupling steps, such functional groups can be protected using suitable protecting groups. After the coupling step, protected functional groups, if any, can be deprotected.

Alternatively, nucleosides 1 can be prepared from 1'-halo, 1'-sulfonate or 1'-hydroxy compounds 3. For the case of 1'-halo or 1'-sulfonate a protected or free nucleoside base in the presence of a base such as triethyl amine or sodium hydride followed by deprotection gives nucleosides 1. For the case of 1'-hydroxy a protected or free nucleoside base in the presence of a Mitsunobu coupling agent such as diisopropyl azodicarboxylate, in the presence of triphenyl phosphine, followed by deprotection gives nucleosides 1.

Scheme 28 An alternate synthetic approach to nucleosides 1.
(Base is defined in active compound section)

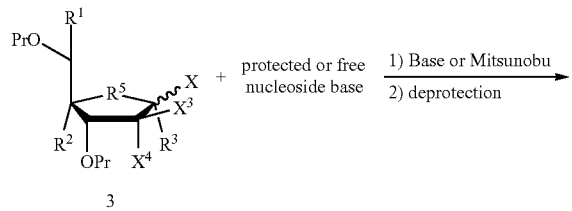

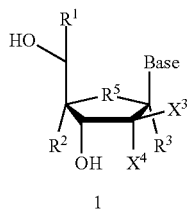

nucleoside base may contain
suitable protection; Pr = protection;
X = halogen, sulfonate or OH; $X^3$ and $X^4$ = Cl or $X^3$ and $X^4$ = Br
$R^1$, $R^2$, $R^3$, and $R^5$ are as defined in active compound section In the case of C-nucleosides prepared from bases:

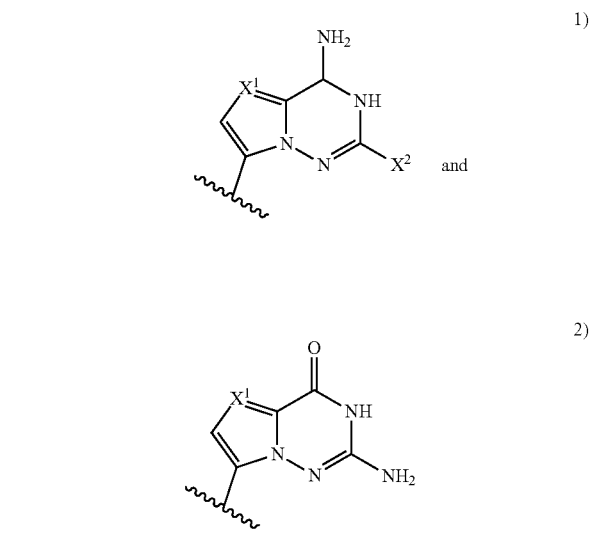

methods outlined in WO09132123, WO09132135, WO2011150288 and WO2011035250 can be used.

Monophosphate prodrugs I can be prepared as outlined in Scheme 3 starting from a phenol such as 4. Exposure of 4 to phosphorous oxychloride or phosphorothioyl trichloride provides 5, which is subsequently allowed to react with an amino ester 6 to give phosphoramidate 7. Nucleoside 1 can next be converted to monophosphate analog 8 by reaction of the 5'-hydroxyl group with the chlorophosphorylamino propanoate, 7. Removal of protecting groups from the base and/or sugar of 8, if present, provides monophosphate prodrugs I.

Scheme 29
A synthetic approach to monophosphate prodrugs I. (Base, $R^1$, Y, $R^{16}$, $R^{17}$, and $R^{18}$ are as defined in active compound section).

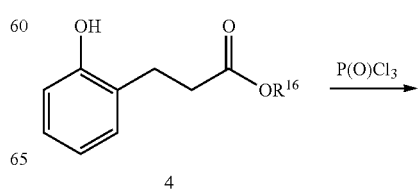

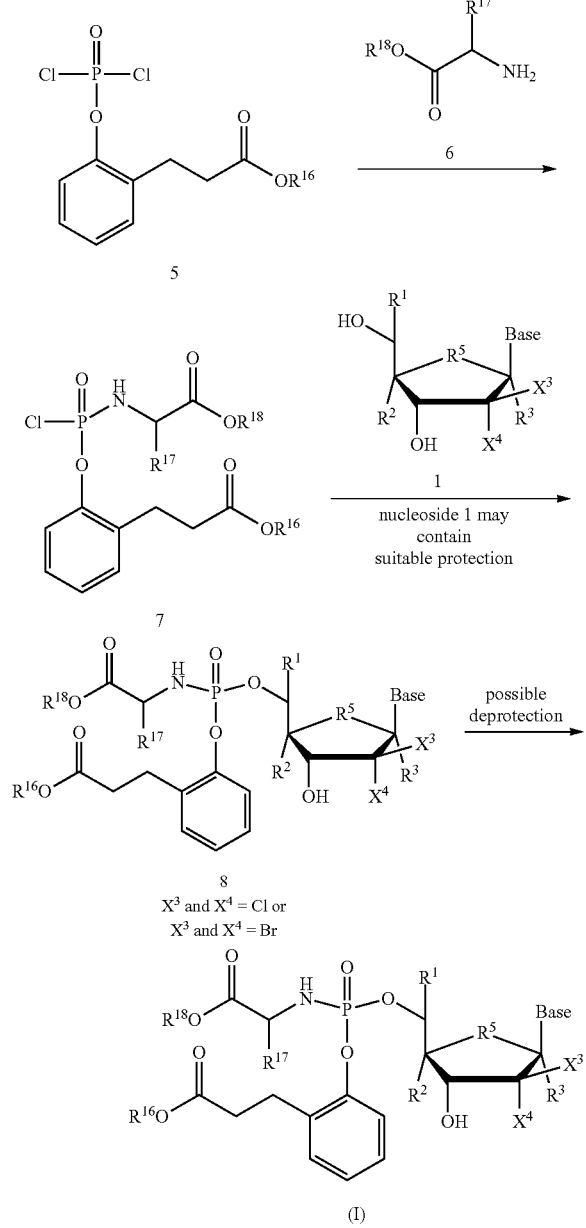

(I)

Methods for the facile preparation of active compounds of Formulas B and C are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 30 is a non-limiting example of the synthesis of active compounds of the present invention, and in particular, a synthetic approach to nucleosides 1.

Scheme 31 is a non-limiting example of the synthesis of active compounds of the present invention, and in particular, an alternate synthetic approach to nucleosides 1.

Scheme 32 is a non-limiting example of the synthesis of active compounds of the present invention, and in particular, a synthetic approach to monophosphate prodrugs I.

Scheme 33 is a non-limiting example of the synthesis of active compounds of the present invention, and in particular, a synthetic approach to monophosphate prodrugs IV, V and VI.

Scheme 34 is a non-limiting example of the synthesis of active compounds of the present invention, and in particular, a synthetic approach to monophosphate prodrugs VII.

Scheme 35 is a non-limiting example of the synthesis of active compounds of the present invention, and in particular, a synthetic approach to monophosphate prodrugs VIII.

Compounds of Formula B can be prepared by first preparing nucleosides 1, which in turn can be accomplished by one of ordinary skill in the art, using methods outlined in: (a) Rajagopalan, P.; Boudinot, F. D; Chu, C. K.; Tennant, B. C.; Baldwin, B. H.; Antiviral Nucleosides: Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, GA, USA, pp: 319-37 d) Handbook of Nucleoside Synthesis: Vorbruggen H. & Ruh-Pohlenz C. John Wiley & sons 2001), and by general Schemes 1-2. Specifically, nucleosides 1 can be prepared by coupling sugar 2 with a protected, silylated or free nucleoside base in the presence of Lewis acid such as TMSOTf. Deprotection of the 3'- and 5'-hydroxyls gives nucleoside 1.

Scheme 30 A synthetic approach to nucleosides 1.
(Base are as defined in active compound section)

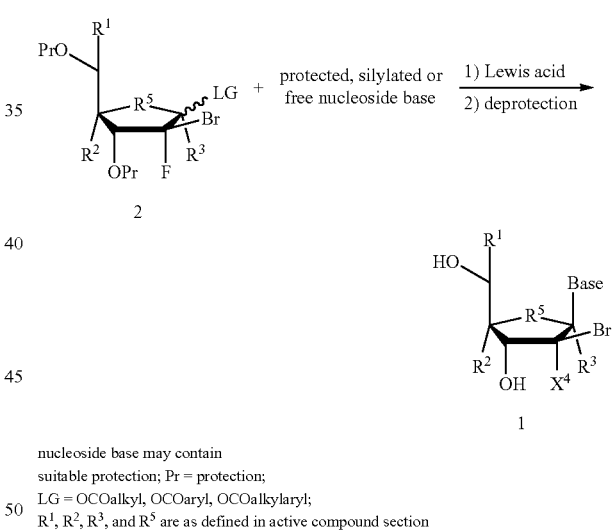

nucleoside base may contain
suitable protection; Pr = protection;
LG = OCOalkyl, OCOaryl, OCOalkylaryl;
$R^1$, $R^2$, $R^3$, and $R^5$ are as defined in active compound section In the schemes described herein, if a nucleoside base includes functional groups that might interfere with, or be decomposed or otherwise converted during the coupling steps, such functional groups can be protected using suitable protecting groups. After the coupling step, protected functional groups, if any, can be deprotected.

Alternatively, nucleosides 1 can be prepared from 1'-halo, 1'-sulfonate or 1'-hydroxy compounds 3. For the case of 1'-halo or 1'-sulfonate a protected or free nucleoside base in the presence of a base such as triethyl amine or sodium hydride followed by deprotection would give nucleosides 1. For the case of 1'-hydroxy a protected or free nucleoside base in the presence of a Mitsunobu coupling agent such as diisopropyl azodicarboxylate followed by deprotection would give nucleosides 1.

Scheme 31 An alternate synthetic approach to nucleosides 1.
(Base are as defined in active compound section)

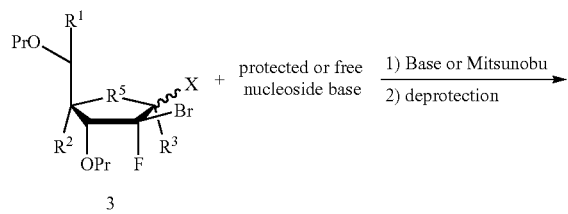

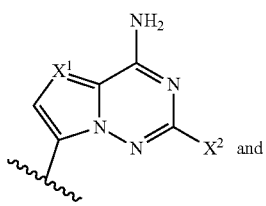

nucleoside base may contain
suitable protection; Pr = protection;
X = halogen, sulfonate or OH;
$R^1$, $R^2$, $R^3$, and $R^5$ are as defined in active compound section In the case of C-nucleosides prepared from bases:

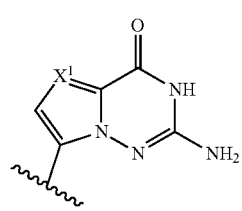

methods outlined in WO09132123, WO09132135, WO2011150288 and WO2011035250 can be used.

Monophosphate prodrugs I can be prepared as outlined in Scheme 3 starting from phenol 4. Exposure of 4 to phosphorous oxychloride or phosphorothioyl trichloride provides 5, which is subsequently allowed to react with an amino ester 6 to give phosphoramidate 7. Nucleoside 1 can next be converted to monophosphate analog 8 by reaction of the 5'-hydroxyl group with the chlorophosphorylamino propanoate, 7. Removal of protecting groups from the base and/or sugar of, if present, provides monophosphate prodrugs I.

Scheme 32 A synthetic approach to monophosphate prodrugs I.
(Base, $R^1$, $R^2$, $R^3$, $R^5$, $R^{16}$, $R^{17}$, and $R^{18}$ are as defined in active compound section).

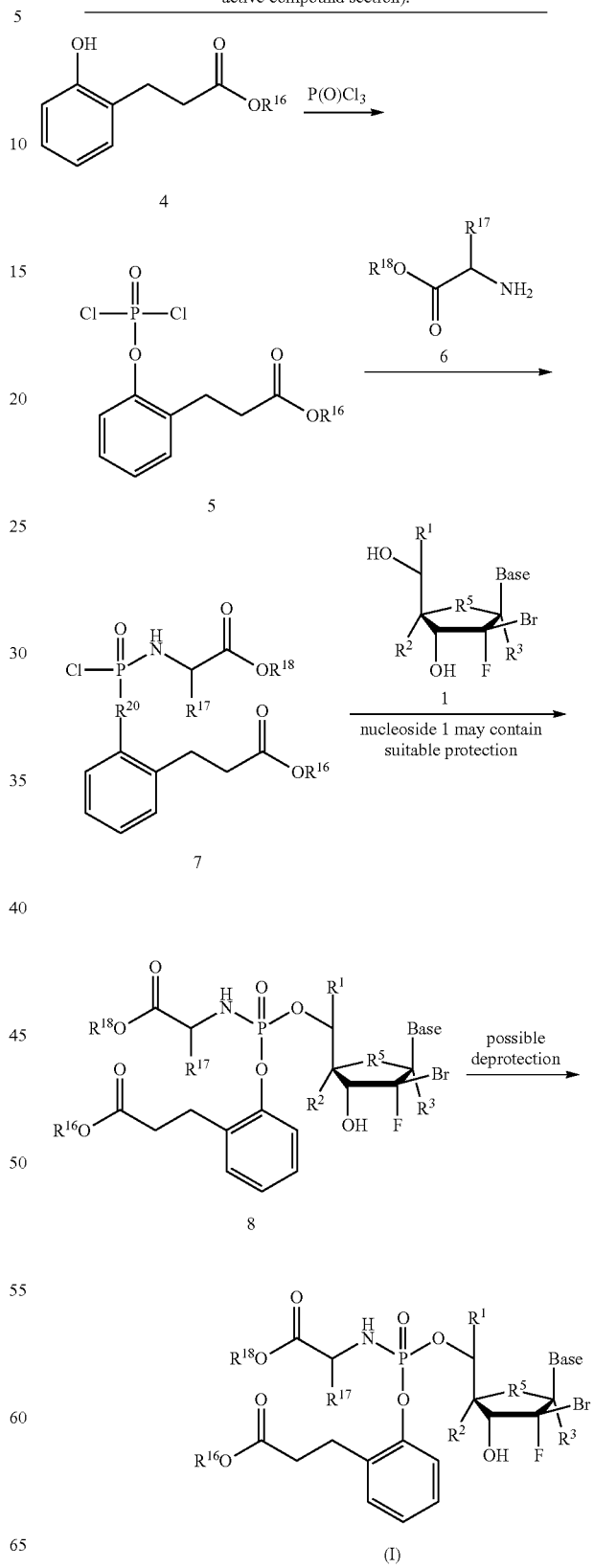

Monophosphate prodrugs IV can be prepared by reaction of substituted pyridine 9 with phosphorous oxychloride. The resulting intermediate can next be reacted with an ester of an L-amino acid 6 (Scheme 4) to give 11. Nucleoside 1 can next be converted to monophosphate analog IV by reaction of the 5'-hydroxyl group with the chlorophosphoryl substrate, 11. Removal of protecting groups, if necessary, provides monophosphate prodrugs IV. Utilizing a similar protocol with substitution of 6 by $R^{15}OH$ or 9, monophosphate prodrugs V and VI could also be prepared.

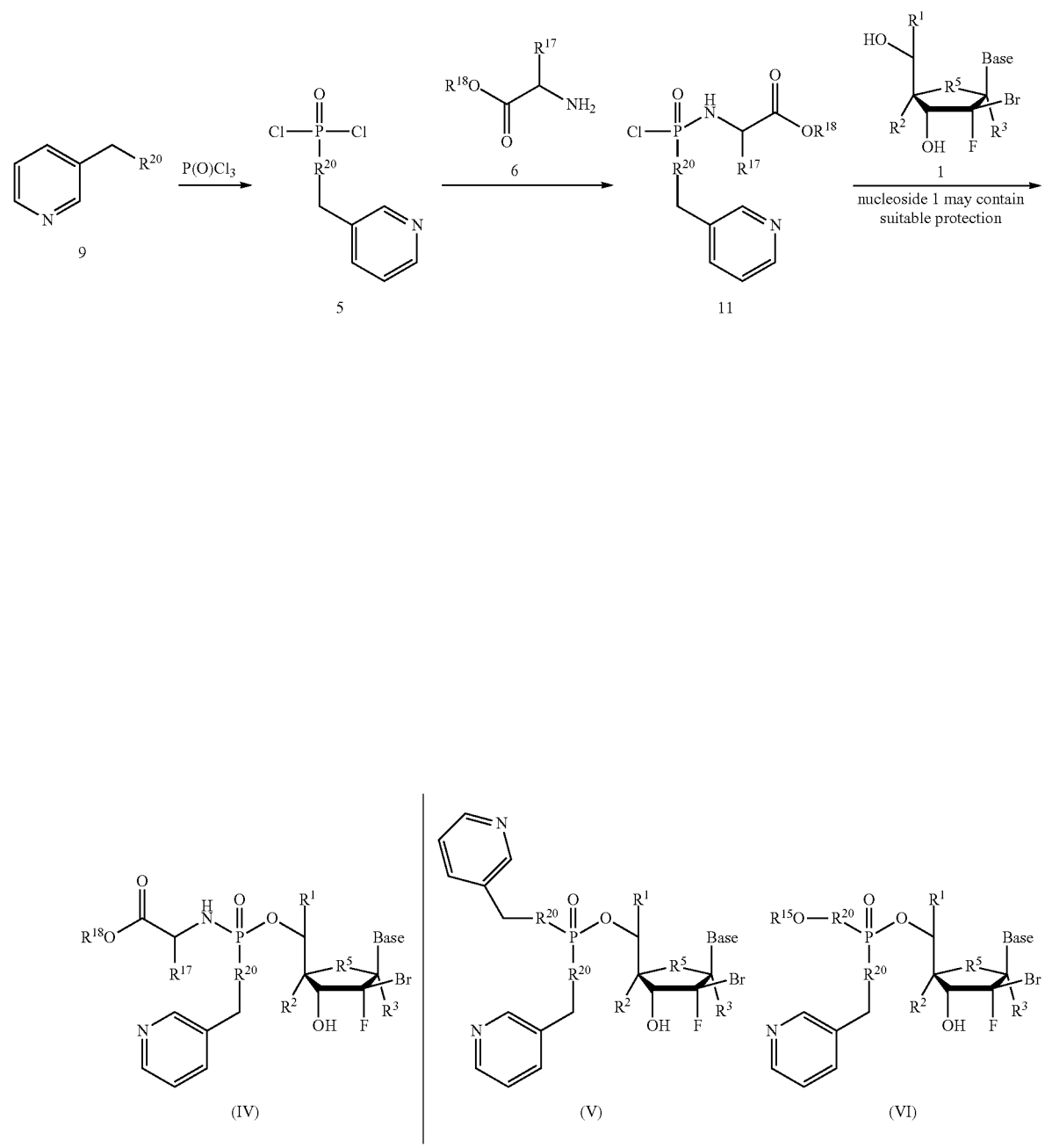

Scheme 33 A synthetic approach to monophosphate prodrugs IV-VI. (Base, $R^1$, $R^2$, $R^3$, $R^5$, $R^{16}$, $R^{17}$, and $R^{18}$ are as defined in active compound section).

Monophosphate prodrugs VII can be prepared by reaction of 12 with phosphorous oxychloride to give 13 (Scheme 5). Nucleoside 1 can next be converted to monophosphate analog VII by reaction of the 5'-hydroxyl group with the chlorophosphoryl substrate, 13. Removal of protecting groups, if necessary, provides monophosphate prodrugs VII.

Scheme 34
A synthetic approach to monophosphate prodrugs VII. (Base, $R^1$, $R^2$, $R^3$, $R^5$, and $R^{19}$ are as defined in active compound section).

Monophosphate prodrugs VIII can be prepared by reaction of 14 with phosphorous oxychloride to give 15 (Scheme 6). Nucleoside 1 can next be converted to monophosphate analog VIII by reaction of the 5'-hydroxyl group with the chlorophosphoryl substrate, 15. Removal of protecting groups, if necessary, provides monophosphate prodrugs VIII.

Scheme 35 A synthetic approach to monophosphate prodrugs VIII. (Base, $R^1$, $R^2$, $R^3$, $R^5$, and $R^{21}$ are as defined in active compound section).

The present invention will be better understood with reference to the following non-limiting examples.

Example 1

Probing the ZIKVRDRP Active Site with Homology Modeling

The ZIKV sequence from the Polynesian 2013 strain (UNIPROT-A0A024B7W1_9FLAV) was used to construct a homology model for the NS5 RNA-Dependent RNA polymerase (RDRP) using the SwissModel server (http://swissmodel.expasy.org/). SwissModel compares the input sequence to all available crystal structures as potential templates, and the ZIKV was found to be most similar to the RDRP of other flaviviridae—Dengue Fever Virus (DENV, pdbid 5DTO; 67.6% identical), West Nile Virus (WNV, pdbid 2HCS; 72.9% identical), and Japanese Encephalitis Virus (JEV, pdbid 4HDG; 70.2% identical). It is worth noting that the Hepatitis C Virus (HCV) RDRP was only 20% identical to the ZIKV sequence. The WNV and DENV RDRP lacked residues in the active site due to poor resolution, notably between the β3-α16 motifs. JEV was therefore chosen as a structural template for the ZIKV RDRP homology model due to high degree of identity and completeness.

To compare active sites, the JEV-derived homology model of the ZIKV RDRP was aligned to the Hepatitis C Virus (HCV) replication complex crystal structure with incoming Sofosbuvir-diphosphate (pdbid 4WTG). The ZIKV homology model positions the exact same residues around the 2' position as the HCV structure (FIGS. 1A and 1B).

As shown in FIGS. 1A and 1B, there is significant conservation of residues in the active site between HCV, JEV, DENV, and ZIKV. FIG. 1A provides a table of all HCV RDRP residues within 6 Å of the incoming Sofosbuvir-diphosphate from crystal structure (4WTG) and their positional equivalent for JEV, DENV, and ZIKV homology model (derived from JEV) after structural alignment. Identical residues across the structures are highlighted in blue, similar residues are highlighted in green, and dissimilar residues are orange.

FIG. 1B is a 3D representation of the HCV RDRP active site showing the position of all residues near the incoming nucleotide. The RDRP backbone is provided as transparent grey ribbons, the RNA primer:template are rendered as gold cartoons, and the incoming Sofosbuvir-diphosphate is indicated. The residues in the active site are colored according to the table in FIG. 1A, and residue substitutions between HCV and ZIKV are indicated.

As shown in these figures, there are minor, but similar, residue substitutions around the incoming nucleotide. L159, S226, and A281 are all involved in distant backbone contacts with the sugar ring (>4.5 Å), and these residues are predicted to be A159, G226, and G281 in ZIKV. F224 is positioned beneath the 4'CH in HCV, and this residue is replaced with a similarly hydrophobic and aromatic W224 in ZIKV. C316 is near the catalytic triad and contacts the preceding nucleotide near the 3'OH, and this is predicted to be S316 in DENV, JEV, and ZIKV. The only major differences between ZIKV and HCV occur near the β and γ phosphate moieties for the incoming nucleotide (R222A and H223G), which is >4 Å from the 3'OH. Due to the conservation of residues in contact with the sugar-base groups in the active site, it is reasonable to suspect nucleotide analogs that inhibit HCV will likewise inhibit ZIKV.

Example 2

Anti-Zika Virus Assay: Propagation of ZIKV in *Aedes albopictus* C6/36 Cells:

C6/36 cells (ATCC) will be maintained in Dulbecco's modified Eagle's medium DMEM; Invitrogen) supplemented with 10% fetal bovine serum (FBS) at 28° C. and 5% $CO_2$. ZIKV (MR 766 strain, ATCC) will be passed three times in C6/36 cells and infection progression will be monitored by flow cytometry. The same procedure will be performed for DENV-2 (positive control).

Another approach for culturing of the Zika virus, the following is recommended:

Media: Hyclone 199 with 5% FBS and 1% antibiotics

Infection: Seed a T-75 vented flask with $7 \times 10^6$ vero cells (http://www.atcc.org/products/all/CCL-81.aspx) the day prior to infection. Aspirate media, and quickly thaw one of the virus aliquots. Mix the virus (200 μL) with 2.5 mL warm media to infect for 1 her at 37C, shaking every 15 min. Add 5.5 mL of warm media to the infection media (~8 mL) and harvest at d4 post infection. The virus was purchased from ATCC (http://www.atcc.org/Products/All/VR-84.aspx. This virus strain is MR766 which was isolated from a rhesus macaque in Uganda (1947). The company passages the virus in suckling mouse brain. Upon receiving the virus, Vero cells can be infected to make a master stock. The virus titer is $6.6 \times 10^7$ PFU/mL as determined via plaque assay.

Quantification of ZIKV by Plaque Assay:

Four different 10-fold dilutions of purified virus (from supernatants of infected C6/36 cells) can be spread onto monolayers of Vero or BHK cells at 37° C. for 2 hr to initiate binding to cells. A mix of nutriment solution with agar can be added. Cells can be maintained at 37° C. for 6 days before the plaque assay.

Plaque counting (plaque forming unit—pfu/mL): the cells will be incubated with 3.7% formaldehyde and 0.1% crystal violet in 20% ethanol. Each virus stock (aliquots of 1 mL) are maintained at −80° C. until use.

ZIKV Infection of Vero, BHK or Huh7 Cells for Drug Evaluation:

Vero, BHK or Huh7 cells can be maintained in RPMI or DMEM supplemented with 10% FBS.

Vero, BHK or Huh7 cells can be seeded in culture 96-well microplate at a density of 5,000 cells per well. Cells can be rinsed once with phosphate-buffered saline (PBS), and ZIKV diluted to the desired multiplicity of infection (MOI) can be added to the cells.

Cells can be incubated for 24 h at 37° C. Next day, culture medium plus compounds are added to each well, and the cells can be incubated at 37° C. and 5% $CO_2$ for the duration of the experiment (viral kinetics evaluation).

Vero or Huh7 cells can be incubated with the culture supernatant from uninfected C6/36 cells to serve as negative controls (mock-infected cells).

Real-Time PCR of ZIKV:

After 5 or 6 days (depending on the results of viral kinetics) in culture, total RNA purification can be performed using RNeasy 96 kit (Qiagen) and ZIKV and ribosomal RNA amplification (endogenous control) using Real-Time PCR assay (7900 HT Sequence Detection System, Applied Biosystems or LightCycler480, Roche). The Delta CT (ZIKV and rRNA), % inhibition, $EC_{50}$, $EC_{90}$, and $CC_{50}$ can then be determined.

ZIKV Cytopathic Effect (CPE) Assay:

Vero, human neuroblastoma (U251) or Huh7 cells were exposed to the compounds at several concentrations immediately following infection with ZIKV (MOI=0.01 for Vero and MOI=0.5 for U251 or Huh7 cells) Puerto Rico strain (PRVABC59) to assess antiviral activity. Cell cytopathic effect (CPE) MTS assay (CellTiter 96@k) AQueous One Solution Cell Proliferation Promega kit, Promega) was measured four (Vero) or five (U251 or Huh7) days after compound addition to determine the levels of replication inhibition.

ZIKV Real-Time Reverse Transcription PCR Assay.

Vero cells (10,000 cells/well) were infected with ZIKV PRVABC59 (MOI=0.0001) two hours prior the addition of test compounds (400-25 μM) or control drug (at 20-1.25 μM). After a 5-day incubation, the total RNA was isolated from the cells with RNeasy kit (Qiagen). RNA was reverse transcribed into cDNA and amplified in a one-step RT-PCR multiplex reaction with LightCycler 480 RNA Master Hydrolysis Probe (Roche) using highly conserved sequences complementary to a 76 bp fragment from the ZIKV envelope gene (Lanciotti et al., 2008) and an endogenous control (TaqMan Ribosomal RNA Control Reagents; Applied Biosystems) by using the LightCycler 480 Instrument II(Roche).

REFERENCES

Kuno et al., Full-length sequencing and genomic characterization of Bagaza, Kedougou, and Zika viruses. Arch Virol. 152:687-696, 2007.

Haddow et al., Genetic Characterization of Zika Virus Strains: Geographic Expansion of the Asian Lineage. PLoS. 6: e1477, 2012.

Hamel et al., Biology of Zika Virus Infection in Human Skin Cells. J. Virol.; 89: 17, 2015.

Diagne et al., Potential of selected Senegalese *Aedes* spp. mosquitoes (Diptera: Culicidae) to transmit Zika virus. BMC Infect. Dis. 15: 492, 2015.

Example 3

Assess Anti-Zika Virus Activity and Cellular Toxicity of Nucleoside Derivatives, Modified Monophosphate and Phosphonate Prodrug Analogs i) Viruses: Stock virus can be prepared as described above.

v) Cellular Toxicity Assays: Nucleoside and nucleoside monophosphate prodrugs can be evaluated for their potential toxic effects on P4/R5 cells, MT-2 cells and uninfected PHA-stimulated human PBM cell. Log-phase P4/R5, MT-2, and PHA-stimulated human PBM cells can be seeded at $5\times10^3$ to $5\times10^4$ cells/well in 96-well cell culture plates containing 10-fold serial dilutions of the test drug. The cultures can be incubated for 2-4 days, after which 3-(4,5-dimethylthiazol-2-yl)-2,5-diphenyltetrazolium bromide (MTT) dye solution (Promega, Madison, WI) can be added to each well and incubated overnight. The reaction can be stopped with stop solubilization solution (Promega, Madison, WI) and plates can be read at a wavelength of 570 nm. The median 50% cytotoxic concentration ($CC_{50}$) can be determined from the concentration-response curve using the median effect method.

Example 4

Mitochondrial Toxicity Assays in HepG2 Cells:

i) Effect of nucleoside and nucleoside monophosphate prodrugs on Cell Growth and Lactic Acid Production: The effect on the growth of HepG2 cells can be determined by incubating cells in the presence of 0 μM, 0.1 μM, 1 μM, 10 μM and 100 μM drug. Cells ($5\times10^4$ per well) can be plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period, the cell number can be determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the nucleoside analogs on lactic acid production, HepG2 cells from a stock culture can be diluted and plated in 12-well culture plates at $2.5\times10^4$ cells per well. Various concentrations (0 μM, 0.1 μM, 1 μM, 10 μM and 100 μM) of nucleoside analog can be added, and the cultures can be incubated at 37° C. in a humidified 5% $CO_2$ atmosphere for 4 days. At day 4, the number of cells in each well can be determined and the culture medium collected. The culture medium can be filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of $N^4$-hydroxycytidine nucleosides derivatives, modified monophosphate and phosphonates prodrugs analogs can be used to indicate a drug-induced cytotoxic effect.

ii) Effect on nucleosides derivatives, modified monophosphate and phosphonates prodrugs analogs on Mitochondrial DNA Synthesis: a real-time PCR assay to accurately quantify mitochondrial DNA content has been developed (see Stuyver L J, Lostia S, Adams M, Mathew J S, Pai B S, Grier J, Thamish P M, Choi Y, Chong Y, Choo H, Chu C K, Otto M J, Schinazi R F. Antiviral activities and cellular toxicities of modified 2',3'-dideoxy-2',3'-didehydrocytidine analogs. *Antimicrob. Agents Chemother.* 2002; 46: 3854-60). This assay can be used in all studies described in this application that determine the effect of nucleoside analogs on mitochondrial DNA content. In this assay, low-passage-number HepG2 cells can be seeded at 5,000 cells/well in collagen-coated 96-well plates. Nucleoside monophosphate analogs can be added to the medium to obtain final concentrations of 0 μM, 0.1 μM, 10 μM and 100 μM. On culture day 7, cellular nucleic acids can be prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the β-actin or rRNA gene can be amplified from 5 μl of the eluted nucleic acids using a multiplex Q-PCR protocol with suitable primers and probes for both target and reference amplifications. For COXII the following sense, probe and antisense primers can be used, respectively: 5'-TGCCCGCCATCATCCTA-3' (SEQ ID NO: 1), 5'-tetrachloro-6-carboxyfluorescein-TCCT-CATCGCCCTCCCATCCC-TAMRA-3' (SEQ ID NO: 2) and 5'-CGTCTGTTATGTAAAGGATGCGT-3' (SEQ ID NO: 3). For exon 3 of the β-actin gene (GenBank accession number E01094) the sense, probe, and antisense primers are 5'-GCGCGGCTACAGCTTCA-3' (SEQ ID NO: 4), 5'-6-FAM-CACCACGGCCGAGCGGGA-TAMRA-3' (SEQ ID NO: 5) and 5'-TCTCCTTAATGTCACGCACGAT-3' (SEQ ID NO: 6), respectively. The primers and probes for the rRNA gene are commercially available from Applied Biosystems. Since equal amplification efficiencies can be obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample—CT for target control)—(CT for average reference test−CT for reference control) (see Johnson M R, K Wang, JB Smith, MJ Heslin, RB Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug indicates mitochondrial toxicity.

iii) Electron Microscopic Morphologic Evaluation: NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells.

Biochem. Pharmacol. 1996, 52, 1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, XJ Zhou, JP Sommadossi, VM Darley-Usmar. Differential effects of antiretroviral nucleoside analogs on mitochondrial function in HepG2 cells. Antimicrob. Agents Chemother. 2000, 44, 496-503). For example, electron micrographs of HepG2 cells incubated with 10 μM fialuridine (FIAU; 1,2'-deoxy-2'-fluoro-1-D-arabinofuranosly-5-iodo-uracil) can show the presence of enlarged mitochondria with morphological changes consistent with mitochondrial dysfunction. To determine if nucleoside and nucleoside monophosphate prodrugs promoted morphological changes in mitochondria, HepG2 cells ($2.5 \times 10^4$ cells/mL) can be seeded into tissue cultures dishes (35 by 10 mm) in the presence of 0 μM, 0.1 μM, 1 μM, 10 μM and 100 μM nucleoside analog. At day 8, the cells can be fixed, dehydrated, and embedded in Eponas described previously. Thin sections can be prepared, stained with uranyl acetate and lead citrate, and then examined using transmission electron microscopy.

Example 5

Mitochondrial Toxicity Assays in Neuro2A Cells

To estimate the potential of nucleoside analogs to cause neuronal toxicity, mouse Neuro2A cells (American Type Culture Collection 131) can be used as a model system (see Ray A S, Hemandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% ($CC_{50}$) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. In all experiments, ddC and AZT can be used as control nucleoside analogs.

Example 6

Effect of Nucleotide Analogs on the DNA Polymerase and Exonuclease Activities of Mitochondrial DNA Polymerase γ i) Purification of Human Polymerase γ: The recombinant large and small subunits of polymerase γ can be purified as described previously (see Graves S W, Johnson A A, Johnson K A. Expression, purification, and initial kinetic characterization of the large subunit of the human mitochondrial DNA polymerase. Biochemistry. 1998, 37, 6050-8; Johnson A A, Tsai Y, Graves S W, Johnson K A. Human mitochondrial DNA polymerase holoenzyme: reconstitution and characterization. Biochemistry 2000; 39: 1702-8). The protein concentration can be determined spectrophotometrically at 280 nm, with extinction coefficients of 234,420, and 71,894 $M^{-1}$ $cm^{-1}$ for the large and the small subunits of polymerase γ, respectively.

ii) Kinetic Analyses of Nucleotide Incorporation: Pre-steady-state kinetic analyses can be carried out to determine the catalytic efficiency of incorporation (k/K) for DNA polymerase γ for nucleoside-TP and natural dNTP substrates. This allows determination of the relative ability of this enzyme to incorporate modified analogs and predict toxicity. Pre-steady-state kinetic analyses of incorporation of nucleotide analogs by DNA polymerase γ can be carried out essentially as described previously (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. *Antiviral Res.* 2004, 62, 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. *Antimicrob Agents Chemother.* 2004, 48, 1300-6). Briefly, a pre-incubated mixture of large (250 nM) and small (1.25 mM) subunits of polymerase γ and 60 nM DNA template/primer in 50 mM Tris-HCl, 100 mM NaCl, pH 7.8, can be added to a solution containing $MgCl_2$ (2.5 mM) and various concentrations of nucleotide analogs. Reactions can be quenched and analyzed as described previously. Data can be fit to the same equations as described above.

iii) Assay for Human Polymerase γ 3' 5' Exonuclease Activity: The human polymerase γ exonuclease activity can be studied by measuring the rate of formation of the cleavage products in the absence of dNTP. The reaction can be initiated by adding $MgCl_2$ (2.5 mM) to a pre-incubated mixture of polymerase γ large subunit (40 nM), small subunit (270 nM), and 1,500 nM chain-terminated template/primer in 50 mM Tris-HCl, 100 mM NaCl, pH 7.8, and quenched with 0.3M EDTA at the designated time points. All reaction mixtures can be analyzed on 20% denaturing polyacrylamide sequencing gels (8M urea), imaged on a Bio-Rad GS-525 molecular image system, and quantified with Molecular Analyst (Bio-Rad). Products formed from the early time points were plotted as a function of time. Data can be fitted by linear regression with Sigma Plot (Jandel Scientific). The slope of the line can be divided by the active enzyme concentration in the reaction to calculate the kexo for exonuclease activity (see Murakami E, Ray AS, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004; 62: 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004; 48: 1300-6).

Example 7

Assay for Bone Marrow Cytotoxicity

Primary human bone marrow mononuclear cells can be obtained commercially from Cambrex Bioscience (Walkersville, MD). CFU-GM assays can be carried out using a bilayer soft agar in the presence of 50 units/mL human recombinant granulocyte/macrophage colony-stimulating factor, while BFU-E assays use a methylcellulose matrix containing 1 unit/mL erythropoietin (see Sommadossi J P, Carlisle R. Toxicity of 3'-azido-3'-deoxythymidine and 9-(1, 3-dihydroxy-2-propoxymethyl) guanine for normal human hepatopoietic progenitor cells in vitro. *Antimicrob. Agents Chemother.* 1987; 31: 452-454; Sommadossi, JP, Schinazi, RF, Chu, C K, and Xie, MY. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment was performed in duplicate in cells from three different donors. AZT can be used as a positive control. Cells can be incubated in the presence of the compound for 14-18 days at 37° C. with 5% $CO_2$, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 8

Cytotoxicity Assay

The toxicity of the compounds can be assessed in Vero, human PBM, CEM (human lymphoblastoid), and can be assessed in MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide can be included as positive cytotoxic control, and untreated cells exposed to solvent can be included as negative controls. The cytotoxicity (IC50) can be obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

Example 9

Synthesis of Nucleoside Analog Triphosphates

Nucleoside analog triphosphates can be synthesized from suitably protected nucleosides, using the Ludwig and Eckstein's method. (Ludwig J, Eckstein F. "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one" J. Org. Chem. 1989, 54 631-5) The crude nucleoside analog triphosphate can be purified, for example, by FPLC using a HiLoad 26/10 Q Sepharose Fast Flow Pharmacia column and gradient of TEAB buffer (pH 7.0). The product can be characterized by UV spectroscopy, proton and phosphorus NMR, mass spectroscopy and HPLC.

The resulting triphosphates can be used as controls for the cellular pharmacology assays described above and for kinetic work with Zika virus polymerase and other viral and human polymerases.

Example 10

Phosphorylation Assay of Nucleoside to Active Triphosphate in HepG2 Cells

To determine the cellular metabolism of the compounds, HepG2 cells can be obtained from the American Type Culture Collection (Rockville, MD), and are grown in 225 $cm^2$ tissue culture flasks in minimal essential medium supplemented with non-essential amino acids, 1% penicillin-streptomycin. The medium can be renewed every three days, and the cells can be subcultured once a week. After detachment of the adherent monolayer with a 10 minute exposure to 30 mL of trypsin-EDTA and three consecutive washes with medium, confluent HepG2 cells can be seeded at a density of $2.5 \times 10^6$ cells per well in a 6-well plate and exposed to 10 μM of [$^3$H] labeled active compound (500 dpm/pmol) for the specified time periods.

The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol. The extracts are then combined, dried under gentle filtered air flow and stored at −20° C. until HPLC analysis.

Example 11

Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives approximately 250 μCi of $^3$H activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (TmaX), area under the curve (AUC), half-life of the dosage concentration (TV), clearance (CL), steady state volume and distribution (Vss) and bioavailability (F).

Example 12

Cell Protection Assay (CPA)

The assay can be performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate. Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm.

The 50% effective concentration ($EC_{50}$) values are defined as the compound concentration that achieved 50% reduction of cytopathic effect of the virus.

Example 13

Plaque Reduction Assay

For a given compound, the effective concentration can be determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Example 14

Yield Reduction Assay

For a given compound, the concentration to obtain a 6-log reduction in viral load can be determined in duplicate 24-well plates by yield reduction assays. The assay is performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986, with minor modifications.

Briefly, MDBK cells are seeded onto 24-well plates ($2 \times 10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates ($5 \times 10^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 15

Sulfasalazine, an FDA approved anti-inflammatory drug, can also be used, either alone or in combination, for preventing, treating and curing Zika and Dengue virus infections. The inventors have generated data demonstrating that this compound can inhibit these viruses in culture selectively at micromolar concentrations, with no toxicity up to 100 µM. Approved in 1950, sulfasalazine (Azulfidine) is commonly used to treat ulcerative colitis and rheumatoid arthritis when administered as delayed-release tablets (Azulfidine EN-tabs).

Anti-Dengue activity was shown in a model using a DENV-2 replicon, where % inhibition at 30 µM was 77.4%, and the $EC_{50}$ was 8.3 µM. In a DENV-2 Huh-7 infectious assay, the $EC_{50}$ was 22.2 µM, and the $EC_{90}$ was 61.9 µM. In a DENV-2 VERO infectious assay, the $EC_{50}$ was >100 µM.

West Nile virus activity was shown using a WNV replicon, where % inhibition at 30 µM was 78.5%. The $EC_{50}$ was 9.9 µM and the $EC_{90}$ was 78.3 µM.

Toxicity in baby hamster kidney (BHK) cells was >100 µM, so the compounds can be effective at a safe concentration.

When the Following Compound

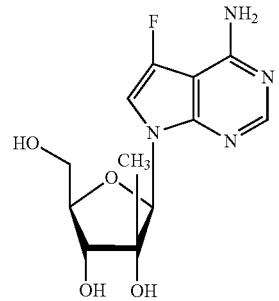

was used as a control, the $EC_{50}$ was 2.6 µM (Huh-7) and 8.6 (Vero) µM.

With respect to Norovirus and HCV, no effect was observed, up to 100 µM

Sulfasalazine also has activity in DENV-2-Huh infectious system, with an $EC_{50}$ of 22.2 µM and an $EC_{90}$ of 61.9 µM. However, it was not active in Vero cells with an $EC_{50}$>100 µM (<1% inhibition).

Sulfasalazine also has activity against West Nile Virus in a WNV replicon model, with an $EC_{50}$=9.9 µM and $EC_{90}$=78.3 µM.

Sulfasalazine also has activity with an $EC_{50}$=8.3 µM, and with no signs of toxicity in BHK up to 100 µM.

Sulfasalazine showed activity against Dengue (DENV2) and WNV at 30 µM, where the percent inhibition against DENV2 was 77.4 and the percent inhibition against WNV was 78.5.

Sulfasalazine is known to cross into the placenta (to concentrations equal to maternal plasma), and is safe for a woman to take while pregnant. Sulfasalazine also crosses the blood brain barrier. In terms of a therapeutic window, sulfasalazine is extraordinarily safe, as doses of up to 4 g/day can be taken without side effects (see, for example, Schroder and Campbell, Clinical Pharmacology and Therapeutics, 13(4): 539-551 (1972)). In terms of pharmacokinetic properties, sulfasalazine has generally safe plasma levels (6-50 µg/ml, which equates to 15-125 µM).

Accordingly, the compound is safe at in vivo concentrations greater than those required to inhibit flaviviruses like ZIKV, DENV, and WNV.

Example 16

In Vitro Data in a Vero Cell Model

At 8 AM on Day 1, 10,000 cells/well were plated in a 96 well plate. At 2 PM, MOI 0.1 Zika virus was added. At 3 PM, virus inoculum was removed, and various concentrations of drug-containing medium was added, at multiple concentrations (duplicates of 10, 1, 0.1, 0.01 M).

On Day 3, supernatants were harvested, and frozen for later RT-PCR confirmation. Cells were harvested, stained with 4G2 antibody, and intracellular virus was quantified with FACS. The $EC_{50}$/$EC_{90}$ were then calculated.

Concentrations of 10, 1, 0.1, 0.01 µM were assayed in duplicate for 10 total drugs. All cells were harvested, but the only cells stained with antibody were those contacted with the following compounds, in the listed concentrations:

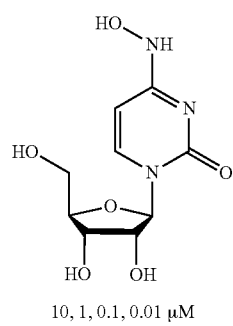

10, 1, 0.1, 0.01 µM

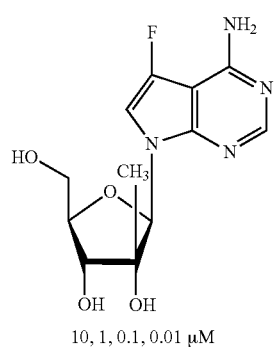

10, 1, 0.1, 0.01 µM

All others only 10 µM

If >30% inhibition was observed at 10 µM, all doses for stored cells were stained with antibody and the EC$_{50}$/EC$_{90}$ was calculated.

Figure 2A:
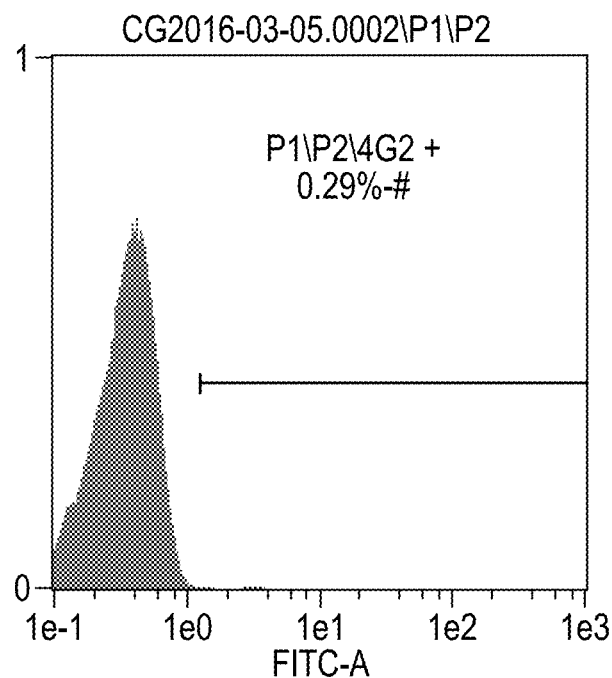
Figure 2B:
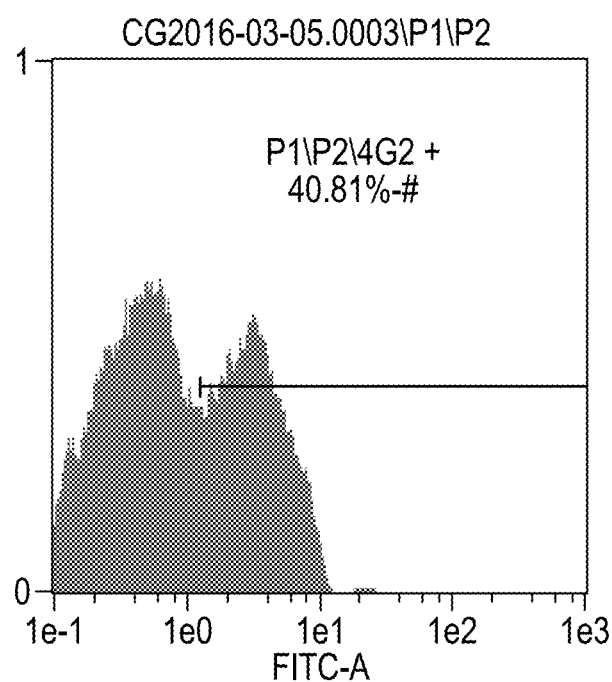
Figure 3A:
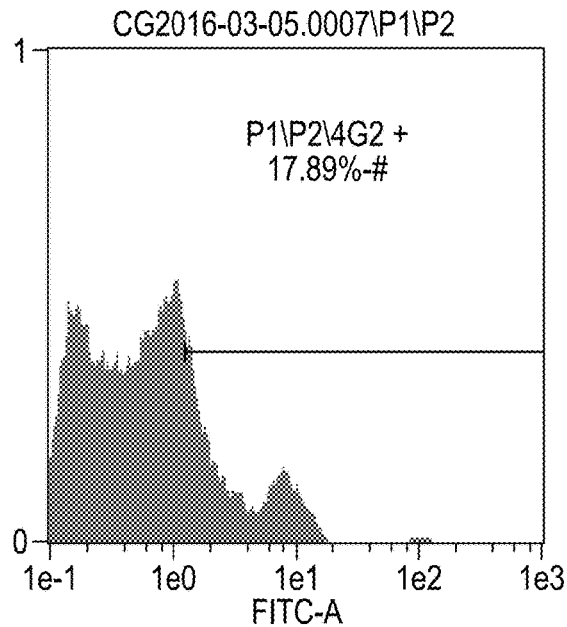
Figure 3B:
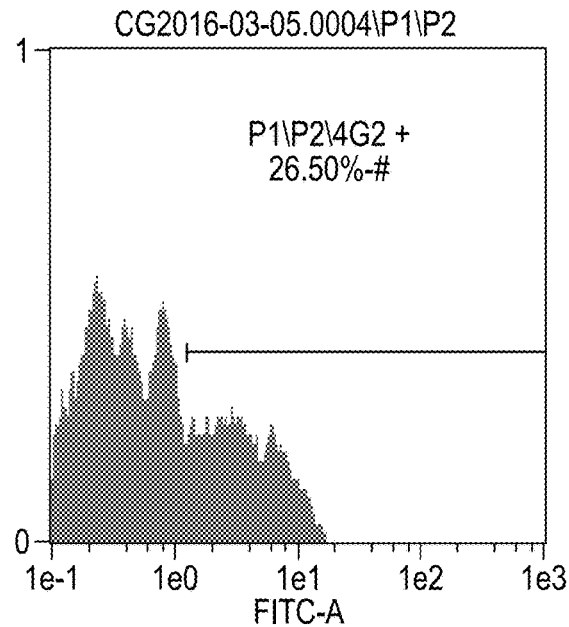
Figure 3C:
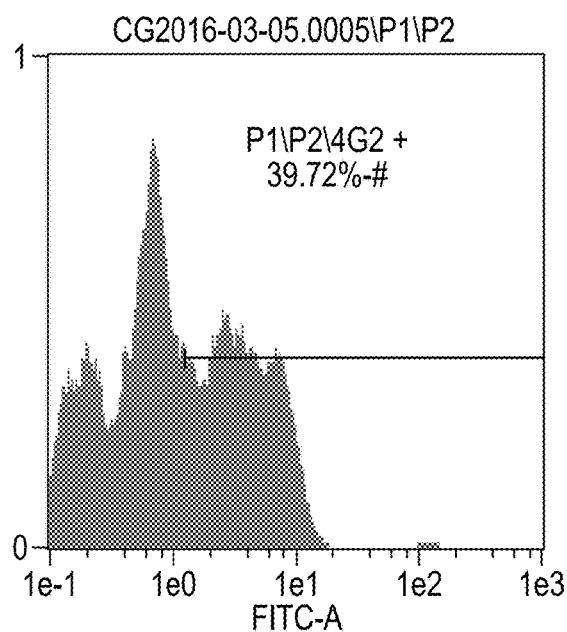
Figure 3D:
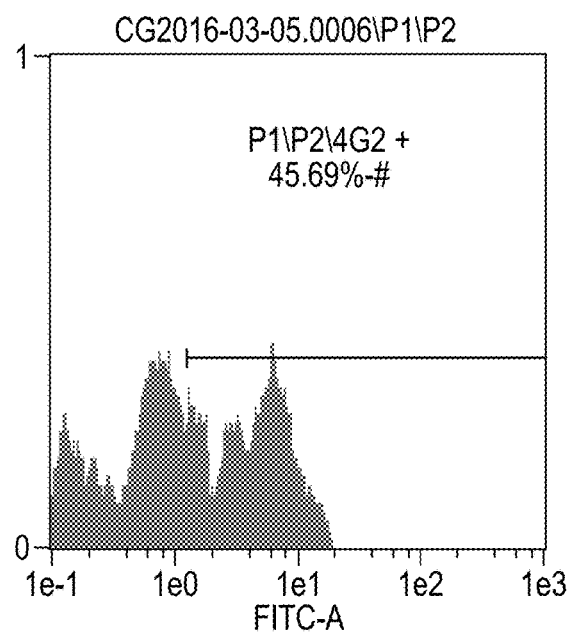
Figure 4A:
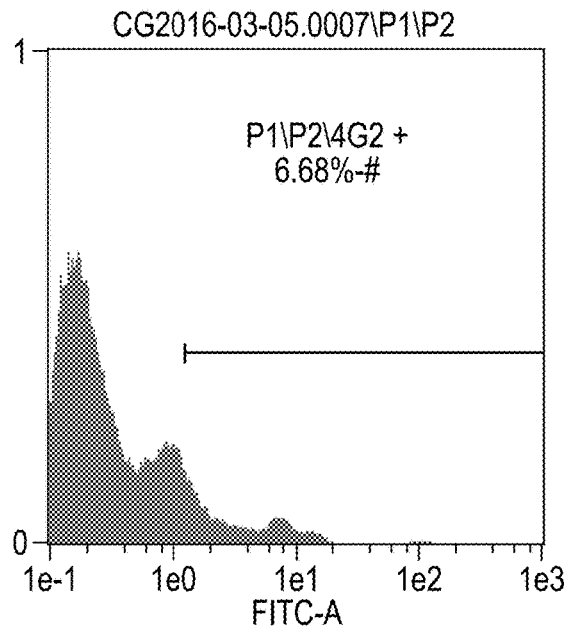
Figure 4B:
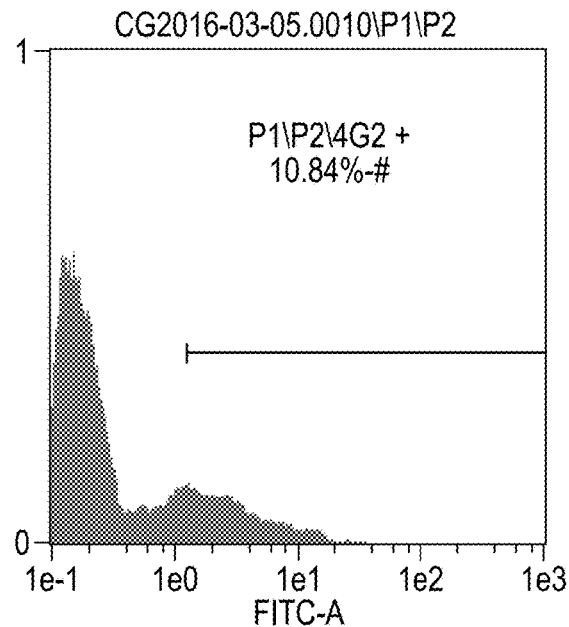
Figure 4C:
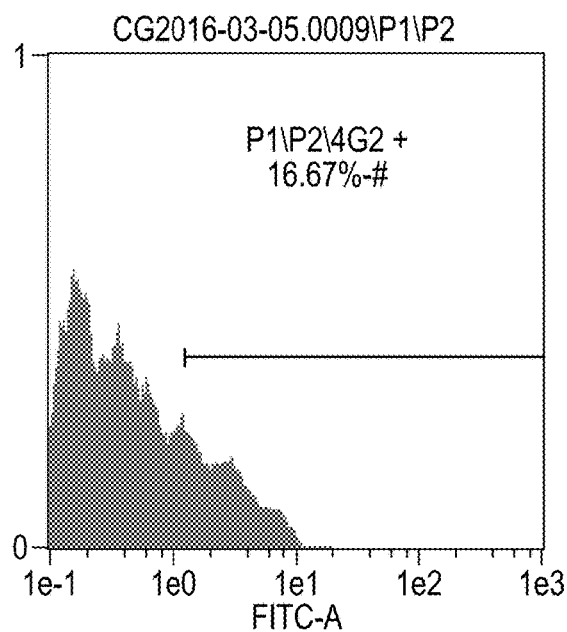
Figure 4D:
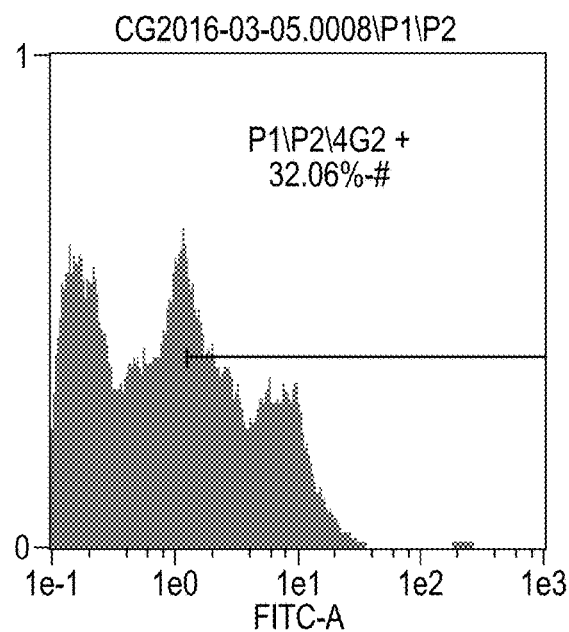
Figure 5A:
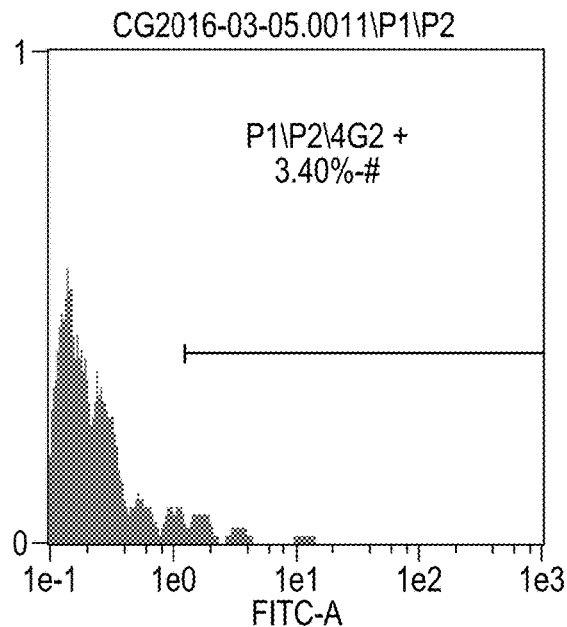
Figure 5B:
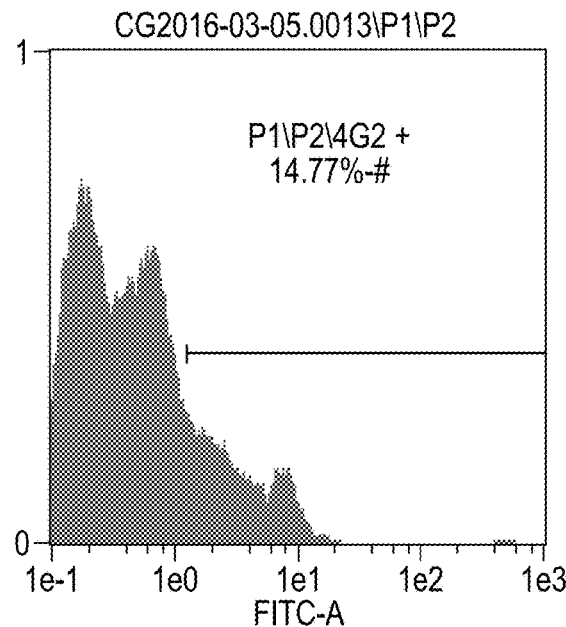
Figure 5C:
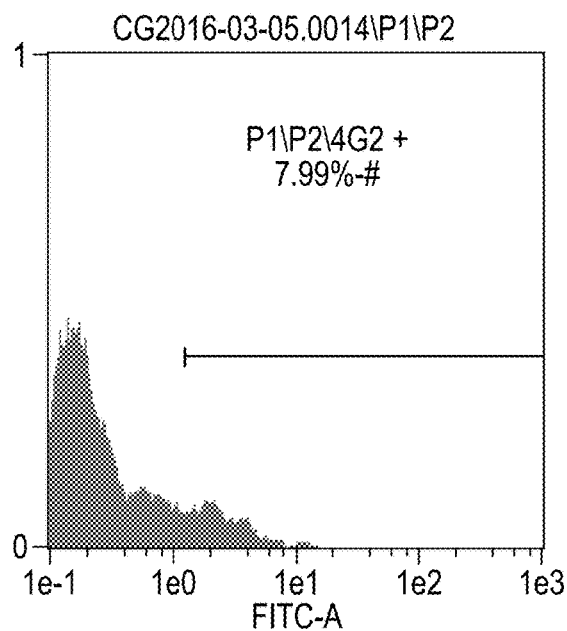
Figure 5D:
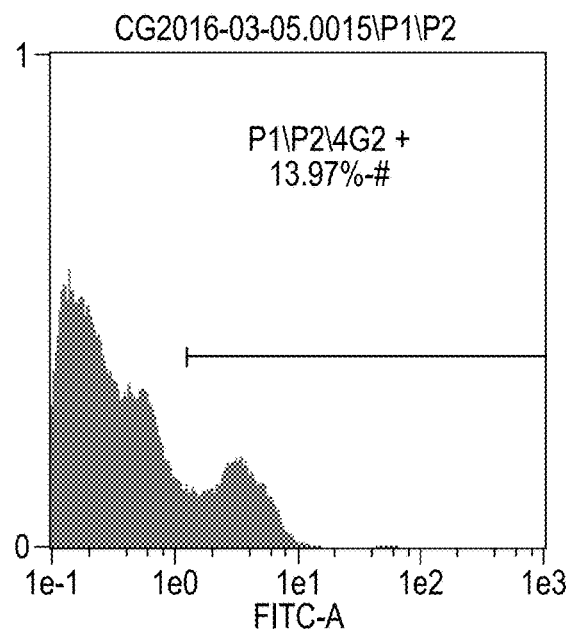
Figure 5E:
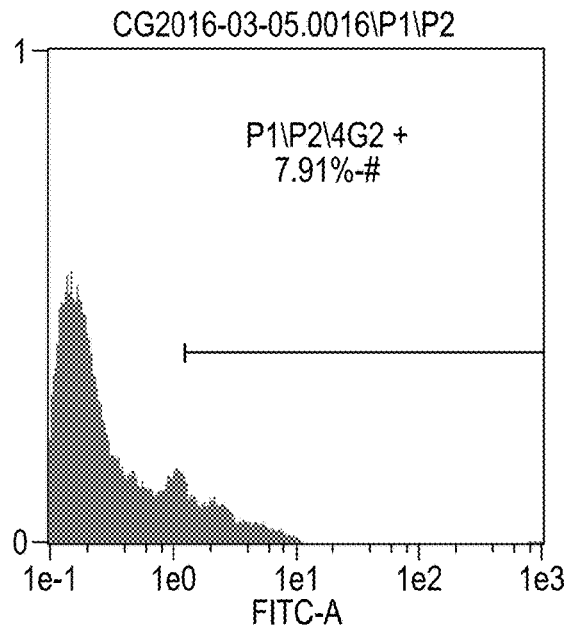
Figure 5F:
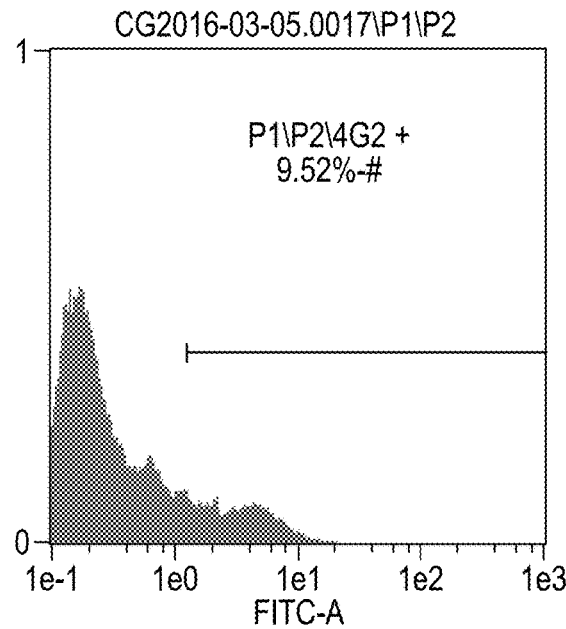
Figure 5G:
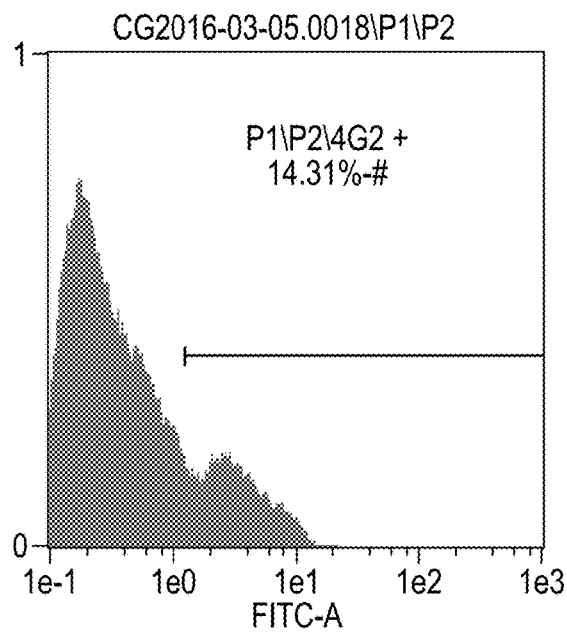
Figure 5H:
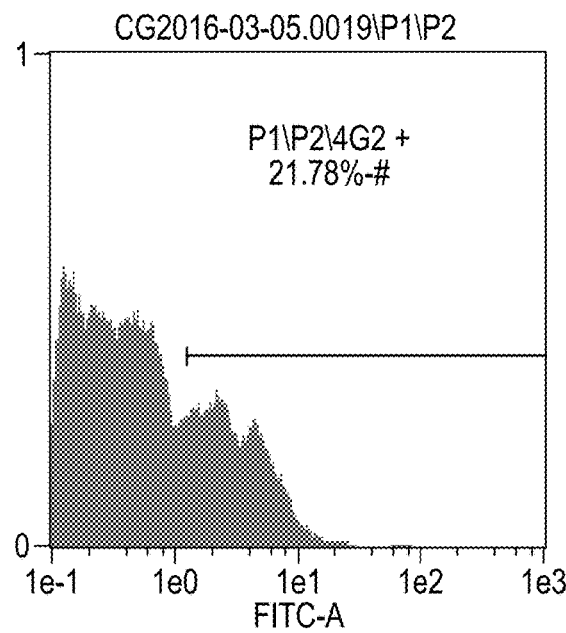

MOI 0.1 results in ~41% of uninfected and Zika-infected Vero cells at Day 3 are shown in FIGS. 2A and 2B. All gates were established using uninfected cells as a control, and were maintained for all test conditions. The data showed that 40.8 percent of the cells were infected.

FIGS. 3A-D show the results of treatment with a compound of the formula:

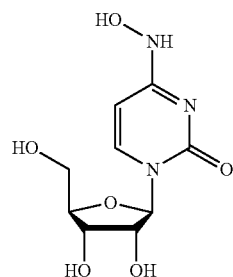

at concentrations of 10 µM, 1 µM, 0.1 µM and 0.01 µM, respectively. The percent inhibition was 57%, 35%, 5%, and 0%, respectively.

FIGS. 4A-D show the results of treatment with a compound of the formula:

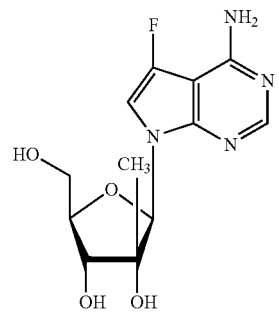

at concentrations of 10 µM, 1 µM, 0.1 µM and 0.01 µM, respectively. The percent inhibition was 83%, 73%, 59%, and 21%, respectively.

FIGS. 5A-H show the results of treatment with compounds of the formulas:

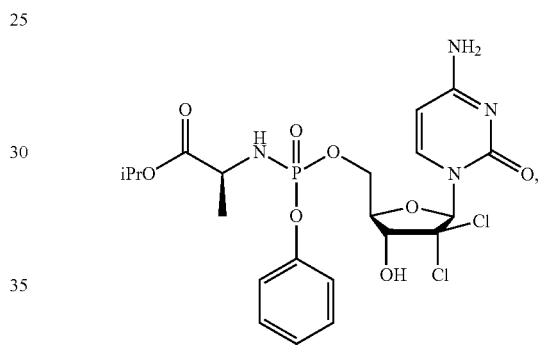

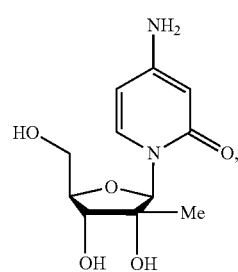

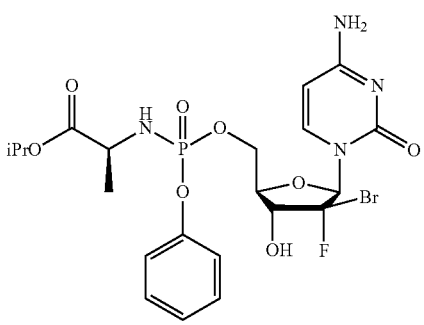

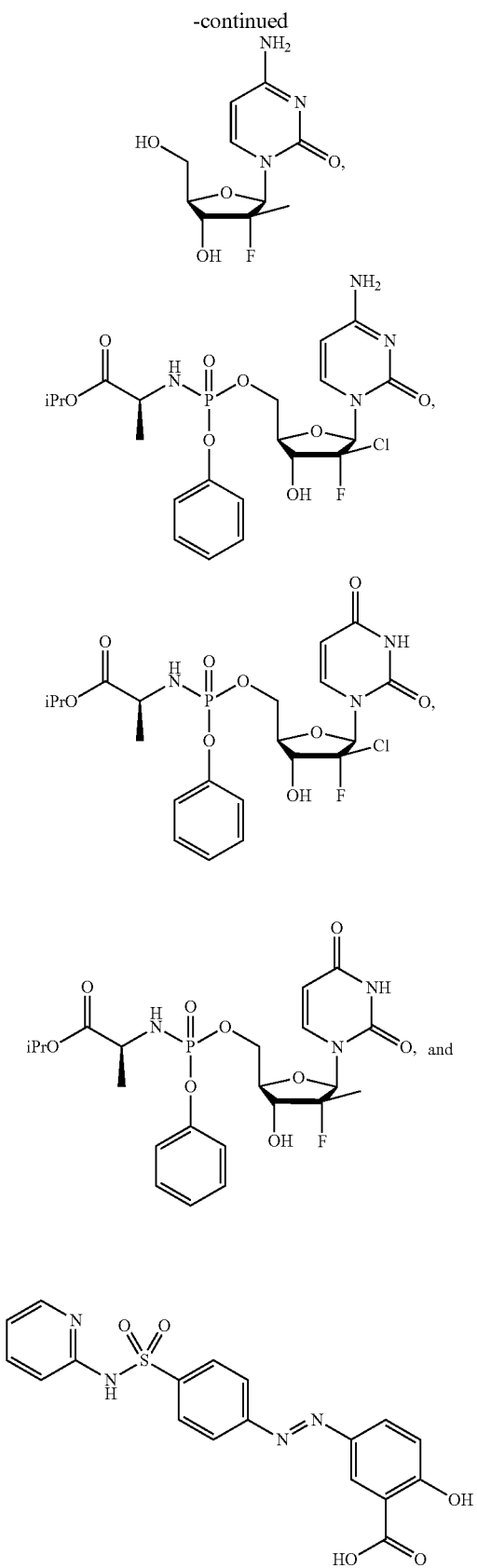

It therefore appears that pyrimidine and purine nucleoside compounds that are active for DENV and/or HCV also demonstrate some potency against Zika virus infection, though at relatively higher concentrations.

Of all the drugs tested, the following inhibitors demonstrated inhibition of 75-83% at 10 µM, without apparent toxicity.

at concentrations of 10 µM. The percent inhibition was 91, 64, 80, 65, 80, 76, 65, and 46%, respectively.

The data is shown in the tables below:

TABLE 1

| Structure | Cytotoxicity: MTT IC$_{50}$ (μM) | | | | | ZIKV CPE MTS Assay IC$_{50}$ (μM) (number in parenthesis) is percentage of inhibition at the concentration) | | |
|---|---|---|---|---|---|---|---|---|
| | PBM | CEM | Vero | HepG2 | Huh7 | Vero | Huh7 | H251 |
| (2'-C-methylcytidine structure) | 65.4 | 84.3 | >100 | 59.1 | >100 | 9.2 | 9.3 | 16.3 |
| (7-fluoro-7-deaza-2'-C-methyladenosine structure) | 83.7 | 33.6 | >100 | | 17.5 | 5.1 | 1.7 | 6.1 |
| (2'-C-methyladenosine structure) | | | | | | 20 | 3.4 | >20 (24%) |
| (3'-C-methyladenosine structure) | >100 | >100 | >100 | | | 13.1 | 1.7 | >10 (37%) |
| (carbocyclic phosphoramidate prodrug structure) | >100 | >100 | >100 | | >100 | >20 (1%) | 2.9 | >20 (42%) |

TABLE 1-continued

| Structure | Cytotoxicity: MTT IC$_{50}$ (μM) | | | | | ZIKV CPE MTS Assay IC$_{50}$ (μM) (number in parenthesis) is percentage of inhibition at the concentration) | | |
|---|---|---|---|---|---|---|---|---|
| | PBM | CEM | Vero | HepG2 | Huh7 | Vero | Huh7 | H251 |
| (structure) | >100 | >100 | >100 | | >100 | >20 (1%) | 5.0 | >20 (27%) |
| (structure) | >100 | >100 | >100 | >100 | >100 | >20 (3%) | <20 (88%) | >20 (34%) |
| (structure) | >100 | 28 | >100 | | 94 | >20 (19%) | 4.7 | >20 (43%) |
| (structure) | >100 | >100 | >100 | | >100 | >20 (1%) | 0.8 | >20 (3%) |
| (structure) | >100 | >100 | >100 | | >100 | >20 (1%) | 11.5 | >20 (20%) |

TABLE 1-continued

| Structure | Cytotoxicity: MTT IC$_{50}$ (μM) | | | | | ZIKV CPE MTS Assay IC$_{50}$ (μM) (number in parenthesis) is percentage of inhibition at the concentration) | | |
|---|---|---|---|---|---|---|---|---|
| | PBM | CEM | Vero | HepG2 | Huh7 | Vero | Huh7 | H251 |
| [structure: iPrO-Ala-phosphoramidate-OPh linked to 2'-methyl-2-amino-adenosine] | >100 | >100 | >100 | | >100 | >20 (1%) | 3.7 | >20 (25%) |
| [structure: isopropyl ester alanine phosphoramidate OPh linked to 2'-methyl ribose with 7-fluoro-7-deazaadenine] | 34.7 | 92.1 | >100 | | | >20 | 7.6 | >10 (1%) |
| [structure: isopropyl ester alanine phosphoramidate OPh linked to 2'-methyl-2'-fluoro uridine] | >100 | >100 | >100 | 49.3 | | >20 (1%) | 5.7 | >20 (17%) |
| [structure: isopropyl ester alanine phosphoramidate OPh linked to 2'-chloro-2'-fluoro uridine] | >100 | >100 | >100 | | | <10 (76%) | | |
| [structure: iPr ester alanine phosphoramidate OPh linked to 2'-chloro-2'-fluoro cytidine] | >100 | >100 | >100 | | | <10 (80%) | | |

TABLE 1-continued

| Structure | Cytotoxicity: MTT IC$_{50}$ (µM) | | | | | ZIKV CPE MTS Assay IC$_{50}$ (µM) (number in parenthesis) is percentage of inhibition at the concentration) | | |
|---|---|---|---|---|---|---|---|---|
| | PBM | CEM | Vero | HepG2 | Huh7 | Vero | Huh7 | H251 |
| (structure) | >100 | >100 | >100 | >100 | | <10 (80%) | | |
| (structure) | >100 | >100 | >100 | >100 | | | | |
| (structure) | 30.6 | 2.5 | 7.7 | | | 3.2 | 5.1 | 4.3 |
| (structure) | >100 | >100 | >100 | >100 | | ≤10 (65%) | | |
| (structure) | 0.9 | 0.2 | 0.2 | 0.3 | | | | |

An assay was also performed (data not shown) on Zika-infected Hofbauer cells (HC) obtained from humans. The activity of those compounds tested at 10 μM in HC is similar to that observed with Vero cells. In conclusion, several NS5B polymerase inhibitory compounds active against HCV are also active against Zika at concentrations below levels at which they are toxic.

TABLE 2

Anti-ZIKV activity of sulfasalazine (SSZ) in three cells types: No pretreat versus pretreat
ZIKV-CPE MTS Assay

| | Compound | | | |
|---|---|---|---|---|
| | SSZ - $EC_{50}$, μM | | Control 1 - $EC_{50}$, μM | |
| Cell Type | No pretreat | Pretreat* | No pretreat | Pretreat* |
| U251 | 384.6 | 317.5 | 3.5 | 4.0 |
| Huh7 | 255.3 | 340.8 | 0.4 | 0.5 |
| Vero | 180.7 | 272.9 | 0.8 | 0.4 |

ZIKV Strain - PRVABC159

*Cells were pretreated with SSZ or control 1 for 18-20 h before infection. Control 1 = beta-D-2'-C—Me-2-amino-7-fluoro-7-deazapurine ribose Effect of Combination of Sulfasalazine (SSZ) with Control 1 on ZIKV Replication in Vero Cells by Using ZIKV CPE Assay.

Vero cells were pretreated for 18-20 h with SSZ (fixed concentrations of 300, 200 or 100 μM) plus control 1 (10, 5, 2.5 and 0.25 μM) prior to infection with MOI 0.01 PRV-ABC59 (drugs were replenished right after infection). The drug combinations were performed as follow:
Sulfasalazine alone (400, 200, 100, and 50 μM).
300 μM Sulfasalazine+10, 5, 2.5 and 0.25 μM Control 1.
200 μM Sulfasalazine+10, 5, 2.5 and 0.25 μM Control 1.
100 μM Sulfasalazine+10, 5, 2.5 and 0.25 μM Control 1.
Control 1 alone (20, 10, 5, 2.5, 1.25 μM).

Drug-drug interactions were analyzed by using CalcuSyn (Biosoft, Ferguson, MO) computer software: 300, 200, and 100 μM SSZ in the presence of 10, 5, 2.5, and 0.25 μM of control 1 was evaluated versus each drug alone for each drug concentration. The interpretation of Combination Index (CI) values are as follows: Antagonism: CI value>1.0, Additive effect: CI value=1.0; Synergism: CI value=<1.0.

Figure 6A:
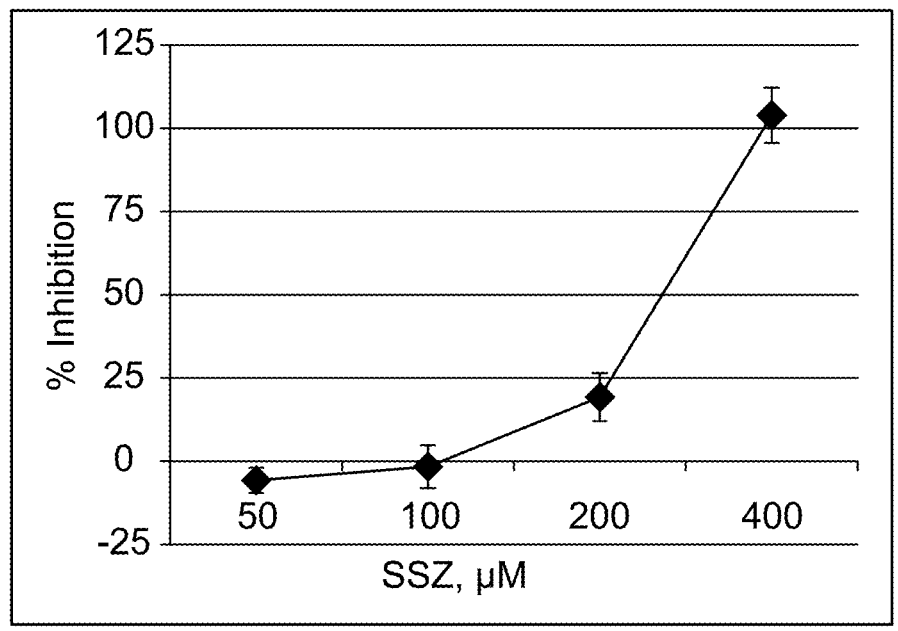
Figure 6B:
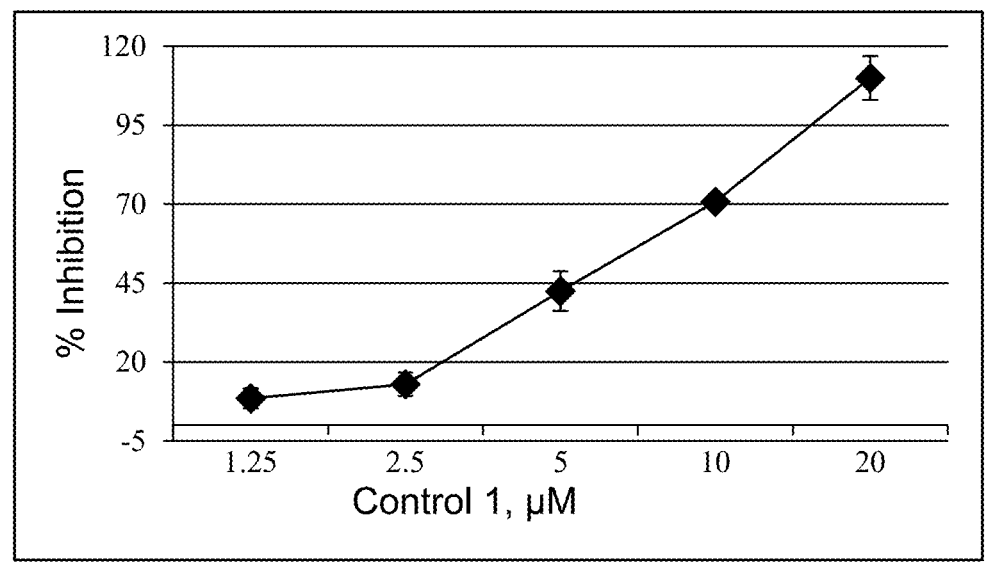
Figure 6C:
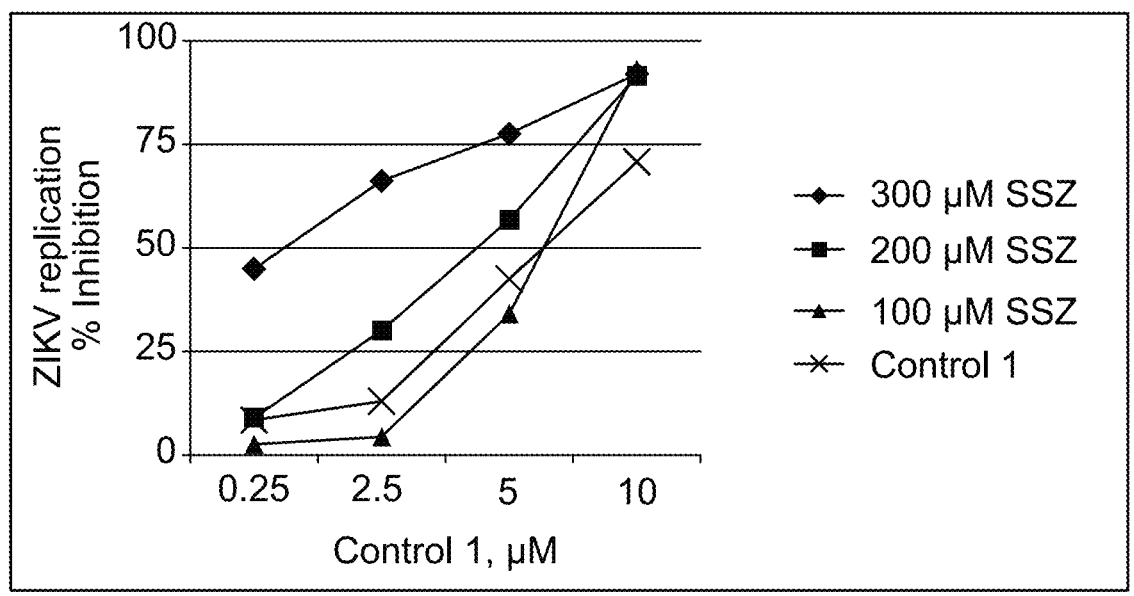

SSZ or control 1 alone demonstrated $EC_{50}$s of 210 μM and 5.4 μM, respectively [FIGS. 6A and 6B. Combination of 100 or 200 μM SSZ with Control 1 demonstrated nearly additive effect, with CI values=1.0 to 1.4 at the lowest and highest concentrations of control 1 (0.25 and 10 μM) (FIG. 6C). The remaining combinations demonstrated CI values from 1.5 to 2.0, indicating slight to moderate antagonism.

All references referred to herein are hereby incorporated by reference for all purposes.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A method for treating a host infected with Zika, preventing an Zika infection, or reducing the biological activity of an Zika infection in a host, comprising administering an effective treatment or preventative amount of a compound or salt thereof to a patient in need of treatment or prevention thereof wherein the compound has one of the following formulas:

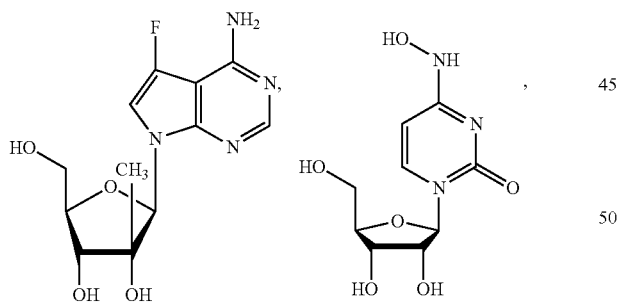

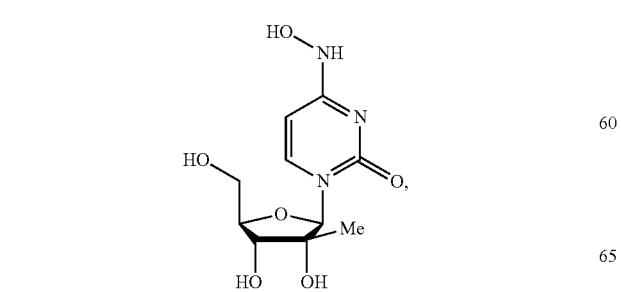

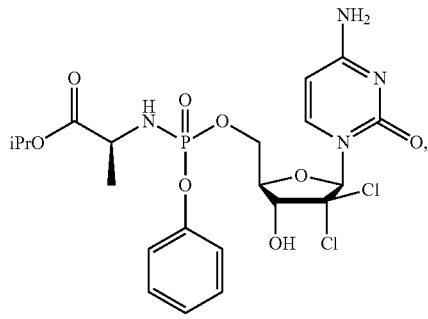

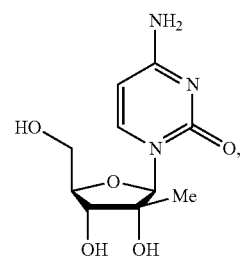

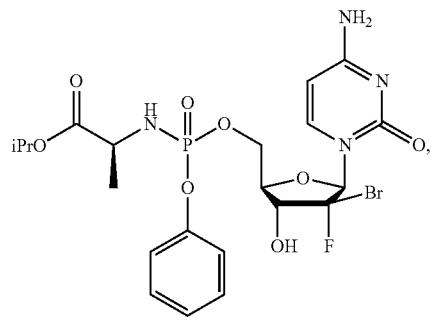

103

-continued

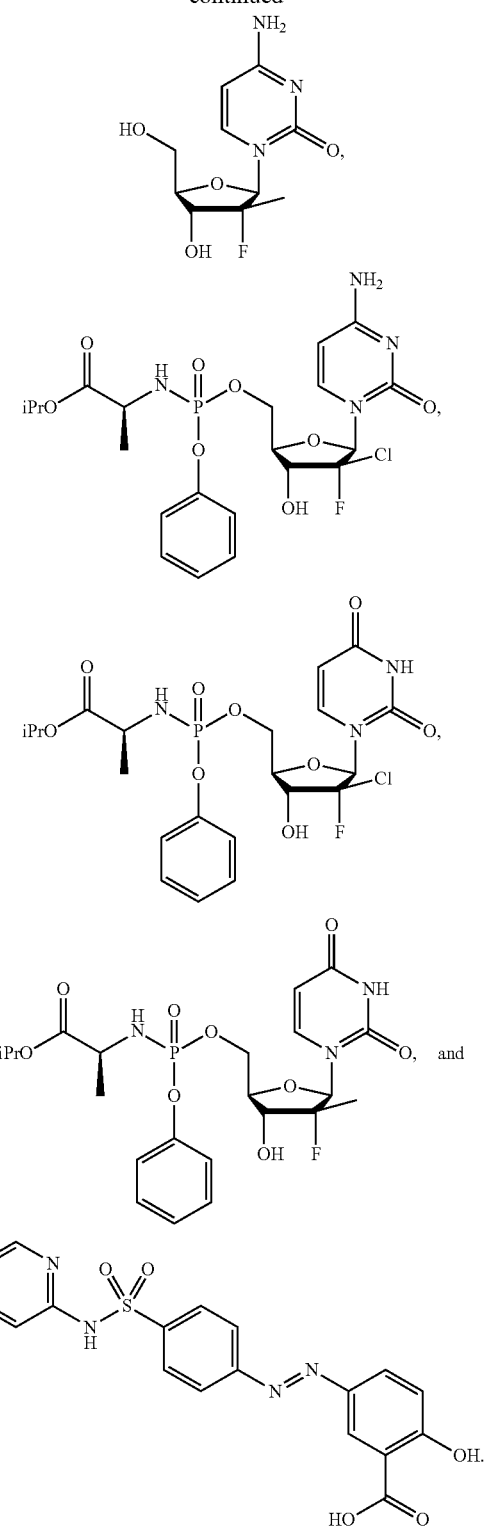

2. A method for treating a host infected with Zika, preventing an Zika infection, or reducing the biological activity of an Zika infection in a host, comprising administering an effective treatment or preventative amount of a compound or salt thereof to a patient in need of treatment or prevention thereof wherein the compound has the formula:

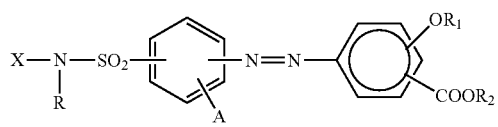

or analogs thereof where, at the 2'-position, the methyl group is replaced with Cl, Br, or F.

3. A method for treating a host infected with Zika, preventing an Zika infection, or reducing the biological activity of an Zika infection in a host, comprising administering an effective treatment or preventative amount of a compound or salt thereof to a patient in need of treatment or prevention thereof wherein the compound is sulfasalazine, ipsalazide, balsalazide, or a sulfasalazine analog of the formula:

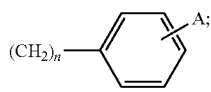

wherein

X is pyridyl, phenyl, phenyl-substituted by lower alkyl, lower alkoxy, halogen, hydroxy, or nitro, furyl, pyrrolyl, quinolyl, pyrimidyl, thienyl or imidazolyl;

R, $R_1$ and $R_2$ are independently H, $C_{1-6}$ alkyl, $C_{1-6}$ aminoalkyl or

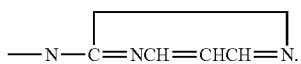

A is H, $C_{1-6}$ alkyl, $C_{1-6}$ aminoalkyl, amino, alkoxy, halo or $CF_3$; and n is 0 to 4, wherein the term pyridyl means 2-pyridyl, 3-pyridyl and 4-pyridyl;

halo is chloro, bromo, iodo, or fluoro; and amino is —$NH_2$, —NH—C($NH_2$)—NH or $$-N-C=NCH=CHCH=N.$$

4. The method of claim 3, wherein the compound is sulfasalazine.

5. A method for treating a host infected with Zika, preventing an Zika infection, or reducing the biological activity of an Zika infection in a host, comprising administering an effective treatment or preventative amount of a compound or salt thereof to a patient in need of treatment or prevention thereof, wherein the compound is

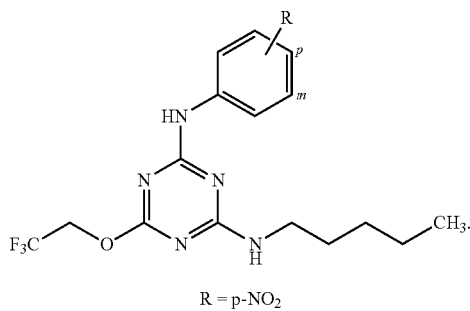

R = p-NO₂

6. The method of claim 5, wherein the compound or salt thereof is administered in combination with a second anti-Zika agent.

7. The method of claim 6, wherein the second anti-Zika agent is galidesivir (BCX4430), an entry inhibitor, a reverse transcriptase inhibitor, a protease inhibitor, or an immune-based therapeutic agent.

8. The method of claim 1, wherein the compound or salt thereof is administered in combination with a second anti-Zika agent.

9. The method of claim 8, wherein the second anti-Zika agent is galidesivir (BCX4430), an entry inhibitor, a reverse transcriptase inhibitor, a protease inhibitor, or an immune-based therapeutic agent.

10. The method of claim 2, wherein the compound or salt thereof is administered in combination with a second anti-Zika agent.

11. The method of claim 10, wherein the second anti-Zika agent is galidesivir (BCX4430), an entry inhibitor, a reverse transcriptase inhibitor, a protease inhibitor, or an immune-based therapeutic agent.

12. The method of claim 3, wherein the compound or salt thereof is administered in combination with a second anti-Zika agent.

13. The method of claim 12, wherein the second anti-Zika agent is galidesivir (BCX4430), an entry inhibitor, a reverse transcriptase inhibitor, a protease inhibitor, or an immune-based therapeutic agent.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial
<220> FEATURE:
<223> OTHER INFORMATION: Synthetic construct

<400> SEQUENCE: 1
tgcccgccat catccta                                                    17

<210> SEQ ID NO 2
<211> LENGTH: 21
<212> TYPE: DNA
<213> ORGANISM: Artificial
<220> FEATURE:
<223> OTHER INFORMATION: Synthetic construct

<400> SEQUENCE: 2
tcctcatcgc cctcccatcc c                                               21

<210> SEQ ID NO 3
<211> LENGTH: 23
<212> TYPE: DNA
<213> ORGANISM: Artificial
<220> FEATURE:
<223> OTHER INFORMATION: Synthetic construct

<400> SEQUENCE: 3
cgtctgttat gtaaaggatg cgt                                             23

<210> SEQ ID NO 4
```

```
<211> LENGTH: 17
<212> TYPE: DNA
<213> ORGANISM: Artificial
<220> FEATURE:
<223> OTHER INFORMATION: Synthetic construct

<400> SEQUENCE: 4
gcgcggctac agcttca                                                    17

<210> SEQ ID NO 5
<211> LENGTH: 18
<212> TYPE: DNA
<213> ORGANISM: Artificial
<220> FEATURE:
<223> OTHER INFORMATION: Synthetic construct

<400> SEQUENCE: 5
caccacggcc gagcggga                                                   18

<210> SEQ ID NO 6
<211> LENGTH: 22
<212> TYPE: DNA
<213> ORGANISM: Artificial
<220> FEATURE:
<223> OTHER INFORMATION: Synthetic construct

<400> SEQUENCE: 6
tctccttaat gtcacgcacg at                                              22
```